US006423521B1

(12) United States Patent
Chandramouliswaran et al.

(10) Patent No.: US 6,423,521 B1
(45) Date of Patent: Jul. 23, 2002

(54) ISOLATED HUMAN KINASE PROTEINS, NUCLEIC ACID MOLECULES ENCODING HUMAN KINASE PROTEINS, AND USES THEREOF

(75) Inventors: Ishwar Chandramouliswaran, Silver Spring, MD (US); Karl Guegler, Menlo Park; Marion Webster, San Francisco, both of CA (US); Chunhua Yan, Boyds, MD (US); Valentina Di Francesco, Rockville, MD (US); Ellen M. Beasley, Darnestown, MD (US)

(73) Assignee: PE Corporation (NY), Norwalk, CT (US)

( * ) Notice: Subject to any disclaimer, the term of this patent is extended or adjusted under 35 U.S.C. 154(b) by 0 days.

(21) Appl. No.: 09/749,588

(22) Filed: Dec. 28, 2000

(51) Int. Cl.[7] ............................ C12N 9/12; C12N 1/12; C12N 15/00; C12N 5/00; C07H 21/04
(52) U.S. Cl. .................... 435/194; 435/325; 435/252.3; 435/320.1; 536/23.2
(58) Field of Search ................................. 435/194, 325, 435/252.3, 320.1; 536/23.2

(56) References Cited

PUBLICATIONS

GenEMBL Database, Accession No. AF170304, Sep. 1999.*

* cited by examiner

*Primary Examiner*—Rebecca E. Prouty
*Assistant Examiner*—Maryam Monshipouri
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

9 Claims, 23 Drawing Sheets

```
   1 TTCTTCCTTT CTCTCAATAT AGGTATGGCA TCACAGCTGC AAGTGTTTTC
  51 GCCCCCATCA GTGTCGTCGA GTGCCTTCTG CAGTGCGAAG AAACTGAAAA
 101 TAGAGCCCTC TGGCTGGGAT GTTTCAGGAC AGAGTAGCAA CGACAAATAT
 151 TATACCCACA GCAAAACCCT CCCAGCCACA CAAGGGCAAG CCAACTCCTC
 201 TCACCAGGTA GCAAATTTCA ACATCCCTGC TTACGACCAG GGCCTCCTCC
 251 TCCCAGCTCC TGCAGTGGAA CATATTGTTG TAACAGCCGC TGATAGCTCG
 301 GGCAGTGCTG CTACATCAAC CTTCCAAAGC AGCCAGACCC TGACTCACAG
 351 AAGCAACGTT TCTTTGCTTG AGCCATATCA AAATGTGGA TTGAAACGAA
 401 AAAGTGAGGA AGTTGACAGC AACGGTAGTG TGCAGATCAT AGAAGAACAT
 451 CCCCCTCTCA TGCTGCAAAA CAGGACTGTG GTGGGTGCTG CTGCCACAAC
 501 CACCACTGTG ACCACAAAGA GTAGCAGTTC CAGCGGAGAA GGGGATTACC
 551 AGCTGGTCCA GCATGAGATC CTTTGCTCTA TGACCAATAG CTATGAAGTC
 601 TTGGAGTTCC TAGGCCGGGG GACATTTGGA CAGGTGGCTA AGTGCTGGAA
 651 GAGGAGCACC AAGGAAATTG TGGCTATTAA AATCTTGAAG AACCACCCCT
 701 CCTATGCCAG ACAAGGACAG ATTGAAGTGA GCATCCTTTC CCGCCTAAGC
 751 AGTGAAAATG CTGATGAGTA TAATTTTGTC CGTTCATACG AGTGCTTTCA
 801 GCATAAGAAT CACACCTGCC TTGTTTTTGA AATGTTGGAG CAGAACTTAT
 851 ATGATTTTCT AAAGCAAAAC AAATTTAGCC CACTGCCACT CAAGTACATC
 901 AGACCAATCT TGCAGCAGGT GGCCACAGCC TTGATGAAGC TCAAGAGTCT
 951 TGGTCTGATC CACGCTGACC TTAAGCCTGA AAACATCATG CTGGTTGATC
1001 CAGTTCGCCA GCCCTACCGA GTGAAGGTCA TTGACTTTGG TTCTGCTAGT
1051 CACGTTTCCA AAGCTGTGTG CTCAACCTAC TTACAGTCAC GTTACTACAG
1101 AGCTCCTGAA ATTATTCTTG GGTTACCATT TTGTGAAGCT ATTGATATGT
1151 GGTCACTGGG CTGTGTGATA GCTGAGCTGT TCCTGGGATG GCCTCTTTAT
1201 CCTGGTGCTT CAGAATATGA TCAGACACCT GAAGAACACG AACTGGAGAC
1251 TGGAATAAAA TCAAAGAAG CTCGGAAGTA CATTTTTAAT TGCTTAGATG
1301 ACATGGCTCA GGTGAATATG TCTACAGACC TGGAGGGAAC AGACATGTTG
1351 GCAGAGAAGG CAGACCGAAG AGAATACATT GATCTGTTAA AGAAAATGCT
1401 CACAATTGAT GCAGATAAGA GAATTACCCC TCTAAAAACT CTTAACCATC
1451 AGTTTGTGAC AATGACTCAC CTTTTGGATT TTCCACATAG CAATCATGTT
1501 AAGTCTTGTT TTCAGAACAT GGAGATCTGC AAGCGGAGGG TTCACATGTA
1551 TGATACAGTG AATCAGATCA AGAGTCCCTT CACTACACAT GTTGCCCCAA
1601 ATACAAGCAC AAATCTAACC ATGAGCTTCA GCAATCAGCT CAATACAGTG
1651 CACAATCAGG CCAGTGTTCT AGCTTCCAGT TCTACTGCAG CAGCTGCTAC
1701 TCTTTCTCTG GCTAATTCAG ATGTCTCACT ACTAAACTAC CAGTCAGCTT
1751 TGTACCCATC ATCTGCTGCA CCAGTTCCTG GAGTTGCCCA GCAGGGTGTT
1801 TCCTTGCAGC CTGGAACCAC CCAGATTTGC ACTCAGACAG ATCCATTCCA
1851 ACAGACATTT ATAGTATGTC CACCTGCGTT TCAAACTGGA CTACAAGCAA
1901 CAACAAAGCA TTCTGGATTC CCTGTGAGGA TGGATAATGC TGTACCGATT
1951 GTACCCCAGG CACCAGCTGC TCAGCCACTA CAGATTCAGT CAGGAGTTCT
2001 CACGCAGGGA AGCTGTACAC CACTAATGGT AGCAACTCTC CACCCTCAAG
2051 TAGCCACCAT CACGCCGCAG TATGCGGTGC CCTTTACTCT GAGCTGCGCA
2101 GCCGGCCGGC CGGCGCTGGT TGAACAGACT GCCGCTGTAC TGCAGGCGTG
2151 GCCTGGAGGG ACTCAGCAAA TTCTCCTGCC TTCAACTTGG CAACAGTTGC
2201 CTGGGGTAGC TCTACACAAC TCTGTCCAGC CCACAGCAAT GATTCCAGAG
2251 GCCATGGGGA GTGGACAGCA GCTAGCTGAC TGGAGGAATG CCCACTCTCA
2301 TGGCAACCAG TACAGCACTA TCATGCAGCA GCCATCCTTG CTGACTAACC
2351 ATGTGACATT GGCCACTGCT CAGCCTCAAT GTTGGTGTTG CCCATGTTGT
2401 CTGACAACAA CAATCCAGTT CCCTCCCTTC GAAGAAGAAT AAGCAGTCAG
2451 CTCCAGTCTC TTCCAAGTCC TCTCTAGATG TTCTGCCTTC CCAAGTCTAT
2501 TCTCTGGTTG GGAGCAGTCC CCTCCGCACC ACATCTTCTT ATAATTCCTT
2551 GGTCCCTGTC CAAGATCAGC ATCAGCCCAT CATCATTCCA GATACTCCCA
2601 GCCCTCCTGT GAGTGTCATC ACTATCCGAA GTGACACTGA TGAGGAAGAG
2651 GACAACAAAT ACAAGCCCAG TAGCTCTGGA CTGAAGCCAA GGTCTAATGT
2701 CATCAGTTAT GTCACTGTCA ATGATTCTCC AGACTCTGAC TCTTCTTTGA
2751 GCAGCCCTTA TTCCACTGAT ACCCTGAGTG CTCTCCGAGG CAATAGTGGA
2801 TCCGTTTTGG AGGGGCCTGG CAGAGTTGTG GCAGATGGCA CTGGCACCCG
```

FIGURE 1A

```
2851 CACTATCATT GTGCCTCCAC TGAAAACTCA GCTTGGTGAC TGCACTGTAG
2901 CAACCCAGGC CTCAGGTCTC CTGAGCAATA AGACTAAGCC AGTCGCTTCA
2951 GTGAGTGGGC AGTCATCTGG ATGCTGTATC ACCCCCACAG GGTATCGAGC
3001 TCAACGCGGG GGGACCAGTG CAGCACAACC ACTCAATCTT AGCAGAACC
3051 AGCAGTCATC GGCGGCTCCA ACCTCACAGG AGAGAAGCAG CAACCCAGCC
3101 CCCCGCAGGC AGCAGGCATT TGTGGCCCCT CTCTCCCAAG CCCCCTACAC
3151 CTTCCAGCAT GGCAGCCCGC TACACTCGAC AGGGCACCCA CACCTTGCCC
3201 CGGCCCCTGC TCACCTGCCA AGCCAGGCTC ATCTGTATAC GTATGCTGCC
3251 CCGACTTCTG CTGCTGCACT GGGCTCAACC AGCTCCATTG CTCATCTTTT
3301 CTCCCCACAG GGTTCCTCAA GGCATGCTGC AGCCTATACC ACTCACCCTA
3351 GCACTTTGGT GCACCAGGTC CCTGTCAGTG TTGGGCCCAG CCTCCTCACT
3401 TCTGCCAGCG TGGCCCCTGC TCAGTACCAA CACCAGTTTG CCACCCAATC
3451 CTACATTGGG TCTTCCCGAG GCTCAACAAT TTACACTGGA TACCCGCTGA
3501 GTCCTACCAA GATCAGCCAG TATTCCTACT TATAGTTGGT GAGCATGAGG
3551 AAGGGCGAAT TCTGT (SEQ ID NO:1)
```

FEATURES:
5'UTR:        1-24
Start Codon:  25
Stop Codon:   3533
3'UTR:        3536-3565

Homologous proteins:
Top 10 BLAST Hits

| | Score | E |
|---|---|---|
| gi\|5305331\|gb\|AAD41592.1\|AF071070_1 (AF071070) protein kinase M... | 2279 | 0.0 |
| gi\|6754196\|ref\|NP_034562.1\| homeodomain interacting protein kin... | 2271 | 0.0 |
| gi\|5815143\|gb\|AAD52568.1\|AF170303_1 (AF170303) nuclear body ass... | 2135 | 0.0 |
| gi\|5815141\|gb\|AAD52567.1\|AF170302_1 (AF170302) nuclear body ass... | 1392 | 0.0 |
| gi\|6754198\|ref\|NP_034563.1\| homeodomain interacting protein kin... | 1389 | 0.0 |
| gi\|5815139\|gb\|AAD52566.1\|AF170301_1 (AF170301) nuclear body ass... | 1346 | 0.0 |
| gi\|4868443\|gb\|AAD31319.1\|AF144573_1 (AF144573) Mx-interacting p... | 1343 | 0.0 |
| gi\|5305333\|gb\|AAD41593.1\|AF071071_1 (AF071071) protein kinase M... | 1224 | 0.0 |
| gi\|11493928\|gb\|AAG35710.1\|AF207702_1 (AF207702) homeodomain-int... | 1092 | 0.0 |
| gi\|3327074\|dbj\|BAA31605.1\| (AB014530) KIAA0630 protein [Homo sa... | 979 | 0.0 |

BLAST to dbEST:

| | Score | E |
|---|---|---|
| gi\|3739409 /dataset=dbest /taxon=9606 ... | 904 | 0.0 |
| gi\|6397638 /dataset=dbest /taxon=9606 ... | 880 | 0.0 |
| gi\|675163  /dataset=dbest /taxon=9606 /... | 839 | 0.0 |
| gi\|3203240 /dataset=dbest /taxon=9606 ... | 642 | 0.0 |
| gi\|1969707 /dataset=dbest /taxon=9606 ... | 563 | e-157 |
| gi\|2567079 /dataset=dbest /taxon=9606 ... | 561 | e-157 |
| gi\|708590  /dataset=dbest /taxon=9606 /... | 545 | e-152 |
| gi\|706328  /dataset=dbest /taxon=9606 /... | 478 | e-132 |
| gi\|11592336 /dataset=dbest /taxon=960... | 416 | e-113 |

FIGURE 1B

EXPRESSION INFORMATION FOR MODULATORY USE:
library source:
Expression information from BLAST dbEST hits:
gi|3739409   Testis
gi|6397638   Brain medulloblastoma
gi|675163    Infant brain
gi|3203240   Schizophrenic brain
gi|1969707   Retina
gi|2567079   Germinal center B cells
gi|708590    Infant brain
gi|706328    Infant brain
gi|11592336  Colon Expression information from PCR-based tissue screening panels:
Human liver

FIGURE 1C

```
   1 MASQLQVFSP PSVSSSAFCS AKKLKIEPSG WDVSGQSSND KYYTHSKTLP
  51 ATQGQANSSH QVANFNIPAY DQGLLLPAPA VEHIVVTAAD SSGSAATSTF
 101 QSSQTLTHRS NVSLLEPYQK CGLKRKSEEV DSNGSVQIIE EHPPLMLQNR
 151 TVVGAAATTT TVTTKSSSSS GEGDYQLVQH EILCSMTNSY EVLEFLGRGT
 201 FGQVAKQWKR STKEIVAIKI LKNHPSYARQ GQIEVSILSR LSSENADEYN
 251 FVRSYECFQH KNHTCLVFEM LEQNLYDFLK QNKFSPLPLK YIRPILQQVA
 301 TALMKLKSLG LIHADLKPEN IMLVDPVRQP YRVKVIDFGS ASHVSKAVCS
 351 TYLQSRYYRA PEIILGLPFC EAIDMWSLGC VIAELFLGWP LYPGASEYDQ
 401 TPEEHELETG IKSKEARKYI FNCLDDMAQV NMSTDLEGTD MLAEKADRRE
 451 YIDLLKKMLT IDADKRITPL KTLNHQFVTM THLLDFPHSN HVKSCFQNME
 501 ICKRRVHMYD TVNQIKSPFT THVAPNTSTN LTMSFSNQLN TVHNQASVLA
 551 SSSTAAAATL SLANSDVSLL NYQSALYPSS AAPVPGVAQQ GVSLQPGTTQ
 601 ICTQTDPFQQ TFIVCPPAFQ TGLQATTKHS GFPVRMDNAV PIVPQAPAAQ
 651 PLQIQSGVLT QGSCTPLMVA TLHPQVATIT PQYAVPFTLS CAAGRPALVE
 701 QTAAVLQAWP GGTQQILLPS TWQQLPGVAL HNSVQPTAMI PEAMGSGQQL
 751 ADWRNAHSHG NQYSTIMQQP SLLTNHVTLA TAQPLNVGVA HVVRQQQSSS
 801 LPSKKNKQSA PVSSKSSLDV LPSQVYSLVG SSPLRTTSSY NSLVPVQDQH
 851 QPIIIPDTPS PPVSVITIRS DTDEEEDNKY KPSSSGLKPR SNVISYVTVN
 901 DSPDSDSSLS SPYSTDTLSA LRGNSGSVLE GPGRVVADGT GTRTIIVPPL
 951 KTQLGDCTVA TQASGLLSNK TKPVASVSGQ SSGCCITPTG YRAQRGGTSA
1001 AQPLNLSQNQ QSSAAPTSQE RSSNPAPRRQ QAFVAPLSQA PYTFQHGSPL
1051 HSTGHPHLAP APAHLPSQAH LYTYAAPTSA AALGSTSSIA HLFSPQGSSR
1101 HAAAYTTHPS TLVHQVPVSV GPSLLTSASV APAQYQHQFA TQSYIGSSRG
1151 STIYTGYPLS PTKISQYSYL (SEQ ID NO:2)

FEATURES:
Functional domains and key regions:
[1] PDOC00001 PS00001 ASN_GLYCOSYLATION
N-glycosylation site Number of matches: 10
       1     57-60   NSSH
       2   111-114   NVSL
       3   133-136   NGSV
       4   149-152   NRTV
       5   262-265   NHTC
       6   431-434   NMST
       7   526-529   NTST
       8   530-533   NLTM
       9   969-972   NKTK
      10  1005-1008  NLSQ

[2] PDOC00004 PS00004 CAMP_PHOSPHO_SITE
cAMP- and cGMP-dependent protein kinase phosphorylation site Number of matches: 3
       1   124-127   KRKS
       2   209-212   KRST
       3   465-468   KRIT
```

FIGURE 2A

[3] PDOC00005 PS00005 PKC_PHOSPHO_SITE
Protein kinase C phosphorylation site

Number of matches: 11
1      20-22   SAK
2     107-109  THR
3     163-165  TTK
4     626-628  TTK
5     211-213  STK
6     163-165  TTK
7     626-628  TTK
8     803-805  SKK
9     813-815  SSK
10    867-869  TIR
11    968-970  SNK

[4] PDOC00006 PS00006 CK2_PHOSPHO_SITE
Casein kinase II phosphorylation site

Number of matches: 16
1      29-32   SGWD
2      37-40   SSND
3      87-90   TAAD
4     113-116  SLLE
5     169-172  SSGE
6     211-214  STKE
7     396-399  SEYD
8     401-404  TPEE
9     434-437  TDLE
10    603-606  TQTD
11    816-819  SSLD
12    870-873  SDTD
13    872-875  TDEE
14    898-901  TVND
15    927-930  SVLE
16   1017-1020 TSQE

[5] PDOC00007 PS00007 TYR_PHOSPHO_SITE
Tyrosine kinase phosphorylation site 412-419 KSKEARKY

[6] PDOC00008 PS00008 MYRISTYL
N-myristoylation site

Number of matches: 17
1      35-40   GQSSND
2      54-59   GQANSS
3      93-98   GSAATS
4     154-159  GAAATT
5     310-315  GLIHAD
6     366-371  GLPFCE
7     379-384  GCVIAE
8     622-627  GLQATT
9     747-752  GQQLAD
10    760-765  GNQYST
11    923-928  GNSGSV
12    965-970  GLLSNK

FIGURE 2B

```
13    979-984   GQSSGC
14    996-1001  GGTSAA
15    997-1002  GTSAAQ
16    1084-1089 GSTSSI
17    1146-1151 GSSRGS
```

[7] PDOC00100 PS00107 PROTEIN_KINASE_ATP
Protein kinases ATP-binding region signature 196-219 LGRGTFGQVAKCWKRSTKEIVAIK

[8] PDOC00100 PS00108 PROTEIN_KINASE_ST
Serine/Threonine protein kinases active-site signature 311-323 LIHADLKPENIML Membrane spanning structure and domains:

| Helix | Begin | End  | Score | Certainty |
|-------|-------|------|-------|-----------|
| 1     | 8     | 28   | 0.859 | Putative  |
| 2     | 157   | 177  | 0.671 | Putative  |
| 3     | 381   | 401  | 1.258 | Certain   |
| 4     | 551   | 571  | 1.305 | Certain   |
| 5     | 578   | 598  | 0.603 | Putative  |
| 6     | 613   | 633  | 0.801 | Putative  |
| 7     | 660   | 680  | 1.130 | Certain   |
| 8     | 683   | 703  | 0.669 | Putative  |
| 9     | 977   | 997  | 0.752 | Putative  |
| 10    | 1081  | 1101 | 1.230 | Certain   |
| 11    | 1121  | 1141 | 1.197 | Certain   |

BLAST Alignment to Top Hit:
>gi|6754196|ref|NP_034562.1| homeodomain interacting protein kinase 1
            [Mus musculus]
  pir||T14357 homeodomain-interacting protein kinase 1 - mouse
  gb|AAC63010.1| (AF077658) homeodomain-interacting protein kinase 1 [Mus musculus]
            Length = 1209

Score = 2271 bits (5820), Expect = 0.0
Identities = 1139/1210 (94%), Positives = 1155/1210 (95%), Gaps = 40/1210 (3%)
Frame = +1

```
Query: 1    MASQLQVFSPPSVSSSAFCSAKKLKIEPSGWDVSGQSSNDKYYTHSKTLPATQGQANSSH 180
            MASQLQVFSPPSVSSSAFCSAKKLKIEPSGWDVSGQSSNDKYYTHSKTLPATQGQA+SSH
Sbjct: 1    MASQLQVFSPPSVSSSAFCSAKKLKIEPSGWDVSGQSSNDKYYTHSKTLPATQGQASSSH 60

Query: 181  QVANFNIPAYDQGLLLLPAPAVEHIVVTAADSSGSAATSTFQSSQTLTHRSNVSLLEPYQK 360
            QVANFN+PAYDQGLLLLPAPAVEHIVVTAADSSGSAAT+TFQSSQTLTHRSNVSLLEPYQK
Sbjct: 61   QVANFNLPAYDQGLLLLPAPAVEHIVVTAADSSGSAATATFQSSQTLTHRSNVSLLEPYQK 120

Query: 361  CGLKRKSEEVDSNGSVQIIEEHPPLMLQNRTVVGAAATTTTVTTKSSSSSGEGDYQLVQH 540
            CGLKRKSEEV+SNGSVQIIEEHPPLMLQNRTVVGAAATTTTVTTKSSSSSGEGDYQLVQH
Sbjct: 121  CGLKRKSEEVESNGSVQIIEEHPPLMLQNRTVVGAAATTTTVTTKSSSSSGEGDYQLVQH 180

Query: 541  EILCSMTNSYEVLEFLGRGTFGQVAKCWKRSTKEIVAIKILKNHPSYARQGQIEVSILSR 720
            EILCSMTNSYEVLEFLGRGTFGQVAKCWKRSTKEIVAIKILKNHPSYARQGQIEVSILSR
Sbjct: 181  EILCSMTNSYEVLEFLGRGTFGQVAKCWKRSTKEIVAIKILKNHPSYARQGQIEVSILSR 240
```

FIGURE 2C

```
Query:  721 LSSENADEYNFVRSYECFQHKNHTCLVFEMLEQNLYDFLKQNKFSPLPLKYIRPILQQVA  900
             LSSENADEYNFVRSYECFQHKNHTCLVFEMLEQNLYDFLKQNKFSPLPLKYIRPILQQVA
Sbjct:  241 LSSENADEYNFVRSYECFQHKNHTCLVFEMLEQNLYDFLKQNKFSPLPLKYIRPILQQVA  300

Query:  901 TALMKLKSLGLIHADLKPENIMLVDPVRQPYRVKVIDFGSASHVSKAVCSTYLQSRYYRA 1080
             TALMKLKSLGLIHADLKPENIMLVDPVRQPYRVKVIDFGSASHVSKAVCSTYLQSRYYRA
Sbjct:  301 TALMKLKSLGLIHADLKPENIMLVDPVRQPYRVKVIDFGSASHVSKAVCSTYLQSRYYRA  360

Query: 1081 PEIILGLPFCEAIDMWSLGCVIAELFLGWPLYPGASEYDQ-------------------- 1200
             PEIILGLPFCEAIDMWSLGCVIAELFLGWPLYPGASEYDQ
Sbjct:  361 PEIILGLPFCEAIDMWSLGCVIAELFLGWPLYPGASEYDQIRYISQTQGLPAEYLLSAGT  420

Query: 1201 --------------------TPEEHELETGIKSKEARKYIFNCLDDMAQVNMSTDLEGTD 1320
                                 TPEEHELETGIKSKEARKYIFNCLDDMAQVNMSTDLEGTD
Sbjct:  421 KTTRFFNRDPNLGYPLWRLKTPEEHELETGIKSKEARKYIFNCLDDMAQVNMSTDLEGTD  480

Query: 1321 MLAEKADRREYIDLLKKMLTIDADKRITPLKTLNHQFVTMTHLLDFPHSNHVKSCFQNME 1500
             MLAEKADRREYIDLLKKMLTIDADKRITPLKTLNHQFVTM+HLLDFPHS+HVKSCFQNME
Sbjct:  481 MLAEKADRREYIDLLKKMLTIDADKRITPLKTLNHQFVTMSHLLDFPHSSHVKSCFQNME  540

Query: 1501 ICKRRVHMYDTVNQIKSPFTTHVAPNTSTNLTMSFSNQLNTVHNQASVLASSSTAAAATL 1680
             ICKRRVHMYDTV+QIKSPFTTHVAPNTSTNLTMSFSNQLNTVHNQASVLASSSTAAAATL
Sbjct:  541 ICKRRVHMYDTVSQIKSPFTTHVAPNTSTNLTMSFSNQLNTVHNQASVLASSSTAAAATL  600

Query: 1681 SLANSDVSLLNYQSALYPSSAAPVPGVAQQGVSLQPGTTQICTQTDPFQQTFIVCPPAFQ 1860
             SLANSDVSLLNYQSALYPSSAAPVPGVAQQGVSLQPGTTQICTQTDPFQQTFIVCPPAFQ
Sbjct:  601 SLANSDVSLLNYQSALYPSSAAPVPGVAQQGVSLQPGTTQICTQTDPFQQTFIVCPPAFQ  660

Query: 1861 TGLQATTKHSGFPVRMDNAVPIVPQAPAAQPLQIQSGVLTQGSCTPLMVATLHPQVATIT 2040
             TGLQATTKHSGFPVRMDNAVPIVPQAPAAQPLQIQSGVLTQGSCTPLMVATLHPQVATIT
Sbjct:  661 TGLQATTKHSGFPVRMDNAVPIVPQAPAAQPLQIQSGVLTQGSCTPLMVATLHPQVATIT  720

Query: 2041 PQYAVPFTLSCAAGRPALVEQTAAVLQAWPGGTQQILLPSTWQQLPGVALHNSVQPTAMI 2220
             PQYAVPFTLSCA GRPALVEQTAAVLQAWPGGTQQILLPS WQQLPGVALHNSVQP A+I
Sbjct:  721 PQYAVPFTLSCA-GRPALVEQTAAVLQAWPGGTQQILLPSAWQQLPGVALHNSVQPAAVI  779

Query: 2221 PEAMGSGQQLADWRNAHSHGNQYSTIMQQPSLLTNHVTLATAQPLNVGVAHVVRQQQSSS 2400
             PEAMGS QQLADWRNAHSHGNQYSTIMQQPSLLTNHVTLATAQPLNVGVAHVVRQQQSSS
Sbjct:  780 PEAMGSSQQLADWRNAHSHGNQYSTIMQQPSLLTNHVTLATAQPLNVGVAHVVRQQQSSS  839

Query: 2401 LPSKKNKQSAPVSSKSSLDVLPSQVYSLVGSSPLRTTSSYNSLVPVQDQHQPIIIPDTPS 2580
             LPSKKNKQSAPVSSKSSL+VLPSQVYSLVGSSPLRTTSSYNSLVPVQDQHQPIIIPDTPS
Sbjct:  840 LPSKKNKQSAPVSSKSSLEVLPSQVYSLVGSSPLRTTSSYNSLVPVQDQHQPIIIPDTPS  899

Query: 2581 PPVSVITIRSDTDEEEDNKYKPSSSGLKPRSNVISYVTVNDSPDSDSSLSSPYSTDTLSA 2760
             PPVSVITIRSDTDEEEDNKY+P+SS LK RSNVISYVTVNDSPDSDSSLSSP+STDTLSA
Sbjct:  900 PPVSVITIRSDTDEEEDNKYEPNSSSLKARSNVISYVTVNDSPDSDSSLSSPHSTDTLSA  959

Query: 2761 LRGNSGSVLEGPGRVVADGTGTRTIIVPPLKTQLGDCTVATQASGLLSNKTKPVASVSGQ 2940
             LRGNSG++LEGPGR  ADG GTRTIIVPPLKTQLGDCTVATQASGLLS+KTKPVASVSGQ
Sbjct:  960 LRGNSGTLLEGPGRPAADGIGTRTIIVPPLKTQLGDCTVATQASGLLSSKTKPVASVSGQ 1019

Query: 2941 SSGCCITPTGYRAQRGGTSAAQPLNLSQNQQSSAAPTSQERSSNPAPRRQQAFVAPLSQA 3120
             SSGCCITPTGYRAQRGG SA QPLNLSQNQQSS+A TSQERSSNPAPRRQQAFVAPLSQA
Sbjct: 1020 SSGCCITPTGYRAQRGGASAVQPLNLSQNQQSSSASTSQERSSNPAPRRQQAFVAPLSQA 1079
```

FIGURE 2D

```
Query: 3121 PYTFQHGSPLHSTGHPHLAPAPAHLPSQAHLYTYAAPTSAAALGSTSSIAHLFSPQGSSR 3300
             PY FQHGSPLHSTGHPHLAPAPAHLPSQ HLYTYAAPTSAAALGSTSSIAHLF PQGSSR
Sbjct: 1080 PYAFQHGSPLHSTGHPHLAPAPAHLPSQPHLYTYAAPTSAAALGSTSSIAHLFFPQGSSR 1139

Query: 3301 HAAAYTTHPSTLVHQVPVSVGPSLLTSASVAPAQYQHQFATQSYIGSSRGSTIYTGYPLS 3480
             HAAAYTTHPSTLVHQVPVSVGPSLLTSASVAPAQYQHQFATQSYIGSSRGSTIYTGYPLS
Sbjct: 1140 HAAAYTTHPSTLVHQVPVSVGPSLLTSASVAPAQYQHQFATQSYIGSSRGSTIYTGYPLS 1199

Query: 3481 PTKISQYSYL 3510
             PTKISQYSYL
Sbjct: 1200 PTKISQYSYL 1209 (SEQ ID NO:4)
```

Hmmer search results (Pfam):

| Model | Description | Score | E-value | N |
|---|---|---|---|---|
| PF00069 | Eukaryotic protein kinase domain | 188.8 | 8.7e-53 | 1 |
| CE00289 | CE00289 PTK_PDGF_receptor | -78.9 | 6 | 1 |
| CE00287 | CE00287 PTK_Eph_orphan_receptor | -92.1 | 0.023 | 1 |
| CE00016 | CE00016 GSK_glycogen_synthase_kinase | -93.9 | 2.1e-11 | 1 |
| CE00292 | CE00292 PTK_membrane_span | -95.0 | 0.0023 | 1 |
| CE00291 | CE00291 PTK_fgf_receptor | -129.4 | 0.23 | 1 |
| CE00286 | E00286 PTK_EGF_receptor | -138.1 | 0.014 | 1 |
| CE00290 | CE00290 PTK_Trk_family | -145.0 | 2.3e-05 | 1 |

Parsed for domains:

| Model | Domain | seq-f | seq-t | hmm-f | hmm-t | score | E-value |
|---|---|---|---|---|---|---|---|
| CE00289 | 1/1 | 191 | 288 .. | 1 | 109 [] | -78.9 | 6 |
| CE00290 | 1/1 | 191 | 424 .. | 1 | 282 [] | -145.0 | 2.3e-05 |
| CE00292 | 1/1 | 190 | 436 .. | 1 | 288 [] | -95.0 | 0.0023 |
| CE00287 | 1/1 | 190 | 440 .. | 1 | 260 [] | -92.1 | 0.023 |
| CE00291 | 1/1 | 192 | 442 .. | 1 | 285 [] | -129.4 | 0.23 |
| CE00286 | 1/1 | 190 | 477 .. | 1 | 263 [] | -138.1 | 0.014 |
| PF00069 | 1/1 | 190 | 478 .. | 1 | 278 [] | 188.8 | 8.7e-53 |
| CE00016 | 1/1 | 118 | 542 .. | 1 | 433 [] | -93.9 | 2.1e-11 |

FIGURE 2E

```
   1 AAAGTGGGGA GATGTTGGAA GGCAGCAAGC AGATTTTGGA GTGCATTTTA
  51 AGGCAGGTTG AGACAGGTTT TTTTTTTGAG ATAGGATCTA GCTCTGTTGC
 101 CCAGGCTAGA GTGCAATGGA GTAATCACAA CTCACTGTAG CCTCAATGTC
 151 CCAGACTCAG ATGATTTTCC TGCTTCAGCC TCCTGAGTAG CTGGGACCAC
 201 AGGCATGTGC CACTTACACT TGGCTTTTTT TTTTTTTTTT TCCCGGTAGA
 251 GATGGAGTCT CCCCATGTTG CTCTGGCTGG TCTTGAACTC GTGGACTCAA
 301 GTGATCCTTC CACCTTGGGT TCCTAAAGTG CCAGGATTAC AGGCGTGAGC
 351 CACCACATCT GGCCTAATTT TTCTTTTCTT TTCTTTTTTT TTTTTGTTAA
 401 TGCTTCCCAG GCTGATCTTG AACTCCTGAG CTCAAGTGAT CCTCCTGCCT
 451 GGGCCTCCCA AAGTGCGGGA ATTACAGGCT TGAGCGACCA TGGCCAGCCA
 501 AGTTGAGAAT CTTGGACATT ATCTCCAAAG CAATGAGAAA CCCCGGGAGA
 551 AGGGGAAGCA AGATGGTTAA GAAGAGAGAG CAGTTATCTG ATTTGCATTG
 601 TTTAAAAGCA AAGATCTACT GAGTGGATTT AAGGAGATTA GTTTGGAAGC
 651 TACTGGCAGT TTGAACTAGA ATGGTGCCAA TAAGGGTAGG GAAAAAGGGC
 701 TGATTTGAAA TATACTTAGG AGGCCAGGGG CAGTGGCTCA CGCCTGTAAT
 751 CCCAGCACTT TGGGAGGGTG AGGGGGGTGG ATCACTTGAG CTCAGGAGTT
 801 TGAGACCACC CAGGCAACAT GGTGAAAACC CATCTCTACT AAAAATACAA
 851 AGAAATTAAC TGGGTGTGGT CGTGCACGCC TCTACTCTCA GCTACTTGGG
 901 AGGCTGAGGC AGGAGAATTG CTTGAGCCCC AGAGGTGAAG GTTGCAGCGA
 951 GCCAAGATTG CACCATTGCA CTCCAGCTTG GGCTACAGAG TGAGACTCTG
1001 TCTCAAAAAA AAAAAAAAAA AATATACACA CACACACACA CACACACACA
1051 CACACACACA CACACACACT TAGGAGATGG AATGGATAAG ATAGAGATTA
1101 GATGTGGAGG AATAAGGGAG AGGAATGAGC CAGGATAATA GTATTAAATA
1151 TGTGGTAGAC ACTATCATTT TACATGTATT AAATTATTTA ATTCTCAGAA
1201 CAACCCCATG AGGTAGGTAT TGCTATCACC ATTATGTAGC TGAGGAAACA
1251 GACATCCCTA ATTTTTTTTC TTTTTTTTGA GACAGGGTGT CATTCTTTCA
1301 CCCTGGCTGG AGTGCAGTGG CACGATCACA GCTCACTGCA GCCTCTACCT
1351 CTGGGCTCAG GTGATCACTT CTGCCTTCTG AGTAGCTAGG ACTACAGGCA
1401 TGTGCCACCA TGCCTGGCTA ACTTTTTTTT CTGTTTTTTT TTTTTTTTGT
1451 TGTTGTTGTT GTTTGTTTGT TTAGAGACG GTTTCACCAT GTTGCCCAGG
1501 CTGGAGCTCC CTGATTTCTG GCTTGAGGCG TTGGATGTGT GATGGCATCT
1551 CATAATTAAG ATAGAAAACT GAAGGTGGGG TGGAGGCTCG TAAGTTTAAT
1601 TCTGAATGTA TTGAATATGA GGTGTTTGTG AAATGTCCAA GTTGCAGGGT
1651 TAAGTAGTCA TTTGGATATA GGGTTTGGAG TTCAAAGCGA GAGAATCCTG
1701 GGTTAGAGAT AGAGATTTTA GTCTTTTGAA GATGACTAAT TTTGAGGAGT
1751 AATTATTAAA AAGGGGCAAA GGGTAGAGCA AGGAAAGAGG GATTACTATA
1801 GAGCCCCAAG GCATATGAGA TCGGATGGTT GAAAATGGAG AAGATAAATA
1851 TGAAATGGCT TGTGTGCTAT GTCAGATGTT TGGACTTTAT TCTGAAAAAA
1901 TAGCTTTCAG TTTAATCTGT GGGCTTATTG AGCTGGAAGT GTCTGTGGGA
1951 TATTCAGGGA CAGAAAGCTG GACTGTTCTT ACATCCTTTC CTCATATTTT
2001 TCTGCTAACT TTCCTCGGTT CTTCAGAATA TACTCTAGCT TTCTCATCAT
2051 CCTGGTTACT TTTTTTTTTT TTTTTTTCAA TTTTAGTATT TTTAGAGACA
2101 GGGTCTCACT ACATTGCCTA GGCTGGTCTC GAACTCCTCA GCTCAGGAGA
2151 TCTTCCTGCC TTGGCCTCCC AAAGTGCTGG AATTAAAGGC TTGAGCCACT
2201 GTGCCTGGCC CATACTGGTT ACTTTTTTAT CTTAAAATGT GGTAGACAAT
2251 TGAATGCATT TTATGTATGA CCTGAGCAGA GTGGATAATC TTCACTTTGT
2301 CCAGCACGTT CTGTACACTG TTTCTATGAA TATAGGTCAA GATTGAATTA
2351 GTTTTTGAGA AGAGGAGAAC ATTATTACAT CATGTTTCTT TTATCAAGTA
2401 AAAGTGTGTG TGTGTGTTTG TGTGTTTTAA ATCTAAGCCT TGTATCTTTT
2451 ATCCTTGTGG TCTAATTCTT CCTTTCTCTC AATATAGGTA TGGCATCACA
2501 GCTGCAAGTG TTTTCGCCCC CATCAGTGTC GTCGAGTGCC TTCTGCAGTG
2551 CGAAGAAACT GAAAATAGAG CCCTCTGGCT GGGATGTTTC AGGACAGAGT
2601 AGCAACGACA AATATTATAC CCACAGCAAA ACCCTCCCAG CCACACAAGG
2651 GCAAGCCAAC TCCTCTCACC AGGTAGCAAA TTTCAACATC CCTGCTTACG
2701 ACCAGGGCCT CCTCCTCCCA GCTCCTGCAG TGGAGCATAT TGTTGTAACA
2751 GCCGCTGATA GCTCGGGCAG TGCTGCTACA TCAACCTTCC AAAGCAGCCA
2801 GACCCTGACT CACAGAAGCA ACGTTTCTTT GCTTGAGCCA TATCAAAAAT
2851 GTGGATTGAA ACGAAAAAGT GAGGAAGTTG ACAGCAACGG TAGTGTGCAG
```

FIGURE 3A

```
2901 ATCATAGAAG AACATCCCCC TCTCATGCTG CAAAACAGGA CTGTGGTGGG
2951 TGCTGCTGCC ACAACCACCA CTGTGACCAC AAAGAGTAGC AGTTCCAGCG
3001 GAGAAGGGGA TTACCAGCTG GTCCAGCATG AGATCCTTTG CTCTATGACC
3051 AATAGCTATG AAGTCTTGGA GTTCCTAGGC CGGGGGACAT TTGGACAGGT
3101 GGCTAAGTGC TGGAAGAGGA GCACCAAGGA AATTGTGGCT ATTAAAATCT
3151 TGAAGAACCA CCCCTCCTAT GCCAGACAAG GACAGATTGA AGTGAGCATC
3201 CTTTCCCGCC TAAGCAGTGA AAATGCTGAT GAGTATAATT TTGTCCGTTC
3251 ATACGAGTGC TTTCAGCATA AGAATCACAC CTGCCTTGTT TTTGAAATGT
3301 TGGAGCAGAA CTTATATGAT TTTCTAAAGC AAAACAAATT TAGCCCACTG
3351 CCACTCAAGT ACATCAGACC AATCTTGCAG CAGGTGGCCA CAGCCTTGAT
3401 GAAGCTCAAG AGTCTTGGTC TGATCCACGC TGACCTTAAG CCTGAAAACA
3451 TCATGCTGGT TGATCCAGTT CGCCAGCCCT ACCGAGTGAA GGTCATTGAC
3501 TTTGGTTCTG CTAGTCACGT TTCCAAAGCT GTGTGCTCAA CCTACTTACA
3551 GTCACGTTAC TACAGGCAAG TGGCAAATGC TGAAAATCGT ATCTTAGGCT
3601 AGAGTTCTGT CCTTATATTT AACATATACC CCGTAGGCTA CATATAGCAA
3651 TGAATTTGTT TATAGATTCT GAGATAGAAA TAGGATATGT TTTAGCTCAT
3701 TCTATGTGTG TGGCATTCCT ATATATGACA TTTATTTCTG AAATTTTATC
3751 TAGCACTGGA AAAATTAACT CAGTCTGATT CTGAAAGTTG TTACTAGTTG
3801 AATTATACTA GCACCTGGTT CTTTAGTATT ATTTTACCTC ATTTTCCCAT
3851 TTTATTTATT TTATTTATTT ATTTATTTAT TTAGAGACAG AATCTCGCTC
3901 TGTCGCCCAG GCTGGAGTGC AGTGGCGTGA TATCAGCTCA CTGCAAGCCC
3951 CACCTCCTGG GTTCACGCCA TTCTCCTGCC TCAGCCTCCT GAGTAGCTGG
4001 GACCACAGGC ACCCGCCATC ACGCCCGGCT AATTTTTTTT GTATTTTTAG
4051 TAGAGACGGG GTTTCACCGT GTTAGCCAGG ATGGTCTCGA TATCCTGACC
4101 TCGTGATCCA CCCGTCTCGG CCTCCCAAAG CGCTGGGATT ACAGGCGTGA
4151 GCCACCGTGC CCAGCCTATT TATTTATTTT TTTAAGATGG AGTTTCACTT
4201 GCCACCCAGG CTAGAGTGCA GTGGTGTGAC ATTGACTCAC GGCAGCCTCC
4251 ACCTCCTGGG GTCAAGTGAT TTCTCCTGCA ACTCCTGTCC TGAGTAGCTG
4301 GGACTACAGG CACCTGCTAC CACGCCCGGC TAATTTTTTT GTTTTTAATA
4351 GAGATGGGGT TTCACCATGT TGACCGGGCT GGTTTTGAAC TCCTGACCTC
4401 AGGTGATCCA CCCGCCTCAG CCTCCCAAAG TGATTAGAGG CGTGAGCCAC
4451 CATGCCCAGC CATTTTCCCA TTTTGAAGAG TCTTGAAATA CACAAAGATA
4501 TTTACTTATT TGTAATGAAT CTGAGCATAT GTTGCTGTTT TTTCGAACCT
4551 CTTATCTTGG CAGGTAAAAT AACGTGGGAA TAACTCTAGG TTTAACTCTA
4601 GTAACATTTT ATTCTTTTAC ATTTTCTTCT GTAGTAGCAT GAATTGAATT
4651 ACATGGTTGC TACAATCTCT TCCTGTTTTA ACTTTCTCTA AATACTTTGA
4701 ACTTAATGGG TTATCCTAGA ATGGCTTTGA CCCAAGTACC TTATACTTTA
4751 ATGATATATA TTTCTAGATT GATACTTTTA ATGTAGCTAC CATTTTAATA
4801 TATAATAATT ATTGGGACAG TATGTAAATG CTGATATATA CAATTTTGTC
4851 TGTACCATAA CCAAGGCTTT TAAAATGTGC TTTTTATCAG CACCCATTTA
4901 CTTACTTGCC TAGTTATTAA TTTTAAGGAA TCTAATATTT AGTTTAATG
4951 GCCATACATT AAATACAAAT CATGTAAGCA TCCAATCAAG AAGTGAAATA
5001 ATAAAAACAT AGATAACCTA TAAAATATGT TTATAAGGAG CTATACATGC
5051 CAGATGCCTG TAATAAAATT TGAGGAAATA GAAATTCTGA ATTAAGAATT
5101 TTATATTATG TGTGAAAATA ATGTGAGGAT ATTTTAACCC ATACAAGGAC
5151 TCAGAAAAAA TGTCATCTGC ATGTTTCCTT TTTTAAAAAC ATTGTGGTAA
5201 GATGTTTATA ATAGGAAATT TACAATTTTA ACCATTTGGT ACCACTCATT
5251 GTGTTAAGTA CATTCATAGT GTTGTGTAAC CATCACTGCT GTCTGTTAAG
5301 TATATTCACA ATGTTGTGTA ACCATCACCA CTATTTCCAA ATGTTTTCAT
5351 CACCCAAAAC AGAAATTCTA ACCATTAAGC AATAACTCCC TATTCTCTCT
5401 TCTTCCTACC ACTGGTAATC TTGATTTGAC TTTCTGTCTC TATGAATTTG
5451 CCTATTCTAG ATACTGCATG TAAGTGGAAT CATACAATAT TTGTCTTTTT
5501 GTGTCTAGTT TATTTCACTT AGTGTAATGC TTTTGAGGCT AATCCATGCT
5551 GTAACATGTA TCAGAACTTC ATTCCTTTTA TGGCTGTATA ATATTCCATT
5601 GTTTGTATAT ACCACATTTT GTTTATGCAT TCATCTGTTG GTAGATATTT
5651 GGGTTGTTGC TACCTTTAGG CTGTTGTGAA TAATGCTGCT ATGAACATTG
5701 GTGTACAAGT ATCCTAGTCC CTATTTTCAG TTACTTTGGG GATATAGCTA
5751 GGAGGGAATT GCTGGGTCAC ATGATAATTC TATGTTTAAC TTTTTGCAGA
```

FIGURE 3B

```
5801 ATTACCAAAT TATTTTCCAC AGAGGCTGCA CTATTTTACA TTCCTACCAG
5851 CAGTGGATGT GCATTCCAAA TTTCTCCACA TTTTCTCTAA CATTTGTTAT
5901 TTTTTTTATT TAAAAATATT GTTTGTTTAT TTTTACAGAG ACAGGGGCTG
5951 CCTCTATTGC TCATGCTGGA GTACAGTGGC ACGATCATAG TTCACTGTAG
6001 CCTCCAACTC CTGGACTTGA GCAGTCCTCC CACTTCAGCC TCCCAAGTAG
6051 CTAGGACTGC AGTCACACTC CACCATACCT GGCTAATTAC TATTATTTTA
6101 TTTTTTGTGG CGACAGTGTT TTGAGGGTCT CATTTGTTG CCCAATCTGG
6151 TCTCAAACTA CTGGCCTCAA GCCATCCTCC TGCCTCAGTC TCCCAAAGTT
6201 CTGGGATTAC AGGTGTGAAC TACCACTCCT GGCCTTGTTT TGTTTTTTAA
6251 ATAATAGCCA TGGGTTTTTT TTTTTTTTT TTTTTTTTT TTTTTTTGG
6301 AAAGGGAGTT TCACTTTTGT TGCCTAGGCT GGAGGGCAGG GGGGCAATCT
6351 CGGTTAACTG GAACCTTTGC CTCCCAGGAT TTTCCTGCCT AAACCTCCCA
6401 AGTAGCTGGG ATTACAGGGG CCTGCCACCA CACCCAGTTA ATTTTTGTTT
6451 TTTTAAAAAA AATGGGGTTT TACCATGTTG GCCAGGGGGG GCTCCAACTC
6501 CTGACCTCAG GGGATCTGCC CACCTTGGCC TCCCAAAGTG CTGGGATTAC
6551 AGGCATGAGC CACTATGCCT GGCCAATAAT AGTTTTTTTT TGTTTTTTTT
6601 TTGTTTTTTT TTTGAGATGG AGTCTTGCTC TGTTGCCAGG CTGGAGTGCA
6651 GTGGCACAAT CTCGGTTCAC TGCAACCTCC ACCTCACAGG TTCAAGCAGT
6701 TCTCCTAGCT TGGCCTCCTG AGTAGCTGGG AATACAGGTG CCACCATGCC
6751 CAGCTAATTT TTGTATTTTT AGTAGAGACA GGGTTTCACC ATGTTGGCCG
6801 GGATGGTCTC GATCTCTTGA CCTCGTGATG AAGTGCTGGG ATTACAGGCA
6851 TGAGCCACCG GGCCCGGTCA ATAATAGCCA TTCTTATGGG TGTGAAGTGG
6901 TATCTCATTG TGGTTTTGAT TTGTATTTCC CTAATGATTA ATGATGTTGA
6951 GCATTTGTTT TATTTTGTTT GTTTGAGACA GAGTCCCACT TTGTCACCCA
7001 GGCTGGGGTG CAGTTGTGCA ATCATGGCTT ACTGCAGCCA TGACCTCTCA
7051 GGCTCAAGCA GTCCTCCCAC CTTAGCCTTT CGGGTACCTG AGACTACGGG
7101 CATGCACCCC CACACCTGAC TAGTGTTTTG TATTTTTAGT AGAGACGGGG
7151 TTTCACTGTG TTGCCCAGGC TGGTCTCAAA CTCATAGGCT CAAGTGATAT
7201 GCCCGCCTCG GCAACCCAAA GTGCTGGGAT TACAGACATG AGCCACCATG
7251 CCCAGCCTGG CATTTTTTTA TGTGCCCGAC ATCTGTATAT CTTCTTTGGA
7301 GAAATGTCTA TTTAAGTCCT TTCCTCATTT CTTGAATTGG GCTTTTTGTT
7351 GTTGAGTTGT ATACTCTATA TACTTAATTT TCATCTATTC CTTGGGTTGC
7401 CTTTTTACCT GTTGATAGTG TTTGACACAG AAAAGTTTTT AACTTTGGTG
7451 AAGTGCAGTT TGTCTACTTT TTCTTTGGTT GCTTGTGCTT TTGGTGACAT
7501 ATCCAAGAAG TCACTGTTAA GTCGAAATCA TACAGATTTT CCCCTATGTT
7551 TTCTGCTAAG AGTTTTATAG TTTTAGCTCT TATATTTTGG TCTTTGATTC
7601 TTTGTTGATT TTTGTCTATG GTCCAAGGTA CAAATCCAGT GTAATTCTTT
7651 GGCATGTGAC TATTCAGTTC TTCAAACACC ATTTGCTAAG AAGATTGTCC
7701 TTTCTGCATT GGGTGGTTTG GGCACCCTTG TTGGAATCAT TTGAACATAT
7751 ATACAAATAA TTCTTATCTT CTATTGCTTT CCCATTTTCA ATGTTGGGCT
7801 CTCTATTCCA TTAATCTATA TATGTCTTTA TGCCAGTACC ACATTGTTTT
7851 GATTATTGTA GCTTTGTAGT AAGTTTGAAA TCAGGAAGTG TGAGACCTCC
7901 AACTTTGTTC TTTTTCAAGA TTGTTTTGGC TATTTGGGGT CTTTGAGGGT
7951 CCATATAAAT TTTAGGATGG GTTTTTCTAT TTTATACAAA AACCATAATT
8001 GCTTTTTATT AAGGATAGCG ATGAATCTGT AGATGACTTT GGGTAGTATT
8051 GACAGCTTAA TAGTAAGTCA GTCCATCCTT ATTTCTTTAT ATCTTTTCAC
8101 AGTTTTATAA AACTGGTATT TTTTACTTGA GGTAAGGTAA ATAAACTCTT
8151 AGAGCCTTTG TTTTCTGGTT TTATGCTGCC CTAGGCAACC TTGGCTAACT
8201 TTAAGAATGT CATCTCCATT TATTTATTTA TGCCTTGGGA GATTTAGGTT
8251 CCAACTACAT TTGCTTTTTA ATGCTCTCCT TTGAGCAGTC TCACCACCAG
8301 CCACACCAAC ATAACATATA TATAACATAC TCTACAGGTG CACTGAAGAA
8351 TTCAGCGCAG CATCCCATTT TGAGTCCTCA GGAGGGACTA GGCAGACCAC
8401 AGCTGAAGGA AGAGGGCTGA TCAGCTCTTC CTTTCTGTCT TGACTCTGTG
8451 CCTGCAGGTG TTCTTTAACT ATTTGTTTGC CCTGTCAAAG ACAAAGTGCA
8501 TTCTCTTGTG ATACCAGAGT AGTTTTTAAA TTGAAAAAGG GAGAGCAATA
8551 GGAGATAAAA ATTATTTGGC TTTGTTATAA TTGGGGCATG TTAATACAAA
8601 ATAAAATGAA TTATTTGGCT GCTTAGCTTT CTGTAATGTG TAATTCATTT
8651 GAATAATTTT CAGTGTTAGG TTGCTGATCT TTGTATTTTT TATCCTTTTA
```

FIGURE 3C

```
 8701 ATTTAAGCTG TCAATTGATT CATTTTGGTT TTGTTTTTTA TAGAAACTAA
 8751 GGTTTTCAAA TCTTCAAAGT TACCCTTCGA CAAAGCTTTC TTTAAATTCA
 8801 CTGCAATATA GTTGTTGACT ATAATTTTAA GTGGAGCTAA GTTTGCCTCT
 8851 TAAAAACAGG AGTTCATTCT GTGTATTACT GAGTAATTAC TCTGTATACT
 8901 GAAGTTCAGT GCCCAGGGCT TGACAGTGTT TAGGATTTAA CATGAGTGTT
 8951 CTGTTGTGTC ACAGTAATAC TTGATAATGA GCCTAAGGCA GATGGAACAG
 9001 CAGCTCAGGC ATTCCTTCTT TATCACTAGT TTTACCCGCA GTGGTCCTCT
 9051 TAAGCTTCTT TGATGTTGCT TTGTTGCCAT ATTAGAGTCC ATTAAGTCCT
 9101 CACCCTTCTG TCTTTCAAAA AACCTCTGTG AAATCTGTTT GGCTGGTGAA
 9151 GCATTTTGAC TCCAAAGCTA GTCCTTCTCT TACCCACCTT TTTAGTTTAC
 9201 CTTGCTTTGT CTTTCTGATA ATATGCCAGT ATTATCAGCT CACATAAATT
 9251 TGCCACCTTG CTGTGTCCAT TGGCCCTGGG CATGGCTAAA TGATTCAGGC
 9301 AGTGGAAATA ATATACTTTA CTCTCTGGCT CACTGTAAAT GTGCACAGAC
 9351 TCCAAGCAAA GCTCCTGTCT TTCGGGCTTG AGTTTTAGAG ACAAAGGTTT
 9401 GCCATGCTTA CAGGCTGAAT GTTTTTCCCT ACTGAACAAA CTAGCCAGCC
 9451 TTTATTTCAA GCTGAATCAC TTTGTTACTT ACGGAAGGAA AAGGTCTAGA
 9501 GAAGGAAAAC GTATCTTCCA TTTATCCTAG ACAAACAAAT AATCTAATTT
 9551 CCTCTGGCAG TCAAAATATA GTTTCACCTA AGCCACTGAT GCAGGAAGTT
 9601 AGGTTTTATG TAACCTCTCT AATTGGTAAG TAAGTAGGTT TGATGTCTCT
 9651 GAGATAGGAA GAAAGAAACG AAAATGTTCA TGAAAATAAT CAGAGTGATT
 9701 TGTGTTAAGT GATCCTAACC TTAGCTTGCT CTGGGTGCCA GTGAAATTAA
 9751 CCTCAACAAT GTTGGTTGGA AGAATTTTTC AACTTAAAGA AGTTTGAAGT
 9801 TGGGGAATCA AAAGGCAGGG ATTGTTGTTT CTATCACTTA GCTGTAATAA
 9851 CCAGAGCCTG TTTAGTATTT GTTTTTTAAG GATGGGATGT GTCTTCAAAG
 9901 AGGAGACTTG CCATGTTCAA AGCACAATTA ATGCCATTTT CCTACTGAAG
 9951 TGAACACTGC CAGTTTTTAA CAGTTTCTTT CACTTTCCTG TGCTTCTGTA
10001 GATAACCTTT TTTACTGCCC AGTTGTTGGA ATGTTACAGC TGGAAAGGGA
10051 CCTAGAAGAG TAATTATCTA ACTCTGTTTC CTTATTACAC AAATGAGGTA
10101 GAACCAGAGT TTTACGTGTC TATAGAGTNN NNNNNNNNNN NNNNNNNNNN
10151 NNNNNNNNNN NNNNNNNNNN NNNNNNNNCA GTGGCGCAAT CATGGCTCAC
10201 TGCAGCCTTG ACCTCCTGGG CTCAAGTGAT CCTTCCACCT CAGCTTCCTG
10251 AGTAGCTAGA ACTGCAGGCA TGCACCACCA TACCTGGCTA ATTTTTTAAA
10301 TTTTTTTGGT AGAGATTGGG TCTTGCTGTG TTGCCTAGGC TGGTCTCAAA
10351 CTCCTGCTCA AGTGATCCTC CTGCCTTGGC TTCCCAAAGT GCTGGGATTA
10401 TAGGTGTGAA CCGCCGTTTC TGGCCGTATT TTTTTTTTTT TTAAACTGCT
10451 TTCCTTTTTT TGTTTTTCCT TTTGCTATTT GCCTTTTTAT AAGGTAGATA
10501 CGGTAGAGTT GCTGTTTTGA CTGAGCTTTT GCTGGAAGTC CTTAGCTGCT
10551 TTTGTCACTC CAAAAGCAGG GTGAGACCAA ATGAAAAAAC TTTCAGCTAA
10601 TCTTCAGTTT TTTTTTTTAA TTAAATGGGA CTTGGGGGCT GTGGAAGTGA
10651 TATTTTCCTT AATTTCCCAG AAAACTTTAA GCTCGAGACA GTTATCATAT
10701 ATTATTGCTA CCTTTTTTAT TTTTTTCTGA GACGGAGTTT CGCTCTTACG
10751 CCCAGTCTGG AGTGAATTGA CGTAATCTTG GCTCACTGCA ACCTCTGCCC
10801 CCCGGGTTCA AGCGATTCTC CTGCCTCAGC CTCTGGAGTA GTTGGGATTA
10851 CAGGCGCCTG CCACCATGCC CAGCTAATTT TTGTATTTTT AGTAGAGACT
10901 GGGTTTCATC ATGTTGGCCA GGCTGGACTT GAACTCCTGA CCTCAGGCCA
10951 TCCACGTGCC TTGGCCACCC ACAGTGCTAG GATTATAGGC GTGAGCCACC
11001 GCGCCTGGCC TGTTATCGCT ACCTTTTAAA GAAGAAAGTT ATAGAGTGGC
11051 CTGGCCATTC TCTGTGACCT ACCTTTTGGA CTTTAAAATG TCTTTCTAGT
11101 ATGGTAGGAA TAGCAAAATC AATATGCTGC CCTCCAATTG ATGCTTTGGA
11151 ATGTTCTAAA CCCAGTTTTT ATTTTGGCTC ATTGCCAGTT GTGCTCCCCC
11201 TGCCAGCTAT TTTTGGCATT GTCATGAACT TGGAAATTAA TGATTCTGCT
11251 CACTAGGAGT AGAAAATTTT GTTCCTTTTC AATTTTAGAA AAGCTTTTAT
11301 GTTGTTTCTG GGTAGTCTTA CTAGCTTATT AATGCGCCTG TCAAACTTGT
11351 GCAGTGTTGA AAACATGCCA TTATGGTTGA GATTTCACTG AACTCTGAAA
11401 TTCCATCAGT AATATGTGCC TCTAGCCACC TGCAACAGGA ATATCACTTT
11451 TGAGGGTTAC TTCTTTTCTT TTCTTTTTTT TTTTTTTTTG AGACAGAGTC
11501 TTACTCTGTC ACCCAGGCTG GAGTGCAGTG GCACTGTGTC AGCTCACTGC
11551 AACCTCCGTC TCCTGGGTTC AAGCAATTCT CCTGCCTCAG CCTCCTGAGT
```

FIGURE 3D

```
11601 AGCTGGGATT ACAGGTGCCC GCCACCACAC CTGGCTGATT TTTTATATTT
11651 TTAGTAGAGA TGGGGTTTCA CCATGTTGGC CAGGCTGGTC TCAAACTCCT
11701 GACTTCAGGT GATCCAGCCT CCTCGGCCTC CCAAAGTGCT TGTATTACAG
11751 GCATGAGCCA CCGCACCCGG CCAGTTATTT CTTTGGTAAA CAAAACCACA
11801 GTTCAAATTA AATACTACAA AAACTGATGA TATTGGTGGT TCCACCCATA
11851 GCTGTTAAAA AGTGTAAGCC CGAAGAGGCC TGGGTCGACT GCTATTTGTA
11901 TTTAAGGATC AGAAAAGCTT TCAGGCCCTG TGGAGTCCCC AGATTTACTG
11951 TTTTCTAAGG GCCACTATTT ATGTATAAAT ACTAGGGGAG GATTTTTTTT
12001 TTCTTCTATG CCTAGTTTGC TTAGATGGGG AGGGATATTC TTATTTAGGG
12051 AAATTATATT CTCCTTGCTT AATCCTTGCC TTCCCTCAAC CCCCTGCACA
12101 TATACACAAA ACAACAATAA GCACATATCA CTTGAAAGTA GTTTGAGAAA
12151 CCTGGGTATT CTGTGAGGAG ACACGGCCAG TTAGATGGTT CTTCACGGAA
12201 AGATCTGTTT TCCATTTAAC TCCTGTAACA TGAGGAATCT GAATCTGGAT
12251 CTGGATCTGG ATCTGGAGTG TCCTTATAGA TTATAATTCC ATGACTTGTA
12301 AGAAAGAAAG GAAATTATTT GGAGAAGATG ATCCAGTGCC TAAGAGCTGA
12351 AATCTTGGAT CCAAATAGCT TGGGTACCAT CCTTTTTCTT TTGTTGAGAT
12401 GGAGTCTCGC TCTGTCGCCC AGGCTGGAGT GCAGTGGCAG ATCTCAACTC
12451 ATTGCAACTT ATGCCTCCCA AGTTAAGTA ATTCTCTTGC CTCAGCCTCT
12501 GAGTAGTTGG GATTACAGCT GCCCGCCACC ATGCCCAGCT AATTTTTGTA
12551 TTTTTAGTAG AGATGGAGTT TCACCGTGTT GACCAGGCTG TTCTCGAACT
12601 CGTGACCTCA AGCAATCCAC TCACCTTGGC TTCCCAAAGT GCTGGGATTA
12651 CAGGTGTGAG CCACTGCGCT GGCCAAGGGC ACCATCTTTT AGTAGTTATG
12701 TAGCCTTGGG CAAGTTACTT TAACCTCTTA GTGCCAGTTT CTTCATCTGT
12751 AAAATGGAGG TAATACTTTT ATTGCATAGA ATCTAACATG CCATTGATTA
12801 TAAGATACAT TATTTTTGTA CCACTTAAAA AAGGAAAAGC GCTGCCATTA
12851 AACTAAAATA TACCATCATT TGTAAGAATC TTCTTAATTT CAGAGGTGCT
12901 AACATGTAAA AAGATGTGTA TCTTAGAATT GATGACATCA TAATAATACT
12951 TTGATAGGAT TGTTGTAAGG ATTAAGTGAC TCAACATTTA TAAAGAACTT
13001 AGAACAGTGC ATGGCACATA GTAGGCAATA TTTATGTGTC ATTTATTATT
13051 ATTGCTATTA GTGTTACCTA TTATTTTCTT TTTGAACCCA CTTATTGCCT
13101 AATTAGTCAT AGTTTGACAA TTGCCCTTGT ATTCCACCAT GTCAAATATA
13151 AATTTACATA GATGAGTATG TACTTTTACT TATTGAGAAA CAGTGTAATA
13201 TATAATATAC TCAATTCTGG AGCCAGATTG CAGGGATTCA AATCCTAGCT
13251 CTGCCACTTA TTTGACTGTG ACTCTAGGCC AATAACTTAA TCTTTCTTTT
13301 TCTCAGTTTC TTCTTCTGTA ATGGGGATAA TAATTCTATT TTAGATGTGT
13351 TCGTATATAT AAACGTCTGA GTTATGGATT ACCTTAGTCA TCTCTTTAAA
13401 GTTCCCTAGC ATTTTATTTC TCACTTGGAC TGTTAATGAA TATTTCTAAA
13451 AAGCACACTA AGAGTTCAAA GTTTTAAAAT AATGGTAACA TAATACTGTT
13501 ATTATATCTA ACACCTACTA GTATTTACCA TGTGCCATGC ACTGGTCTAA
13551 AAGCTTTCAT ATATTTATTT AAGCTTCACA ACAACTCTAT GTGGTGGGAA
13601 CTCTTACTGT CTCCATTTTA TAGATGAGGA ACCTGAGGCA CAGAGAGATC
13651 AAGTAATATA CCTGCAGCTA TTAAATGATG GAACTAGGAT TCAGACCCTG
13701 ACAGGCTGGC TCTAGAGAGT GTGCTGTCAA CACCATGTCT CTTCAGAAGG
13751 CATTTCTTTT TCTTTTTTTT TTTTCCAGAA GGCATTTCTG TCATGAAGGG
13801 GTTATTTATT GACCAGGGCT TTTTTTTTTT TTTTTGGACT GTCTTGGGTC
13851 TCCTAGGCTG GAGTGTAGTG GTGTGATCTT GGCTTACTGC AACCTCTACC
13901 TCCTGGGTTC AAGCGATTCT TTTGTCTCAA CCTCCTGAGT AGCTGGGATT
13951 ACAGGCGCCC ACCACCACAC CTGACTCATT TTTGTATTTT TAGTAGATTT
14001 GGGGTTTCAC CATATTGGCC AAGCTGGTCT TGAACTTCTG ACCTCAGGTG
14051 ATCCACCCGC TTCGGCTTCC CAAAGTGCTG GGATTACAGG CATGAGCCAC
14101 TGTGCCCAGT TGACCAGGCC TTTTAATTGA TTTTTTTTTT TTATGATTGA
14151 AATGGTGCTA GGAATAATAA TAAAAAAAAT CTATTATCCC TTATCTGTGA
14201 TTGCAAAATT CAGAAAGCTC TCATAAATGA AAATTTTTCT TTAAGTTTGG
14251 TATAAATTCA TTTAATTGGC AAGACCTGAC TTGAACCATT GTTAAGCTAT
14301 TTGAAGTCTT TATTTAGCCA ACTTAGTATG ACTGTTCCCA TGTTTTGTTG
14351 CAGAAATATT AATGTGTTTG ATTATAGTGC ACTGCCCTGA ACTCCACTGG
14401 GATTATTATA TAATGTGTAC TTGTGTTCT GCATTACCTT TCTGAAATTC
14451 AAAATATTCT GAATTCCAAA ACACATCTGG CCCTGAGCTT CAGATGATGG
```

FIGURE 3E

```
14501 ATTGTATACC AAAGATTTTT TTTCCATTTC ATTGAATAAA TGTTCCTTTA
14551 GCTAATACTA AAACAGGACT TAGTCATGTA GTTAATTTTC CCAAATAATG
14601 TTTTTTTTTT TTTAATCTGA TATTTTTTGT TTTTGCTAGA GCTCCTGAAA
14651 TTATTCTTGG GTTACCATTT TGTGAAGCTA TTGATATGTG GTCACTGGGC
14701 TGTGTGATAG CTGAGCTGTT CCTGGGATGG CCTCTTTATC CTGGTGCTTC
14751 AGAATATGAT CAGGTAAAAG TGTTTATTTG AATGGAAATA GAATGCAAAT
14801 AGTTACTTGT GAATTAGATT CTGGAGAAAG AGAAGTACTA AGTACTACTG
14851 AAGTATTTAG ATAATAGGGA AAGAGTAGTC CAATTGCTAC TAAAGAACTT
14901 TTTAAAGAAT AGTATAATTT TCTCTTCCTG CTTCTTAGGC TAAAGTATGT
14951 TTGCAATTCT ATAATAAAAA AAAGAATTTT ATTTTATATT AAGGTTGATA
15001 CTTTGCTAGA TCTGTAATGA TTTATTAGAG ACTTAACTTT CATTAACTTA
15051 TGTGCTTTGT GAGTTAGGAA AGTAGAGTAA AGATGAGGAA CTGGAATTTT
15101 AAAAGAGAAC TTCTACTTAC TCGGAGCTAT TATAATTTAC TTTTACGCAT
15151 GACACACTGA AGTACTTTCT TCAGACTGAA ACACTTCAGG TCCCAGAAGC
15201 TGTGACATAC TGGGTCGCTA AGATAGGATT TAGAAAGGAA ATCATCCTGA
15251 GTTGTAGTAA TATATGATCT GTATCTAAAA ATAGACAAAC TTAGGAGATA
15301 TGGTATAATT TCCTAAGGAA TTGGTCCGTT AAGGGAAAAT GTTTTACTAT
15351 GGAAGTAAAT TGTGAATTCT CATTTCTTGT TATTTTTTCT TTTTTCTTTT
15401 TATTTGTTTG AGATGGAGTC TTGCTCTGTC ACCCAGGCTG GAGTGCAGTG
15451 GCGCGATCTC GGCTCACTGC AACCTCTGCC TCCCTGGTTC AAGCGATTCT
15501 CCTGCCTCAG CCTCCTGAGT AGCTGGGATT ACAGGTGCCT GCCACCATGA
15551 CCAACTAATT TTTGTATTTT TTAGTAGAGA CGGGGTTTCA CCATGTTGGC
15601 CAGGCTGGTT TCGAACTCCT GACTTCAGGT GATCCACCTG CCTCAGCCTC
15651 CCAAAGTGTT GGGATTACAG GTGTGAGTCA CCGTGCCTGG CCTTCTTCTT
15701 ATTTTTTAAA AATGTTCCTG CCCTTTATGA TGTAAGCTCC TTGAGGGTAG
15751 AGATTGTTTC ACATCACCAG TGTATCCTCA GCTCCTAACA CTGTGTCTGG
15801 TACACAGTAA GTACACCAGT TTTTTGTTG TGGTTTTTAA GTTTTTATTT
15851 TTTTAGAGAC AGAGTCTTGC TCAGTCACCC AGGCTGGCAT GTAGGCCTGT
15901 CACAGCTTAC TGTAACCTCT AGCTCCTGGG CTTAAGTGAT CCTCCCACCT
15951 CAGCCTCCCA GGTAGATGGG ACTATAGGTG CATGCCACCT TGCCTAGCTA
16001 ATTCTTTTAT TTTTTGTAGA GTCGGGGATC TTGCTATATC AGCCTAGGGT
16051 GGTCTCAAAC TCCCAGGCTC AAGCTATCCT CCTACCTTGG CCTCCCAAAG
16101 TACTGGGATT ACAGGTGTGA GCCACCATGC CTGGCCTATA TTGTCAAATA
16151 TCTTTACTTG TCCGTAAATA CACTTCTACC TTGTCATTTA CAATGTCTGC
16201 ATGGTATTTT GGTTTCCAGC TACAGGATTT AGAAAGGAAG TTATCTGAGT
16251 TGTAGTAGAT TCCACAGATT TGAAGTATTA GAAGTCAACA GGAAAAGCAA
16301 AAAAGATTAT AGCCAAAATT TTCAAAACTG GATTTCCTTG TAAATAATAG
16351 ATACAGTAGC TGTGGATGGA TTAGTATATA TAGGTATTTA CAGATAAATT
16401 TCAGTTGTAT TGATTAAAGA TTTGATTTCT TCCTTTGCCT AAAGTTAATG
16451 ATGTTTTAGT GTAAAAGCCT TTAATAATTT CCCTTTTCAC TCCAAATAGT
16501 TGTTTGATGG TTTTGATGTT TCAGATTCGT TATATTTCAC AAACACAAGG
16551 CTTGCCAGCT GAATATCTTA TCAGTGCCGG AACAAAAACA ACCAGGTTTT
16601 TCAACAGAGA TCCTAATTTG GGGTACCCAC TGTGGAGGCT TAAGGTCTGT
16651 CTTCCCTACT ATGCTTCCGA CTCCTGTACT CCACCCCTCA CTCCCCAATT
16701 TTGAATTCAA AGTTTAGTTA TTAAATTCTT CAGGTAGAGA AGGGAAAGGA
16751 GAGGGGGAAG CATTTTGAAA AATTATTTCT TTGTACCTGT TTGGCCTTAT
16801 CCTCAGTTGA AAAACAAAC ATTAATTGCT AGTTCAGTTG GCTGAGGTTA
16851 TTTTGTATAT GTTCAATCCA CAGCTGATAG AAAGTTTGGA GGGTAGTGCT
16901 CACCATTAAG CGATAGAACT AGAGACATAT AGTAATGACT GATTTTTAGA
16951 GAATTCTCAA TGAACATGAT AAAATCACAA ATTTTCTAAC TGCCCACATT
17001 CAGGACTTCT ATATTTTTTC TTGAAACAAA TACCTGCTTT TTACTTCTGA
17051 GCCTACTCTG TCAGGTTCAG AAATATCTGA GTAATTTGAC TAACCCTGTG
17101 ACTGTGTGTC TGAGTCTGTT GAACAGTTAG CATTTGAGAT ATCGATTTAT
17151 TTGAAAGTAG CTTTAAGAGA ACAATGGTAG TGTCCCCTTT TACCTGACAT
17201 TCTTTAGGAA CTGTGCTGTA TCATTACTTG CATGTTTATC ACTGTTGAAA
17251 GGGTAGCTAG ATATCAAGGT CACATCTCTC CACTGGAAGA TTTTCTGGTT
17301 GTGAATTACT TTCATGTTTG CCATCTATGG TTGGCAAGGT GACCACACTT
17351 GTCTCTTGTA TTCTGGCTTT GGTTTTGAAT AAAATGTGAA AATAACATAC
```

FIGURE 3F

```
17401 AGATGGAATT TAAGGAGGAA AATCTTTATT TTATAGACAC CTGAAGAACA
17451 TGAACTGGAG ACTGGAATAA AATCAAAAGA AGCTCGGAAG TACATTTTTA
17501 ATTGCTTAGA TGACATGGCT CAGGTGAGTA CGGAAAGTTT CAGAAAGTCA
17551 GACATTTATT TTTAATCAGA GACACTTCTG TTGATTATAC TAAAGACAAA
17601 TTTAATGTTA TCTTTCTAGT ATTTGTTTTC AGTTTTTATA AAAAATGCAT
17651 TAATATTCCA CCATGTAGTA AAGGAACATT TAAATCCTAA CCAAGTATAT
17701 TTTTAGAATT ACATATTTCT CTCTTGCTTT ACTTGTCTTG TTACATAGCA
17751 GTGTTTTAAA ATATTACTTA TGAAAGTTTC TTGTCCCATT TTCTCTATTA
17801 AATACTTAAG AATTATATTT ATTGAGCGCC TATTATGTTA CGAACTCTGA
17851 ACACTTCACA CTTATGTCAT TTAATTTTTT CAACAGTAGA AGCTTTTATA
17901 TTTAGGTAGT AACAATCACT ATTGCTTAGC TACTTGTTCC ATTTTTTTTT
17951 TTTTTTTTTT TTTTTTTGAG ACAGAGTCTC ACTCTATTGC CCAGGCTGGA
18001 GTGCAGTGGC GTAATCTCAG CTCACTGCAA CCTCTGCCTC CCGGGTTCAA
18051 GCGATTCTCC TGCCTCAGCC TCCCAAGTAG CTGGGATTAC AGGCACGTGC
18101 CACCATGCCC GGCTAATTTT TGTATTTTTT TTAGTAGAGA CGGGGTTTTG
18151 CCATGTTGGC CAGGCTGGGT CTCAAACTCC TGACCTCAGG TGATCCACCT
18201 GCCTTGGCTT CCCAAAATGC TGGGATTACA GGCATGAGCC ACCGCGCCCA
18251 GCCCCCAAAT TTTTAATGAC AAGAAATTGT TTAGCTTTCT TCTACCACTC
18301 AATTTAGATG AAGATTTTAA TTAAACAGCA TAAAAAGAGC TTCCTCCTCT
18351 GAAAATGATT AGATTTTCAT AAAAAGAATT TCCCCAGGTT TCTCTTTTGA
18401 TTACATATAT ACACACACAC ATAGTTTGGA GGGAAAGCAG CTATGTAGTG
18451 TCAGTGCCAA AGGTTAAGTG AAGAAGTATA ATTCTGAATT TTCTTTGGAA
18501 GGTGAATATG TCTACAGACC TGGAGGGAAC AGACATGTTG GCAGAGAAGG
18551 CAGACCGAAG AGAATACATT GATCTGTTAA AGAAAATGCT CACAATTGAT
18601 GCAGATAAGA GAATTACCCC TCTAAAAACT CTTAACCATC AGTTTGTGAC
18651 AATGACTCAC CTTTTGGATT TTCCACATAG CAATCAGTGA GTATGGAATA
18701 TTCTGGGGCT TTTGCCATGT GGTTCTTTGT TGAGTTACCG CCTTATCAAT
18751 GGCACTATCA AATGAGCCCG CCACTTTGGT GCTTATAAAT CTGGCTCAGC
18801 AGTGCTTTTC TTTCTCATTG AAACATCATA AGATAAAAAT TAGATGTGTA
18851 TTTTTCTTCC CTATGATTAT ACAAATTCTT GATTTATTTT ATCTGAAAGT
18901 GATTGGGAAA AAAAGCTTTG ATCCATGTTC ATCTTGAGTT ATTTGCTGTC
18951 TGTTTAAATC TCAGCATTCA TTTAATGAAT CTTTAATCTC CTTTTCAGTG
19001 TTAAGTCTTG TTTTCAGAAC ATGGAGATCT GCAAGCGGAG GGTTCACATG
19051 TATGATACAG TGAGTCAGAT CAAGAGTCCC TTCACTACAG ATGTTGCCCC
19101 AAATACAAGC ACAAATCTAA CCATGAGCTT CAGCAATCAG CTCAATACAG
19151 TGCACAATCA GGTATTCAAT AAATAATTTT GGAAACTCAA GCTTAAGTGG
19201 GATAGAAACT AGTAAGAATA CAGGGCAAGG TAAAGAACCA ATTTTTGTTT
19251 TGGTGGTCTT GTTGCTTCTT AGAAATTCTC CACTTGACAA AAGTTGATGG
19301 AAAACAGGGT AGACTGATAA TACTTACCAG GCACAGGCTA ACTAAAGTTA
19351 AATATAAAGG CCTAATCCAT GCCCTCATAT GTTCAGCATC GTCAAATAAA
19401 TGGGGTCTGA CTATTATGCT ACTTACTGCT GTTAGTTTTA CTGACTTTAG
19451 CCAAATGACT TTCTCCCTGT TAGGAGAAGG ATTTTATATC TCTTGTTACT
19501 GTATTGAAAG GTTTCCAGTC ATTAACTTTA AGGGTGGTTT TGCATTTGTT
19551 TGCTAGCCAG TGATATTTGC ATTTAGGTTT ATTTCTGAAG ATGTAAGCTT
19601 CCCAGTTTCT TGGCTGGGTC TACTTTTTTA ATGGAAGAGC CTATGAGATT
19651 TGGTGGGATC TTCCATCCAG TAATTTTTTG TGCAGAAGTA GTTGGGGTTT
19701 GTGTAGCCAC AGCCAACATA GGACCATTCG TTTTTTTTTT TTTATTTGCT
19751 TATTTGACCA TATAATATGC CTTCAATTTA GGGACTAGGG AAGTTTCTTA
19801 AGCAGAGAGT TATTTCAGAG GCAGTTAACA TTACATTTTA AAACATTATT
19851 CTACGTTTTT CTGGATAAAT TCTGTATATA TAAAATTATT GTGTGTCTCT
19901 ACTTAATACA AGTGTACAAA TATAATCCTT TTGTTTTTAG GCCAGTGTTC
19951 TAGCTTCCAG TTCTACTGCA GCAGCTGCTA CTCTTTCTCT GGCTAATTCA
20001 GATGTCTCAC TACTAAACTA CCAGTCAGCT TTGTACCCAT CATCTGCTGC
20051 ACCAGTTCCT GGAGTTGCCC AGCAGGGTGT TTCCTTGCAG CCTGGAACCA
20101 CCCAGATTTG CACTCAGACA GATCCATTCC AACAGACATT TATAGTATGT
20151 CCACCTGCGT TTCAAAGTAA GTGGGGAAAC TCCTGTATCA TATGGTATTG
20201 TATCAGACCT ACCTGCTTTA GGCAGCTCTA GTTGTTTAGT TCTGATCTTT
20251 ACAAGTTTAA ACTCTGTCTC TGATGAAGAA GGTAACTAAA ATTGGGTAAT
```

FIGURE 3G

```
20301 ATCGCAAAAT GGATTTTCTC TTTTTACATA GGCTATTTAT CTAATTATGA
20351 TGCTATCTGA TGCATTGTAA GAGCTCACTT TATGTTTCCT TAATTGAATT
20401 GCCTGATACC AGTTTTCTTG CCCATTGAGT CCTTGTGTCA ATGTCGTACG
20451 TCTTGTATAA GCATGTATCT GTCAATATGC AAAATCTATA CAACTTGAAA
20501 AAATTTGTTG TAAGCAGAAT TGCTAAATAN NNNNNNNNNN NNNNNNNNNN
20551 NNNNNNNNNN NNNNNNNNNN NNNNNNNNNN NNNNNNNNNN NNNNNNNNNN
20601 NNNNNNNNNN NNNNNNNNNN NNNNNNNNNN NNNNNNNNNN NNNNNNNNNN
20651 NNNNNNNNNN NNNNNNNNNN NNNNNNNNNN NNNNNNNNNN NNNNNNNNNN
20701 NNNNNNNNNN NNNNNNNNNN NNNNNNNNNN NNNNNNNNNN NNNNNNNNNN
20751 NNNNNNNNNN NNNNNNNNNN NNNNNNNNNN NNNNNNNNNN NNNNNNNNNN
20801 NNNNNNNNNN NNNNNNNNNN NNNNNNNNNN NNNNNNNNNN NNNNNNNNNN
20851 NNNNNNNNNN NNNNNNNNNN NNNNNNNNNN NNNNNNNNNN NNNNNNNNNN
20901 NNNNNNNNNN NNNNNNNNNN NNNNNNNNNN NNNNNNNNNN NNNNNNNNNN
20951 NNNNNNNNNN NNNNNNNNNN NNNNNNNNNN NNNNNNNNNN NNNNNNNNNN
21001 NNNNNNNNNN NNNNNNNNNN NNNNNNNNNN NNNNNNNNNN NNNNNNNNNN
21051 NNNNNNNNNN NNNNNNNNNN NNNNNNNNNN NNNNNNNNNN NNNNNNNNNN
21101 NNNNNNNNNN NNNNNNNNNN NNNNNNNNNN NNNNNNNNNN NNNNNNNNNN
21151 NNNNNNNNNN NNNNNNNNNN NNNNNNNNNN NNNNNNNNNN NNNNNNNNNN
21201 NNNNNNNNNN NNNNNNNNNN NNNNNNNNNN NNNNNNNNNN NNNNNNNNNN
21251 NNNNNNNNNN NNNNNNNNNN NNNNNNNNNN NNNNNNNNNN NNNNNNNNNN
21301 NNNNNNNNNN NNNNNNNNNN NNNNNNNNNN NNNNNNNNNN NNNNNNNNNN
21351 NNNNNNNNNN NNNNNNNNNN NNNNNNNNNN NNNNNNNNNN NNNNNNNNNN
21401 NNNNNNNNNN NNNNNNNNNN NNNNNNNNNN NNNNNNNNNN NNNNNNNNNN
21451 NNNNNNNNNN NNNNNNNNNN NNNNNNNNNN NNNNNNNNNN NNNNNNNNNN
21501 NNNNNNNNNN NNNNNNNNNN NNNNNNNNNN NNNNNNNNNN NNNNNNNNNN
21551 NNNNNNNNNN NNNNNNNNNN NNNNNNNNNN NNNNNNNNNN NNNNNNNNNN
21601 NNNNNNNNNN NNNNNNNNNN NNNNNNNNNN NNNNNNNNNN NNNNNNNNNN
21651 NNNNNNNNNN NNNNNNNNNN NNNNNNNNNN NNNNNNNNNN NNNNNNNNNN
21701 NNNNNNNNNN NNNNNNNNNN NNNNNNNNNN NNNNNNNNNN NNNNNNNNNN
21751 NNNNNNNNNN NNNNNNNNNN NNNNNNNNNN NNNNNNNNNN NNNNNNNNNN
21801 NNNNNNNNNN NNNNNNNNNN NNNNNNNNNN NNNNNNNNNN NNNNNNNNNN
21851 NNNNNNNNNN NNNNNNNNNN NNNNNNNNNN NNNNNNNNNN NNNNNNNNNN
21901 NNNNNNNNNN NNNNNNNNNN NNNNNNNNNN NNNNNNNNNN NNNNNNNNNN
21951 NNNNNNNNNN NNNNNNNNNN NNNNNNNNNN NNNNNNNNNN NNNNNNNNNN
22001 NNNNNNNNNN NNNNNNNNNN NNNNNNNNNN NNNNNNNNNN NNNNNNNNNN
22051 NNNNNNNNNN NNNNNNNNNN NNNNNNNNNN NNNNNNNNNN NNNNNNNNNN
22101 NNNNNNNNNN NNNNNNNNNN NNNNNNNNNN NNNNNNNNNN NNNNNNNNNN
22151 NNNNNNNNNN NNNNNNNNNN NNNNNNNNNN NNNNNNNNNN NNNNNNNNNN
22201 NNNNNNNNNN NNNNNNNNNN NNNNNNNNNN NNNNNNNNNN NNNNNNNNNN
22251 NNNNNNNNNN NNNNNNNNNN NNNNNNNNNN NNNNNNNNNN NNNNNNNNNN
22301 NNNNNNNNNN NNNNNNNNNN NNNNNNNNNN NNNNNNNNNN NNNNNNNNNN
22351 NNNNNNNNNN NNNNNNNNNN NNNNNNNNNN NNNNNNNNNN NNNNNNNNNN
22401 NNNNNNNNNN NNNNNNNNNN NNNNNNNNNN NNNNNNNNNN NNNNNNNNNN
22451 NNNNNNNNNN NNNNNNNNNN NNNNNNNNNN NNNNNNNNNN NNNNNNNNNN
22501 NNNNNNNNNN NNNNNNNNNN NNNNNNNNNN NNNNNNNNNN NNNNNNNNNN
22551 NNNNNNNNNN NNNNNNNNNN NNNNNNNNNN NNNNNNNNNN NNNNNNNNNN
22601 NNNNNNNNNN NNNNNNNNNN NNNNNNNNNN NNNNNNNNNN NNNNNNNNNN
22651 NNNNNNNNNN NNNNNNNNNN NNNNNNNNNN NNNNNNNNNN NNNNNNNNNN
22701 NNNNNNNNNN NNNNNNNNNN NNNNNNNNNN NNNNNNNNNN NNNNNNNNNN
22751 NNNNNNNNNN NNNNNNNNNN NNNNNNNNNN NNNNNNNNNN NNNNNNNNNN
22801 NNNNNNNNNN NNNNNNNNNN NNNNNNNNNN NNNNNNNNNN NNNNNNNNNN
22851 NNNNNNNNNN NNNNNNNNNN NNNNNNNNNN NNNNNNNNNN NNNNNNNNNN
22901 NNNNNNNNNN NNNNNNNNNN NNNNNNNNNN NNNNNNNNNN NNNNNNNNNN
22951 NNNNNNNNNN NNNNNNNNNN NNNNNNNNNN NNNNNNNNNN NNNNNNNNNN
23001 NNNNNNNNNN NNNNNNNNNN NNNNNNNNNN NNNNNNNNNN NNNNNNNNNN
23051 NNNNNNNNNN NNNNNNNNNN NNNNNNNNNN NNNNNNNNNN NNNNNNNNNN
23101 NNNNNNNNNN NNNNNNNNNN NNNNNNNNNN NNNNNNNNNN NNNNNNNNNN
23151 NNNNNNNNNN NNNNNNNNNN NNNNNNNNNN NNNNNNNNNN NNNNNNNNNN
```

FIGURE 3H

```
23201 NNNNNNNNNN NNNNNNNNNN NNNNNNNNNN NNNNNNNNNN NNNNNNNNNN
23251 NNNNNNNNNN NNNNNNNNNN NNNNNNNNNN NNNNNNNNNN NNNNNNNNNN
23301 NNNNNNNNNN NNNNNNNNNN NNNNNNNNNN NNNNNNNNNN NNNNNNNNNN
23351 NNNNNNNNNN NNNNNNNNNN NNNNNNNNNN NNNNNNNNNN NNNNNNNNNN
23401 NNNNNNNNNN NNNNNNNNNN NNNNNNNNNN NNNNNNNNNN NNNNNNNNNN
23451 NNNNNNNNNN NNNNNNNNNN NNNNNNNNNN NNNNNNNNNN NNNNNNNNNN
23501 NNNNNNNNNN NNNNNNNNNN NNNNNNNNNN NNNNNNNNNN NNNNNNNNNN
23551 NNNNNNNNNN NNNNNNNNNN NNNNNNNNNN NNNNNNNNNN NNNNNNNNNN
23601 NNNNNNNNNN NNNNNNNNNN NNNNNNNNNN NNNNNNNNNN NNNNNNNNNN
23651 NNNNNNNNNN NNNNNNNNNN NNNNNNNNNN NNNNNNNNNN NNNNNNNNNN
23701 NNNNNNNNNN NNNNNNNNNN NNNNNNNNNN NNNNNNNNNN NNNNNNNNNN
23751 NNNNNNNNNN NNNNNNNNNN NNNNNNNNNN NNNNNNNNNN NNNNNNNNNN
23801 NNNNNNNNNN NNNNNNNNNN NNNNNNNNNN NNNNNNNNNN NNNNNNNNNN
23851 NNNNNNNNNN NNNNNNNNNN NNNNNNNNNN NNNNNNNNNN NNNNNNNNNN
23901 NNNNNNNNNN NNNNNNNNNN NNNNNNNNNN NNNNNNNNNN NNNNNNNNNN
23951 NNNNNNNNNN NNNNNNNNNN NNNNNNNNNN NNNNNNNNNN NNNNNNNNNN
24001 NNNNNNNNNN NNNNNNNNNN NNNNNNNNNN NNNNNNNNNN NNNNNNNNNN
24051 NNNNNNNNNN NNNNNNNNNN NNNNNNNNNN NNNNNNNNNN NNNNNNNNNN
24101 NNNNNNNNNN NNNNNNNNNN NNNNNNNNNN NNNNNNNNNN NNNNNNNNNN
24151 NNNNNNNNNN NNNNNNNNNN NNNNNNNNNN NNNNNNNNNN NNNNNNNNNN
24201 NNNNNNNNNN NNNNNNNNNN NNNNNNNNNN NNNNNNNNNN NNNNNNNNNN
24251 NNNNNNNNNN NNNNNNNNNN NNNNNNNNNN NNNNNNNNNN NNNNNNNNNN
24301 NNNNNNNNNN NNNNNNNNNN NNNNNNNNNN NNNNNNNNNN NNNNNNNNNN
24351 NNNNNNNNNN NNNNNNNNNN NNNNNNNNNN NNNNNNNNNN NNNNNNNNNN
24401 NNNNNNNNNN NNNNNNNNNN NNNNNNNNNN NNNNNNNNNN NNNNNNNNNN
24451 NNNNNNNNNN NNNNNNNNNN NNNNNNNNNN NNNNNNNNNN NNNNNNNNNN
24501 NNNNNNNNNN NNNNNNNNNN NNNNNNNNNN NNNNNNNNNN NNNNNNNNNN
24551 NNNNNNNNNN NNNNNNNNNN NNNNNNNNNN NNNNNNNNNN NNNNNNNNNN
24601 NNNNNNNNNN NNNNNNNNNN NNNNNNNNNN NNNNNNNNNN NNNNNNNNNN
24651 NNNNNNNNNN NNNNNNNNNN NNNNNNNNNN NNNNNNNNNN NNNNNNNNNN
24701 NNNNNNNNNN NNNNNNNNNN NNNNNNNNNN NNNNNNNNNN NNNNNNNNNN
24751 NNNNNNNNNN NNNNNNNNNN NNNNNNNNNN NNNNNNNNNN NNNNNNNNNN
24801 NNNNNNNNNN NNNNNNNNNN NNNNNNNNNN NCAAGTTTTT TTTCCACCTA
24851 GTGGATTAAA AAGTGAATAA TGCTGGGCAC AGTGGCTCAC ACCTGTAATC
24901 CCGGCACTTT GGGAGGCCAA GATGGGCAGA TCATGAGGTC AGGAGTTCGA
24951 GACCAGCCTG GCCAACATGG TGAAACCCCG TCTCTACTGA AAATATAAAA
25001 ATTAGACGGG CGTGGTGGCG CACTCCTGTA GTCGCAGCTA CTTGGGAGGC
25051 TGTGGCAGAA GAATCGCTTG AACTTGGGAG CAGAGTTTGC AGTGAGCCCA
25101 GATAGCATCA CTGCACTCCA GCCTGGGTGA CAGAGCGAGA CTCCATCTCA
25151 NAAAAAAAAA AAAAAAAAAA AAAAAAAATG AAAGTGAATT TAATTTACTA
25201 AGTGAAGATT TTTTTGTTTT TGCCTGTACT CTTAATGGAG ATGGGATGAA
25251 TATTGTGTTT TAAATTTTGT AGCATAAAAA AAATTTAGAA TTCTTTTAAA
25301 CCATCCCTCA CTATATCAAA CATCTTTCCA TTAACCTAAC CTGAGGGGAA
25351 GTCTCCCTTT TCTTAACTTC CAAGACTTCT ATGAATGAAA CTTCTTTGTC
25401 TTAAGTGTCT AGGATTAAAA CCTGAACAGT GGATTATTTG AACAGAGAAG
25451 CTGAAAACAA AATAATCTTA AAACAGTACT CCCAGACCTT GCAAAACTAT
25501 TTAACTGTGA TGCTGTTTTC AATAGCTGGA CTACAAGCAA CAACAAAGCA
25551 TTCTGGATTC CCTGTGAGGA TGGATAATGC TGTACCGATT GTACCGCAGG
25601 CACCAGCTGC TCAGCCACTA CAGATTCAGT CAGGAGTTCT CACGCAGGTA
25651 AAAGCTAGAG CAATGTGGAT ACTCAGTATT GCTAAACACT ATTGAGATTC
25701 AGATATTTTG TCCTAGAAAA TGGTATTTCC TTTGACTATA AGATCTTTCT
25751 TGGTCATGAT TCAGTGGACT TAAAATGAAA CATCTCTATG GAACAATATA
25801 CTAATTCCTA ACACTATTGC AACTCTGCCA TTGTCTTCCT TAGACTTGCA
25851 GGGAAAAAAT ATCCAGACAT TCTTGAGAAA TGGTCTTCTG AGTAAGTTTA
25901 CTCTAATTTT GCGGGGTGAA GCGTTTTTTT TTGTTGTTGT TTGTTTTTTA
25951 AATGTTGGAG CTCATATAAA GATAAGTATA TATGTAGCAT TTTGATTCTA
26001 AAATATAAGC TTCCACTTTT GCACCCTTTG TGTCCCTTTT GCTCACTCTT
26051 TTAGAATTTC ATCACAGTTG AGAGGCTGGA TCACATCAGG ATGCCTCTTC
```

FIGURE 3I

```
26101 ACATATTACA TTCCTTCATT CCGTGTGTTT AACCATATTG TAGAAAGCTT
26151 TAAAACTTTA TACTTGCTAT GGAACATTCG ACTAAGATGA TAGAGAAAAT
26201 TGTAAAGTAT TTAAATAGCA ACAAACAGTA TATTTTATAT TTTATATATA
26251 AATGTTTGTG GCCTATGACA CATAGGAAAT TCTCAAATCC AAAAACTCTA
26301 TTTTGTGAAC AGGAGGAAGA ATTCTTAATA AATGTCTCTG TTTCATAGAA
26351 CTGATCCCCT GAATCTAGCC CAAGGAGGAT TCCTATACTT CTTTGTTTTA
26401 GGCCATTGGC ATTTGACTTT GTGGGCCAAT GCCATACAAA GTTGAAGGGG
26451 GAAAGTTGTG TTTGGTATAT GCATTTTAGA TGCTATCAAA TTACTGTTCA
26501 TTGTCAGTAA TAACTTGGGG GGAATGAGAA CCCTTCTGAA TCCAGATATC
26551 CTGCCTCCGT GTTTGTTTCA CTCACCTGCC TAATCTACGT TTCAGGGAAG
26601 CTGTACACCA CTAATGGTAG CAACTCTCCA CCCTCAAGTA GCCACCATCA
26651 CACCGCAGTA TGCGGTGCCC TTTACTCTGA GCTGCGCAGC CGGCCGGCCG
26701 GCGCTGGTTG AACAGACTGC CGCTGTACTG GTAATTCCCC TCACTTGATT
26751 GTGTTACTAA CGGAGTTTCT TTGGTTTCTT TCTTTTTTGT TTTTTCCTGT
26801 TTGTTTTTGT TCTGTTTTTT TCTGGTTTAT TTTTCAAAAA AATTTTTTAG
26851 CTTAGTCTTT GCAGAGGGCA TGGAAGCATG TGCCATCTTG TGGCTGTGTT
26901 CTTGCTACAT CTTTTAATGT CTCATTGTTT TCCTCCCCCA ACATTTGCTG
26951 TAGCACTGTC TGACTGATGG TTATGTGGCT CTGTAAGGAG CCAGATCCCT
27001 TGATTCTTCT TTGCCAGCCT AGTGTGATAA AAGCTCTCGA TGTAGCCTCA
27051 GAAGAGCTTC AACACTGTTA CTTGTTTTCT GCCTTTTACC CTCTGATCCT
27101 TGAGAATGAA GGAAATGGCC TTTAATTTGG CTCAGCTACA GGTACCCGGA
27151 TGGCCAAAAT TGAGCTCGTT GGCAAGATAG CTTTCTCCTT TTTTTGCTGT
27201 TTTAAGGTTC TAAAACTTTT CTGCATGTGG AAATGCTTAA GATGCTCTTA
27251 ATTTATTGCT TTCTCAGTTG ATACTAACCA TCCTTCTATG GACACATGAA
27301 GATAGCTCTT TTTGCCACTC ATGATCAGTG GCAGCTTATA TCTTACATTT
27351 AAAGATATTC CCTTTAGAAT GTAGATCATA TTGTAGGTCA TATTGTTGGT
27401 TGAAATTAAA AGTGGACACA TTTTTAGGAG TTTTGGGAGG AATTAATTAT
27451 TTTACAAATA GGTCTTTATA CAAAGGTTGA AAGTATGGCC AACAAACTAT
27501 GCAAATACAA TATCTTTGTT ATTAAAAGTC ATGGGGAATA GTTACTTAAT
27551 GTAGCTGCAA TTGTAGTACT GGGCTTAGAG ATAGAAAAAA CAACCAAGAC
27601 TTTGAGGTGT GTTTCAGGAT TTGTAACCTT AAGAGTGATT TTTTGGATGT
27651 GTTTTGGTTT ATATGGGGAG TTAGAATTGT TTATTGGATA TCCAGCATTT
27701 TCTCATTTGA AATTTAAAAT TAGGTAAGCA TCCAAAAACC TGAAAGGCAC
27751 TATTGAATCC TGTTATTTCT CTGTTTTCAA AGTTGCTTTA AATTTCTTTT
27801 GTTGTTTCTT AAGTATTCAT GTGAGTGAAA ACACTTCCAG AAACATACTT
27851 TGGTTGGAAT TTGGTTTTCA TTTTAAAAGT CTTTGTCACT TCCAGATTAA
27901 TTTTCTTGTA AGCAGAAAAC CTGAGTGTGA GGGAGTCAGA TATATTTCCA
27951 ACTTGATTGA TCCAAGCCAA TGGTTTTAAC TCACTCATCT GTAGTTTCGA
28001 GGTTGGAATG TTAGTTGACA CTTCTCCTTT GCTGCTTCTC TTAAGTTTGC
28051 ACTAGCCATT TGCTAAGCTT TGCATATTTT TGTTCTTCCT CTGTCAAAAC
28101 AGTTCGTCGC TTGGAACGCC AGATTCTGC CTCACATTGG AATGTTATTT
28151 CTTGCTTTGT ATTAAACTAC ATGCTTTGTC TTGTGCAGGT GTTGGCTTAT
28201 GGAAAGACGC ATGGTGTGAC TTAACATACT TCTTTTATTT TTTGTTTTGT
28251 TTTATTTTGT TTTAAATTCT GCTTATGGTA GCAGACGTGT TTGCAGTTTC
28301 TCTGCTTTGA AGGCTTCTTG TTTGGAACCA GTATTTGTAA CAAGTAGATC
28351 TGTTACTTGC AGAAATATTT TTAAAACAGT GTGTTGATGG CCTTGCAATT
28401 TGAAATTCAA GAAACAGAAC CATATGTACC CAAGCATTGT AGGTAATTGT
28451 ACTGCAGAAT TCAAGTTTAA AAAGGAAACT TCCAAATCCG TTCCCATTTT
28501 TTTTTTCAAA AAATGCCAGA ATTTCTGTGA GGAAGAAGTA CAGAAAACAT
28551 TTGTTGCTCA GTTATTGCA AGTGACATGG CTTTTTTAAA ACTAGAAATC
28601 ATGTATTTTC TTGTAGTGAT TAGTTTTTAT GTGGAAATAT TCCTGCAAAT
28651 GATACATAAA AACATATTTT AGGTAACTAT TAGAAACAAA GTATGATGCT
28701 TTCTGCTTCT AAAACATCTT ACTTTTTGCC TTATTTGAA ATTCCATTAT
28751 GTGGCTATAA ATGATGAATT AGCTTTTTCT TGCTGGCATA AGATTTTTTC
28801 CCCAAAAGGA TTAGGCCTTT GGTCATCCAC ATCTGGCTCC ATTTTCCAAA
28851 TACTACCCTT TTAAAAAAGG GAACAGTTCT GCCTTTTGTT TTATGGGTTG
28901 AATTGATCTG ATACCTTATC TGATTGGCAG TCAGATTAAA AAATTTTAAT
28951 CTCCAGGGAG TCCTCTTAAC TCTTTCTAGG GATTTATTTT AGAATTGTTG
```

FIGURE 3J

```
29001 CAAAAATGAA ACTCCAGCAT TTAACCAGCT CTTATCTCTG AACTCTCAGA
29051 CTCCTTTTCT CTACAGTATA ATAGAAGCTC TTAACCGCAG GGATCTTCTT
29101 TTCTTTAATA CCCGGGTGGT CAGGTTATGG GGGTGAGCAA GAGAAAGCAG
29151 TATGTTTTCT TTCCCCATTC ATAAGACTTG TAGCTTGAGC CCCTCTGACC
29201 TTTCTTTTTT AATCTCTGCA AGTTAACAAT CTACAAGCAA CTTCTTTTAA
29251 GATATGAATT TTTCTTTCTT TAAAAAAACA GAAGAAAAAG CCAAGAATGA
29301 ATCAAGTCTG GATGTTTTTT ATGTGTGTTT CCTTACAGCA GGCGTGGCCT
29351 GGAGGGACTC AGCAAATTCT CCTGCCTTCA ACTTGGCAAC AGTTGCCTGG
29401 GGTAGCTCTA CACAACTCTG TCCAGCCCAC AGCAATGATT CCAGAGGCCA
29451 TGGGGAGTGG ACAGCAGCTA GCTGACTGGA GGCAAGTGTC CTGTGTTACT
29501 CTGGGAGATT TGTAAGGGCC GATCCCATAG GGTGGGAGCA CTTGGTAATA
29551 AGGAGAGAGA CTAGTAAGAA AATAAAGGAA AATTTGACAC TGTTGGAATC
29601 CTTTAAGAAC CCATATCAGG CTAGGAGATG GTGTTATAAG AAAACTTTGA
29651 ATATAGGAAA GCAGTAGGTT CTGAAGGTCA GGAATCATTT CTTCTAGATT
29701 TTTTAAAGAG AGTCTTAAGT GATTAGAAAC CATACAGTGA GATCCTAAAG
29751 CCTTGTAATC TAGGTCCCCA ACTTTATCTT TTATAATGAA AATTCTTTTT
29801 TTCTAATGTT TAATTTTTGT GATTACATAC TAGGTATATA TATTTATGGG
29851 GTACATGAGA TGTTTTGACA CAGGCATGTA ATGTGAAATA AGCACATCAT
29901 GGAAAAGGGG GTGTCCATCC CCTCAAGCAT TTATCCTTTG AGTTACAAAT
29951 AATCCAATTA CACTCTTTAA GTCATTTAAA AATGTACAAT TAAGTTATTA
30001 CTGACTATAA TCACCTATTG CGCTATCAAA TAGTAGTTCT TATTCTTTTT
30051 TTTTTTTTTT TGTACCCATT AACCATCCCT ACCTCCCCAC TAGCCCTCCA
30101 CTACTCTTAC CAGCCTCTGG TAACCATCCT ACTCTCTATG TCCATGAATT
30151 AAATTGTTTT GATTTTTAGA TCCCATAAAT AAGTGAGAAC ATGTGGTTTG
30201 TCTTTCTGTG TCTGGCTTAT TTCACTTAAC ATGATGATCT TGAGTTCCAT
30251 CCATGTTGTT GCAAATGACA ACGTGTACTT TTTGTGGCTG AGTAGTACTC
30301 CATTGTGTAT ATGTACCATA TTTTCTTTAT CCATTCATCT GTTGATGGAC
30351 ACTTAGGCTG CTTCCAAATC TTACTGTGAA CAGTGCTGCA ACATAGGAGT
30401 GCAGGTATCT CTTTGATATA CTGATTTCCT TTCTTTTGGG TATATACCCA
30451 GCAGTGGGAT TGCTGGATCA TATGGTAGCT CAATTTTTAG TTTTTACAGG
30501 AACCTCCAAA CTGTTCTCCA TAATAGTTGT ACTAACTTAC ATTCCTACCA
30551 ACAGTGTACA ATTGTTCCCT TTTTTCCATA TCCTTGGCAG TGTTTATTAT
30601 TGCTTGTCTT TTGGATATAA GCCATTTTAA CTGGGGTGAG ATAATATCTC
30651 ATTGCAGTTT TGATCTGCAT TTCTCTAATG ATCAGAGATG TTGAGCACCT
30701 TTTCATATGC CTGTTTGTCA TTTGTAAGTC ATCTTTTGGA AAATGTCTAT
30751 TCAATTCTTT TGCCCATTTT TTGATCGTAT TATTAGATTT TTTTCCATAG
30801 AGTTGTTTGA GCTGCTTACG TATTCTGGTT ATTAATCCCT TATCAGATGG
30851 TAGGTGCTCA ACTTTAAAAA AATAAAATGC AGCTGCATTT TGGCTAATTG
30901 CTTTTGATGT CTGTTTGGTC CTGATTCTTC AGTGGTTTTG GAATTCACTC
30951 TTCTCTTTCT TTCTGTTGGT ACAGGAATGC CCACTCTCAT GGCAACCAGT
31001 ACAGCACTAT CATGCAGCAG CCATCCTTGC TGACTAACCA TGTGACATTG
31051 GCCACTGCTC AGCCTCTGAA TGTTGGTGTT GCCCATGTTG TCAGACAACA
31101 ACAATCCAGT TCCCTCCCTT CGAAGAAGAA TAAGCAGTCA GCTCCAGTCT
31151 CTTCCAAGTG AGTCTGTGTT ACAGCTGATA GTTAAAACTG TGCCAGTTTG
31201 AGAGATATGT TGCCTTGCAT TTGGAATATT GTATAGACAT ATAATATAGA
31251 TATGAAGCAG CAAGTAGCTG CCAAATTGAG GAAGAGCAAA TCATTTCATC
31301 TGGGCATGTA CACCAGGTGT GTCCTGGTTT TATGATGGTC CTTTGTCTCT
31351 GCTGCCACTT TGAATCTAGG GCATTTTATG ATGTTTTTAT TTTACTTTAC
31401 AGAGTGAAAT TTAATCCTGG GATAAAGGGC TTATAAAAGT AAAATGTCTT
31451 TTGTATTTTG GTGTTCTTGT CCCTGGAAAC TCTTGCCAGC ATGGTGCTTA
31501 TTTTCACTGG AACTTATATA GTTAAATGTA TTTGCTTAAT GATTATGTAA
31551 AAAGGAATCA ATGAGTAAAT TGGAAAGCAG TCTGGGGAAA AGATACACAA
31601 TTTGGAAGGC CAAGGACTGA ATCATCTTTC CATGTGAACT TTTCCTACAG
31651 GTCCTCTCTA GATGTTCTGC CTTCCCAAGT CTATTCTCTG GTTGGGAGCA
31701 GTCCCCTCCG CACCACATCT TCTTATAATT CCTTGGTCCC TGTCCAAGAT
31751 CAGCATCAGC CCATCATCAT TCCAGATACT CCCAGCCCTC CTGTGAGTGT
31801 CATCACTATC CGAAGTGACA CTGATGAGGA AGAGGACAAC AAATACAAGC
31851 CCAGTAGGTA AGATAAGTGA ATGGTTCCTG GCTCTATTGG TTTTAGACTG
```

FIGURE 3K

```
31901 TTGGCCTCAG GCAAGTGGGC CCAGTTTGGC CTGTGAAAGA AAGGACCGGT
31951 GGGGCATGGT GGCTCACGCC TGTAATCCCA GCACTTTGGG AGGTTGAGGC
32001 CAGCAGATCA CCTGAGGTGA GGAGTTCAAG ACCAGCCTGG CCAACATGGC
32051 ACAACCCTGT CTCTACTAAA AATACAAAAA TTAGCAGGGC CGTGGTGGCA
32101 CATGTTTGTA TCCCAGCTAC TCGGGAGGCT GAGGCAGGAG AATCACTTGA
32151 ACCCAGGAGG CGGAGGTTAC AGTGAGCTGA GATCGTGCCA CTGTACTCCA
32201 GCCTGAGTGA CAGAGCAAGA CTGCATCCCC TCCCGCCCCC ACCCAAAAAA
32251 AAGGGCCGAA GAAAAANNNN NNNNNNNNNN NNNNNNNNNN NNNNNNNNNN
32301 NNNNNNNNNN NNNNNCAAT GGTAAGAAAT AAAGGCTAGG AAAAATTCAA
32351 ATTTACTGAC GCCAGAATAG GGTGAGTTGA GTCACCAGTT ATTAACTTGC
32401 AGGAGTGGGG AACCCTATGA TCTCTTGATT CTCCCTCTTC CTGTCATACT
32451 TACAAGCAAA ATGCTGTTAC CTGAGCCAGA TTAGGATCTA TCTTGCTAAG
32501 AGGCAGAAGG AGGGGTGGCT GATTTCTGAC AGCATTCAAT GCCAGTGTGG
32551 GAGATTATGT GCTATACCCA TTCGAAAACA GTACAAGTCA GAACCTGAGC
32601 TCTTAACTTG GCCTTTGGTG CCCTGAGCTG GAGTGACCTC AGGATTCCTC
32651 ACTTCTTCCT TCTTTCTTCC AGAACCAGCA GTCATCGGCG GCTCCAACCT
32701 CACAGGAGAG AAGCAGCAAC CCAGCCCCCC GCAGGCAGCA GGCGTTTGTG
32751 GCCCCTCTCT CCCAAGCCCC CTACACCTTC AGCATGGCA GCCCGCTACA
32801 CTCGACAGGG CACCCACACC TTGCCCCGGC CCCTGCTCAC CTGCCAAGCC
32851 AGGCTCATCT GTATACGTAT GCTGCCCCGA CTTCTGCTGC TGCACTGGGC
32901 TCAACCAGCT CCATTGCTCA TCTTTTCTCC CCACAGGGTT CCTCAAGGCA
32951 TGCTGCAGCC TATACCACTC ACCCTAGCAC TTTGGTGCAC CAGGTCCCTG
33001 TCAGTGTTGG GCCCAGCCTC CTCACTTCTG CCAGCGTGGC CCCTGCTCAG
33051 TACCAACACC AGTTTGCCAC CCAATCCTAC ATTGGGTCTT CCCGAGGCTC
33101 AACAATTTAC ACTGGATACC CGCTGAGTCC TACCAAGATC AGCCAGTATT
33151 CCTACTTATA GTTGGTGAGC ATGAGGGAGG AGGAATCATG GCTACCTTCT
33201 CCTGGCCCTG CGTTCTTAAT ATTGGGCTAT GGAGAGATCC TCCTTTACCC
33251 TCTTGAAATT TCTTAGCCAG CAACTTGTTC TGCAGGGGCC CACTGAAGCA
33301 GAAGGTTTTT CTCTGGGGGA ACCTGTCTCA GTGTTGACTG CATTGTTGTA
33351 GTCTTCCCAA AGTTTGCCCT ATTTTTAAAT TCATTATTTT TGTGACAGTA
33401 ATTTTGGTAC TTGGAAGAGT TCAGATGCCC ATCTTCTGCA GTTACCAAGG
33451 AAGAGAGATT GTTCTGAAGT TACCCTCTGA AAAATATTTT GTCTCTCTGA
33501 CTTGATTTCT ATAAATGCTT TTAAAAACAA GTGAAGCCCC TCTTTATTTC
33551 ATTTTGTGTT ATTGTGATTG CTGGTCAGGA AAAATGCTGA TAGAAGGAGT
33601 TGAAATCTGA TGACAAAAAA AGAAAAATTA CTTTTTGTTT GTTTATAAAC
33651 TCAGACTTGC CTATTTTATT TTAAAAGCGG CTTACACAAT CTCCCTTTTG
33701 TTTATTGGAC ATTTAAACTT ACAGAGTTTC AGTTTTGTTT TAATGTCATA
33751 TTATACTTAA TGGGCAATTG TTATTTTTGC AAAACTGGTT ACGTATTACT
33801 CTGTGTTACT ATTGGAGATT CTCTCAATTG CTCCTGTGTT TGTTATAAAG
33851 TAGTGTTTAA AAGGCAGCTC ACCATTTGCT GGTAACTTAA TGTGAGAGAA
33901 TCCATATCTG CGTGAAAACA CCAAGTATTC TTTTTAAATG AAGCACCATG
33951 AATTCTTTTT TAAATTATTT TTTAAAAGTC TTTCTCTCTC TGATTCAGCT
34001 TAAATTTTTT TATCGAAAAA GCCATTAAGG TGGTTATTAT TACATGGTGG
34051 TGGTGGTTTT ATTATATGCA AAATCTCTGT CTATTATGAG ATACTGGCAT
34101 TGATGAGCTT TGCCTAAAGA TTAGTATGAA TTTTCAGTAA TACACCTCTG
34151 TTTTGCTCAT CTCTCCCTTC TGTTTTATGT GATTTGTTTG GGGAGAAAGC
34201 TAAAAAAACC TGAAACCAGA TAAGAACATT TCTTGTGTAT AGCTTTTATA
34251 CTTCAAAGTA GCTTCCTTTG TATGCCAGCA GCAAATTGAA TGCTCTCTTA
34301 TTAAGACTTA TATAATAAGT GCATGTAGGA ATTGCAAAAA ATATTTTAAA
34351 AATTTATTAC TGAATTTAAA AATATTTTAG AAGTTTTGTA ATGGTGGTGT
34401 TTTAATATTT TACATAATTA AATATGTACA TATTGATTAG AAAAATATAA
34451 CAAGCAATTT TTCCTGCTAA CCCAAAATGT TATTTGTAAT CAAATGTGTA
34501 GTGATTACAC TTGAATTGTG TACTTAGTGT GTATGTGATC CTCCAGTGTT
34551 ATCCCGGAGA TGGATTGATG TCTCCATTGT ATTTAAACCA AAATGAACTG
34601 ATACTTGTTG GAATGTATGT GAACTAATTG CAATTATATT AGAGCATATT
34651 ACTGTAGTGC TGAATGAGCA GGGGCATTGC CTGCAAGGAG AGGAGACCCT
34701 TGGAATTGTT TTGCACAGGT GTGTCTGGTG AGGAGTTTTT CAGTGTGTGT
34751 CTCTTCCTTC CCTTTCTTCC TCCTTCCCTT ATTGTAGTGC CTTATATGAT
```

FIGURE 3L

```
34801 AATGTAGTGG TTAATAGAGT TTACAGTGAG CTTGCCTTAG GATGGACCAG
34851 CAAGCCCCCG TGGACCCTAA GTTGTTCACC GGGATTTATC AGAACAGGAT
34901 TAGTAGCTGT ATTGTGTAAT GCATTGTTCT CAGTTTCCCT GCCAACATTG
34951 AAAAATAAAA ACAGCAGCTT TTCTCCTTTA CCACCACCTC TACCCCTTTC
35001 CATTTTGGAT TCTCGGCTGA GTTCTCACAG AAGCATTTTC CCCATGTGGC
35051 TCTCTCACTG TGCGTTGCTA CCTTGCTTCT GTGAGAATTC AGGAAGCAGG
35101 TGAGAGGAGT CAAGCCAATA TTAAATATGC ATTCTTTTAA AGTATGTGCA
35151 ATCACTTTTA GAATGAATTT TTTTTTCCTT TTCCCATGTG GCAGTCCTTC
35201 CTGCACATAG TTGACATTCC TAGTAAAATA TTTGCTTGTT GAAAAAAACA
35251 TGTTAACAGA TGTGTTTATA CCAAAGAGCC TGTTGTATTG CTTACCATGT
35301 CCCCATACTA TGAGGAGAAG TTTTGTGGTG CCGCTGGTGA CAAGGAACTC
35351 ACAGAAAGGT TTCTTAGCTG GTGAAGAATA TAGAGAAGGA ACCAAAGCCT
35401 GTTGAGTCAT TGAGGCTTTT GAGGTTTCTT TTTTAACAGC TTGTATAGTC
35451 TTGGGGCCCT TCAAGCTGTG AAATTGTCCT TGTACTCTCA GCTCCTGCAT
35501 GGATCTGGGT CAAGTAGAAG GTACTGGGGA TGGGGACATT CCTGCCCATA
35551 AAGGATTTGG GGAAAGAAGA TTAATCCTAA AATACAGGTG TGTTCCATCT
35601 GAATTGAAAA TGATATATTT GAGATATAAT TTTAGGACTG GTTCTGTGTA
35651 GATAGAGATG GTGTCAAGGA GGTGCAGGAT GGAGATGGGA GATTTCATGG
35701 AGCCTGGTCA GCCAGCTCTG TACCAGGTTG AACACCGAGG AGCTGTCAAA
35751 GTATTTGGAG TTTCTTCATT GTAAGGAGTA AGGGCTTCCA AGATGGGGCA
35801 GGTAGTCCGT ACAGCCTACC AGGAACATGT TGTGTTTTCN NNNNNNNNN
35851 NNNNNNNNNN NNNNNNNNNN NNNNNNNNNN NNNNNNNNNA AGATGGGAGG
35901 ATAGCTTGAG CCCAGAGGTT GAGGTCGCAG CGAGCTGTGA TCACTCCACT
35951 GCACTCCAGC CTGGGTGACA GAACAAGACG CTGTCACACA CACAAAAAAG
36001 AACAATTCAA TTTTCATGTA TTTTTCTTTT CCTCAGCTCT GGACTGAAGC
36051 CAAGGTCTAA TGTCATCAGT TATGTCACTG TCAATGATTC TCCAGACTCT
36101 GACTCTTCTT TGAGCAGCCC TTATTCCACT GATACCCTGA GTGCTCTCCG
36151 AGGCAATAG (SEQ ID NO:3)
```

FEATURES:

| | |
|---|---|
| Start: | 2490 |
| Exon: | 2490-3565 |
| Intron: | 3566-14639 |
| Exon: | 14640-14763 |
| Intron: | 14764-17436 |
| Exon: | 17437-17523 |
| Intron: | 17524-18501 |
| Exon: | 18502-18686 |
| Intron: | 18687-18998 |
| Exon: | 18999-19161 |
| Intron: | 19162-19940 |
| Exon: | 19941-20166 |
| Intron: | 20167-25525 |
| Exon: | 25526-25647 |
| Intron: | 25648-26595 |
| Exon: | 26596-26730 |
| Intron: | 26731-29338 |
| Exon: | 29339-29487 |
| Intron: | 29488-30974 |
| Exon: | 30975-31157 |
| Intron: | 31158-31650 |
| Exon: | 31651-31857 |
| Intron: | 31858-32003 |
| Exon: | 32004-32171 |
| Intron: | 32172-32402 |
| Exon: | 32403-32436 |
| Intron: | 32437-32440 |
| Exon: | 32441-32617 |

FIGURE 3M

Intron: 32618-32672
Exon: 32673-33158
Stop: 33159

CHROMSOME MAP POSITION:
Chromosome 1

ALLELIC VARIANTS (SNPs):

| DNA Position | Major | Minor | Domain |
|---|---|---|---|
| 4452 | T | A | Intron |
| 5330 | A | G | Intron |
| 9256 | A | C | Intron |
| 11773 | A | G | Intron |
| 12886 | G | A | Intron |
| 14131 | - | T | Intron |

Context:

| DNA Position | |
|---|---|
| 4452 | CCACCGTGCCCAGCCTATTTATTTATTTTTTAAGATGGAGTTTCACTTGCCACCCAGGC<br>TAGAGTGCAGTGGTGTGACATTGACTCACGGCAGCCTCCACCTCCTGGGGTCAAGTGATT<br>TCTCCTGCAACTCCTGTCCTGAGTAGCTGGGACTACAGGCACCTGCTACCACGCCCGGCT<br>AATTTTTTTGTTTTTAATAGAGATGGGGTTTCACCATGTTGACCGGGCTGGTTTTGAACT<br>CCTGACCTCAGGTGATCCACCCGCCTCAGCCTCCCAAAGTGATTAGAGGCGTGAGCCACC<br>[T,A]<br>TGCCCAGCCATTTTCCCATTTTGAAGAGTCTTGAAATACACAAAGATATTTACTTATTTG<br>TAATGAATCTGAGCATATGTTGCTGTTTTTTCGAACCTCTTATCTTGGCAGGTAAAATAA<br>CGTGGGAATAACTCTAGGTTTAACTCTAGTAACATTTTATTCTTTTACATTTTCTTCTGT<br>AGTAGCATGAATTGAATTACATGGTTGCTACAATCTCTTCCTGTTTTAACTTTCTCTAAA<br>TACTTTGAACTTAATGGGTTATCCTAGAATGGCCTTGACCCAAGTACCTTATACTTTAAT |
| 5330 | TTTATAAGGAGCTATACATGCCAGATGCCTGTAATAAAATTTGAGGAAATAGAAATTCTG<br>AATTAAGAATTTTATATTATGTGTGAAAATAATGTGAGGATATTTTAACCCATACAAGGA<br>CTCAGAAAAAATGTCATCTGCATGTTTCCTTTTTTAAAAACATTGTGGTAAGATGTTTAT<br>AATAGGAAATTTACAATTTTAACCATTTGGTACCACTCATTGTGTTAAGTACATTCATAG<br>TGTTGTGTAACCATCACTGCTGTCTGTTAAGTATATTCACAATGTTGTGTAACCATCACC<br>[A,G]<br>CTATTTCCAAATGTTTTCATCACCCAAAACAGAAATTCTAACCATTAAGCAATAACTCCC<br>TATTCTCTCTTCTTCCTACCACTGGTAATCTTGATTTGACTTTCTGTCTCTATGAATTTG<br>CCTATTCTAGATACTGCATGTAAGTGGAATCATACAATATTTGTCTTTTTGTGTCTAGTT<br>TATTTCACTTAGTGTAATGCTTTTGAGGCTAATCCATGCTGTAACATGTATCAGAACTTC<br>ATTCCTTTTATGGCTGTATAATATTCCATTGTTTGTATATACCACATTTTGTTTATGCAT |
| 9256 | GTGTCACAGTAATACTTGATAATGAGCCTAAGGCAGATGGAACAGCAGCTCAGGCATTCC<br>TTCTTTATCACTAGTTTTACCCGCAGTGGTCCTCTTAAGCTTCTTTGATGTTGCTTTGTT<br>GCCATATTAGAGTCCATTAAGTCCTCACCCTTCTGTCTTTCAAAAAACCTCTGTGAAATC<br>TGTTTGGCTGGTGAAGCATTTTGACTCCAAAGCTAGTCCTTCTCTTACCCACCTTTTTAG<br>TTTACCTTGCTTTGTCTTTCTGATAATATGCCAGTATTATCAGCTCACATAAATTTGCCA<br>[A,C]<br>CTTGCTGTGTCCATTGGCCCTGGGCATGGCTAAATGATTCAGGCAGTGGAAATAATATAC<br>TTTACTCTCTGGCTCACTGTAAATGTGCACAGACTCCAAGCAAAGCTCCTGTCTTTCGGG<br>CTTGAGTTTTAGAGACAAAGGTTTGCCATGCTTACAGGCTGAATGTTTTTCCCTACTGAA<br>CAAACTAGCCAGCCTTTATTTCAAGCTGAATCACTTTGTTACTTACGGAAGGAAAAGGTC<br>TAGAGAAGGAAAACGTATCTTCCATTTATCCTAGACAAACAAATAATCTAATTTCCTCTG |
| 11773 | CTTTTTTTTTTTTTTTTTGAGACAGAGTCTTACTCTGTCACCCAGGCTGGAGTGCAGTGGC |

FIGURE 3N

```
       ACTGTGTCAGCTCACTGCAACCTCCGTCTCCTGGGTTCAAGCAATTCTCCTGCCTCAGCC
       TCCTGAGTAGCTGGGATTACAGGTGCCCGCCACCACACCTGGCTGATTTTTTATATTTTT
       AGTAGAGATGGGGTTTCACCATGTTGGCCAGGCTGGTCTCAAACTCCTGACTTCAGGTGA
       TCCAGCCTCCTCGGCCTCCCAAAGTGCTTGTATTACAGGCATGAGCCACCGCACCCGGCC
       [A,G]
       GTTATTTCTTTGGTAAACAAAACCACAGTTCAAATTAAATACTACAAAAACTGATGATAT
       TGGTGGTTCCACCCATAGCTGTTAAAAAGTGTAAGCCCGAAGAGGCCTGGGTCGACTGCT
       ATTTGTATTTAAGGATCAGAAAAGCTTTCAGGCCCTGTGGAGTCCCCAGATTTACTGTTT
       TCTAAGGGCCACTATTTATGTATAAATACTAGGGGAGGATTTTTTTTTTCTTCTATGCCT
       AGTTTGCTTAGATGGGGAGGGATATTCTTATTTAGGGAAATTATATTCTCCTTGCTTAAT

12886  ACCTCTTAGTGCCAGTTTCTTCATCTGTAAAATGGAGGTAATACTTTTATTGCATAGAAT
       CTAACATGCCATTGATTATAAGATACATTATTTTTGTACCACTTAAAAAAGGAAAAGCGC
       TGCCATTAAACTAAAATATACCATCATTTGTAAGAATCTTCTT
       [G,A]
       ATTTCAGAGGTGCTAACATGTAAAAAGATGTGTATCTTAGAATTGATGACATCATAATAA
       TACTTTGATAGGATTGTTGTAAGGATTAAGTGACTCAACATTTATAAAGAACTTAGAACA
       GTGCATGGCACATAGTAGGCAATATTTATGTGTCATTTATTAT

14131  TTTTTGGACTGTCTTGGGTCTCCTAGGCTGGAGTGTAGTGGTGTGATCTTGGCTTACTGC
       AACCTCTACCTCCTGGGTTCAAGCGATTCTTTTGTCTCAACCTCCTGAGTAGCTGGGATT
       ACAGGCGCCCACCACCACACCTGACTCATTTTTGTATTTTTAGTAGATTTGGGGTTTCAC
       CATATTGGCCAAGCTGGTCTTGAACTTCTGACCTCAGGTGATCCACCCGCTTCGGCTTCC
       CAAAGTGCTGGGATTACAGGCATGAGCCACTGTGCCCAGTTGACCAGGCCTTTTAATTGA
       [-,T]
       TTTTTTTTTTTATGATTGAAATGGTGCTAGGAATAATAATAAAAAAAATCTATTATCCCT
       TATCTGTGATTGCAAAATTCAGAAAGCTCTCATAAATGAAAATTTTTCTTTAAGTTTGGT
       ATAAATTCATTTAATTGGCAAGACCTGACTTGAACCATTGTTAAGCTATTTGAAGTCTTT
       ATTTAGCCAACTTAGTATGACTGTTCCCATGTTTTGTTGCAGAAATATTAATGTGTTTGA
       TTATAGTGCACTGCCCTGAACTCCACTGGGATTATTATATAATGTGTACTTTGTGTTCTG
```

FIGURE 3O

SEQUENCE LISTING

<160> NUMBER OF SEQ ID NOS: 4

<210> SEQ ID NO 1
<211> LENGTH: 3565
<212> TYPE: DNA
<213> ORGANISM: Human

<400> SEQUENCE: 1

```
ttcttccttt ctctcaatat aggtatggca tcacagctgc aagtgttttc g ccccatca      60 gtgtcgtcga gtgccttctg cagtgcgaag aaactgaaaa tagagccctc t ggctgggat    120 gtttcaggac agagtagcaa cgacaaatat tatacccaca gcaaaaccct c ccagccaca    180 caagggcaag ccaactcctc tcaccaggta gcaaatttca acatccctgc t tacgaccag    240 ggcctcctcc tcccagctcc tgcagtggaa catattgttg taacagccgc t gatagctcg    300 ggcagtgctg ctacatcaac cttccaaagc agccagaccc tgactcacag a agcaacgtt    360 tctttgcttg agccatatca aaaatgtgga ttgaaacgaa aaagtgagga a gttgacagc    420 aacggtagtg tgcagatcat agaagaacat ccccctctca tgctgcaaaa c aggactgtg    480
```

-continued

| | | | | |
|---|---|---|---|---|
| gtgggtgctg | ctgccacaac | caccactgtg | accacaaaga | gtagcagttc c agcggagaa | 540 |
| ggggattacc | agctggtcca | gcatgagatc | ctttgctcta | tgaccaatag c tatgaagtc | 600 |
| ttggagttcc | taggccgggg | gacatttgga | caggtggcta | agtgctggaa g aggagcacc | 660 |
| aaggaaattg | tggctattaa | aatcttgaag | aaccacccct | cctatgccag a caaggacag | 720 |
| attgaagtga | gcatccttc | ccgcctaagc | agtgaaaatg | ctgatgagta t aattttgtc | 780 |
| cgttcatacg | agtgctttca | gcataagaat | cacacctgcc | ttgttttga a atgttggag | 840 |
| cagaacttat | atgattttct | aaagcaaaac | aaatttagcc | cactgccact c aagtacatc | 900 |
| agaccaatct | tgcagcaggt | ggccacagcc | ttgatgaagc | tcaagagtct t ggtctgatc | 960 |
| cacgctgacc | ttaagcctga | aaacatcatg | ctggttgatc | cagttcgcca g ccctaccga | 1020 |
| gtgaaggtca | ttgactttgg | ttctgctagt | cacgtttcca | aagctgtgtg c tcaacctac | 1080 |
| ttacagtcac | gttactacag | agctcctgaa | attattcttg | ggttaccatt t tgtgaagct | 1140 |
| attgatatgt | ggtcactggg | ctgtgtgata | gctgagctgt | tcctgggatg g cctctttat | 1200 |
| cctggtgctt | cagaatatga | tcagacacct | gaagaacacg | aactggagac t ggaataaaa | 1260 |
| tcaaaagaag | ctcggaagta | cattttaat | tgcttagatg | acatggctca g gtgaatatg | 1320 |
| tctacagacc | tggagggaac | agacatgttg | gcagagaagg | cagaccgaag a gaatacatt | 1380 |
| gatctgttaa | agaaaatgct | cacaattgat | gcagataaga | gaattacccc t ctaaaaact | 1440 |
| cttaaccatc | agtttgtgac | aatgactcac | cttttggatt | ttccacatag c aatcatgtt | 1500 |
| aagtcttgtt | ttcagaacat | ggagatctgc | aagcggaggg | ttcacatgta t gatacagtg | 1560 |
| aatcagatca | agagtccctt | cactacacat | gttgccccaa | atacaagcac a aatctaacc | 1620 |
| atgagcttca | gcaatcagct | caatacagtg | cacaatcagg | ccagtgttct a gcttccagt | 1680 |
| tctactgcag | cagctgctac | tctttctctg | gctaattcag | atgtctcact a ctaaactac | 1740 |
| cagtcagctt | tgtacccatc | atctgctgca | ccagttcctg | gagttgccca g cagggtgtt | 1800 |
| tccttgcagc | ctggaaccac | ccagatttgc | actcagacag | atccattcca a cagacattt | 1860 |
| atagtatgtc | cacctgcgtt | tcaaactgga | ctacaagcaa | caacaaagca t tctggattc | 1920 |
| cctgtgagga | tggataatgc | tgtaccgatt | gtaccccagg | caccagctgc t cagccacta | 1980 |
| cagattcagt | caggagttct | cacgcaggga | agctgtacac | cactaatggt a gcaactctc | 2040 |
| caccctcaag | tagccaccat | cacgccgcag | tatgcggtgc | cctttactct g agctgcgca | 2100 |
| gccggccggc | cggcgctggt | tgaacagact | gccgctgtac | tgcaggcgtg g cctggaggg | 2160 |
| actcagcaaa | ttctcctgcc | ttcaacttgg | caacagttgc | ctggggtagc t ctacacaac | 2220 |
| tctgtccagc | ccacagcaat | gattccagag | gccatgggga | gtggacagca g ctagctgac | 2280 |
| tggaggaatg | cccactctca | tggcaaccag | tacagcacta | tcatgcagca g ccatccttg | 2340 |
| ctgactaacc | atgtgacatt | ggccactgct | cagcctcaat | gttggtgttg c ccatgttgt | 2400 |
| ctgacaacaa | caatccagtt | ccctcccttc | gaagaagaat | aagcagtcag c tccagtctc | 2460 |
| ttccaagtcc | tctctagatg | ttctgccttc | ccaagtctat | tctctggttg g gagcagtcc | 2520 |
| cctccgcacc | acatcttctt | ataattcctt | ggtccctgtc | caagatcagc a tcagcccat | 2580 |
| catcattcca | gatactccca | gccctcctgt | gagtgtcatc | actatccgaa g tgacactga | 2640 |
| tgaggaagag | gacaacaaat | acaagcccag | tagctctgga | ctgaagccaa g gtctaatgt | 2700 |
| catcagttat | gtcactgtca | atgattctcc | agactctgac | tcttcttga g cagcccta | 2760 |
| ttccactgat | accctgagtg | ctctccgagg | caatagtgga | tccgttttgg a ggggcctgg | 2820 |
| cagagttgtg | gcagatggca | ctggcacccg | cactatcatt | gtgcctccac t gaaaactca | 2880 |

-continued

```
gcttggtgac tgcactgtag caacccaggc ctcaggtctc ctgagcaata a gactaagcc    2940 agtcgcttca gtgagtgggc agtcatctgg atgctgtatc accccacag g gtatcgagc    3000 tcaacgcggg gggaccagtg cagcacaacc actcaatctt agccagaacc a gcagtcatc    3060 ggcggctcca acctcacagg agagaagcag caacccagcc cccgcaggc a gcaggcatt    3120 tgtggcccct ctctcccaag cccctacac cttccagcat ggcagcccgc t acactcgac    3180 agggcaccca caccttgccc cggcccctgc tcacctgcca agccaggctc a tctgtatac    3240 gtatgctgcc ccgacttctg ctgctgcact gggctcaacc agctccattg c tcatctttt    3300 ctccccacag ggttcctcaa ggcatgctgc agcctatacc actcaccta g cactttggt    3360 gcaccaggtc cctgtcagtg ttgggcccag cctcctcact tctgccagcg t ggcccctgc    3420 tcagtaccaa caccagtttg ccacccaatc ctacattggg tcttcccgag g ctcaacaat    3480 ttacactgga tacccgctga gtcctaccaa gatcagccag tattcctact t atagttggt    3540 gagcatgagg aagggcgaat tctgt                                             3565
```

<210> SEQ ID NO 2
<211> LENGTH: 1170
<212> TYPE: PRT
<213> ORGANISM: Human

<400> SEQUENCE: 2

```
Met Ala Ser Gln Leu Gln Val Phe Ser Pro P ro Ser Val Ser Ser
 1               5                  10                  15

Ala Phe Cys Ser Ala Lys Lys Leu Lys Ile G lu Pro Ser Gly Trp Asp
                20                  25                  30

Val Ser Gly Gln Ser Ser Asn Asp Lys Tyr T yr Thr His Ser Lys Thr
            35                  40                  45

Leu Pro Ala Thr Gln Gly Gln Ala Asn Ser S er His Gln Val Ala Asn
        50                  55                  60

Phe Asn Ile Pro Ala Tyr Asp Gln Gly Leu L eu Leu Pro Ala Pro Ala
 65                  70                  75                  80

Val Glu His Ile Val Val Thr Ala Ala Asp S er Gly Ser Ala Ala
                85                  90                  95

Thr Ser Thr Phe Gln Ser Ser Gln Thr Leu T hr His Arg Ser Asn Val
                100                 105                 110

Ser Leu Leu Glu Pro Tyr Gln Lys Cys Gly L eu Lys Arg Lys Ser Glu
            115                 120                 125

Glu Val Asp Ser Asn Gly Ser Val Gln Ile I le Glu Glu His Pro Pro
        130                 135                 140

Leu Met Leu Gln Asn Arg Thr Val Val Gly A la Ala Ala Thr Thr Thr
145                 150                 155                 160

Thr Val Thr Thr Lys Ser Ser Ser Ser Ser G ly Glu Gly Asp Tyr Gln
                165                 170                 175

Leu Val Gln His Glu Ile Leu Cys Ser Met T hr Asn Ser Tyr Glu Val
            180                 185                 190

Leu Glu Phe Leu Gly Arg Gly Thr Phe Gly G ln Val Ala Lys Cys Trp
        195                 200                 205

Lys Arg Ser Thr Lys Glu Ile Val Ala Ile L ys Ile Leu Lys Asn His
        210                 215                 220

Pro Ser Tyr Ala Arg Gln Gly Gln Ile Glu V al Ser Ile Leu Ser Arg
225                 230                 235                 240

Leu Ser Ser Glu Asn Ala Asp Glu Tyr Asn P he Val Arg Ser Tyr Glu
```

```
                          245                    250                    255
Cys Phe Gln His Lys Asn His Thr Cys Leu Val Phe Glu Met Leu Glu
                260                    265                    270

Gln Asn Leu Tyr Asp Phe Leu Lys Gln Asn Lys Phe Ser Pro Leu Pro
            275                    280                    285

Leu Lys Tyr Ile Arg Pro Ile Leu Gln Val Ala Thr Ala Leu Met
        290                    295                    300

Lys Leu Lys Ser Leu Gly Leu Ile His Ala Asp Leu Lys Pro Glu Asn
305                    310                    315                    320

Ile Met Leu Val Asp Pro Val Arg Gln Pro Tyr Arg Val Lys Val Ile
                    325                    330                    335

Asp Phe Gly Ser Ala Ser His Val Ser Lys Ala Val Cys Ser Thr Tyr
                340                    345                    350

Leu Gln Ser Arg Tyr Tyr Arg Ala Pro Glu Ile Ile Leu Gly Leu Pro
            355                    360                    365

Phe Cys Glu Ala Ile Asp Met Trp Ser Leu Gly Cys Val Ile Ala Glu
        370                    375                    380

Leu Phe Leu Gly Trp Pro Leu Tyr Pro Gly Ala Ser Glu Tyr Asp Gln
385                    390                    395                    400

Thr Pro Glu Glu His Glu Leu Glu Thr Gly Ile Lys Ser Lys Glu Ala
                    405                    410                    415

Arg Lys Tyr Ile Phe Asn Cys Leu Asp Asp Met Ala Gln Val Asn Met
                420                    425                    430

Ser Thr Asp Leu Glu Gly Thr Asp Met Leu Ala Glu Lys Ala Asp Arg
            435                    440                    445

Arg Glu Tyr Ile Asp Leu Leu Lys Lys Met Leu Thr Ile Asp Ala Asp
        450                    455                    460

Lys Arg Ile Thr Pro Leu Lys Thr Leu Asn His Gln Phe Val Thr Met
465                    470                    475                    480

Thr His Leu Leu Asp Phe Pro His Ser Asn His Val Lys Ser Cys Phe
                    485                    490                    495

Gln Asn Met Glu Ile Cys Lys Arg Arg Val His Met Tyr Asp Thr Val
                500                    505                    510

Asn Gln Ile Lys Ser Pro Phe Thr Thr His Val Ala Pro Asn Thr Ser
            515                    520                    525

Thr Asn Leu Thr Met Ser Phe Ser Asn Gln Leu Asn Thr Val His Asn
        530                    535                    540

Gln Ala Ser Val Leu Ala Ser Ser Ser Thr Ala Ala Ala Thr Leu
545                    550                    555                    560

Ser Leu Ala Asn Ser Asp Val Ser Leu Leu Asn Tyr Gln Ser Ala Leu
                    565                    570                    575

Tyr Pro Ser Ser Ala Ala Pro Val Pro Gly Val Ala Gln Gln Gly Val
                580                    585                    590

Ser Leu Gln Pro Gly Thr Thr Gln Ile Cys Thr Gln Thr Asp Pro Phe
            595                    600                    605

Gln Gln Thr Phe Ile Val Cys Pro Pro Ala Phe Gln Thr Gly Leu Gln
        610                    615                    620

Ala Thr Thr Lys His Ser Gly Phe Pro Val Arg Met Asp Asn Ala Val
625                    630                    635                    640

Pro Ile Val Pro Gln Ala Pro Ala Ala Gln Pro Leu Gln Ile Gln Ser
                    645                    650                    655

Gly Val Leu Thr Gln Gly Ser Cys Thr Pro Leu Met Val Ala Thr Leu
                660                    665                    670
```

```
His Pro Gln Val Ala Thr Ile Thr Pro Gln Tyr Ala Val Pro Phe Thr
            675                 680                 685
Leu Ser Cys Ala Ala Gly Arg Pro Ala Leu Val Glu Gln Thr Ala Ala
        690                 695                 700
Val Leu Gln Ala Trp Pro Gly Thr Gln Gln Ile Leu Leu Pro Ser
705                 710                 715                 720
Thr Trp Gln Gln Leu Pro Gly Val Ala Leu His Asn Ser Val Gln Pro
                725                 730                 735
Thr Ala Met Ile Pro Glu Ala Met Gly Ser Gly Gln Gln Leu Ala Asp
            740                 745                 750
Trp Arg Asn Ala His Ser His Gly Asn Gln Tyr Ser Thr Ile Met Gln
        755                 760                 765
Gln Pro Ser Leu Leu Thr Asn His Val Thr Leu Ala Thr Ala Gln Pro
770                 775                 780
Leu Asn Val Gly Val Ala His Val Val Arg Gln Gln Ser Ser Ser
785                 790                 795                 800
Leu Pro Ser Lys Lys Asn Lys Gln Ser Ala Pro Val Ser Ser Lys Ser
                805                 810                 815
Ser Leu Asp Val Leu Pro Ser Gln Val Tyr Ser Leu Val Gly Ser Ser
            820                 825                 830
Pro Leu Arg Thr Thr Ser Ser Tyr Asn Ser Leu Val Pro Val Gln Asp
        835                 840                 845
Gln His Gln Pro Ile Ile Ile Pro Asp Thr Pro Ser Pro Pro Val Ser
        850                 855                 860
Val Ile Thr Ile Arg Ser Asp Thr Asp Glu Glu Glu Asp Asn Lys Tyr
865                 870                 875                 880
Lys Pro Ser Ser Ser Gly Leu Lys Pro Arg Ser Asn Val Ile Ser Tyr
                885                 890                 895
Val Thr Val Asn Asp Ser Pro Asp Ser Asp Ser Ser Leu Ser Ser Pro
            900                 905                 910
Tyr Ser Thr Asp Thr Leu Ser Ala Leu Arg Gly Asn Ser Gly Ser Val
        915                 920                 925
Leu Glu Gly Pro Gly Arg Val Val Ala Asp Gly Thr Gly Thr Arg Thr
930                 935                 940
Ile Ile Val Pro Pro Leu Lys Thr Gln Leu Gly Asp Cys Thr Val Ala
945                 950                 955                 960
Thr Gln Ala Ser Gly Leu Leu Ser Asn Lys Thr Lys Pro Val Ala Ser
                965                 970                 975
Val Ser Gly Gln Ser Ser Gly Cys Cys Ile Thr Pro Thr Gly Tyr Arg
            980                 985                 990
Ala Gln Arg Gly Gly Thr Ser Ala Ala Gln Pro Leu Asn Leu Ser Gln
        995                 1000                1005
Asn Gln Gln Ser Ser Ala Ala Pro Thr Ser Gln Glu Arg Ser Ser Asn
        1010                1015                1020
Pro Ala Pro Arg Arg Gln Gln Ala Phe Val Ala Pro Leu Ser Gln Ala
1025                1030                1035                1040
Pro Tyr Thr Phe Gln His Gly Ser Pro Leu His Ser Thr Gly His Pro
                1045                1050                1055
His Leu Ala Pro Ala Pro Ala His Leu Pro Ser Gln Ala His Leu Tyr
            1060                1065                1070
Thr Tyr Ala Ala Pro Thr Ser Ala Ala Leu Gly Ser Thr Ser Ser
        1075                1080                1085
```

-continued

```
Ile Ala His Leu Phe Ser Pro Gln Gly Ser S er Arg His Ala Ala Ala
    1090                1095                 1100
Tyr Thr Thr His Pro Ser Thr Leu Val His G ln Val Pro Val Ser Val
1105            111 0               1115                    1120
Gly Pro Ser Leu Leu Thr Ser Ala Ser Val A la Pro Ala Gln Tyr Gln
            1125                1130                1135
His Gln Phe Ala Thr Gln Ser Tyr Ile Gly S er Ser Arg Gly Ser Thr
        1140                1145                1150
Ile Tyr Thr Gly Tyr Pro Leu Ser Pro Thr L ys Ile Ser Gln Tyr Ser
    1155                1160                1165
Tyr Leu
   1170

<210> SEQ ID NO 3
<211> LENGTH: 36159
<212> TYPE: DNA
<213> ORGANISM: Human
<220> FEATURE:
<221> NAME/KEY: misc_feature
<222> LOCATION: (1)...(36159)
<223> OTHER INFORMATION: n = A,T,C or G

<400> SEQUENCE: 3
aaagtgggga gatgttggaa ggcagcaagc agattttgga gtgcatttta a ggcaggttg      60 agacaggttt ttttttttgag ataggatcta gctctgttgc ccaggctaga g tgcaatgga   120 gtaatcacaa ctcactgtag cctcaatgtc ccagactcag atgattttcc t gcttcagcc   180 tcctgagtag ctgggaccac aggcatgtgc cacttacact tggctttttt t tttttttt    240 tcccggtaga gatggagtct ccccatgttg ctctggctgg tcttgaactc g tggactcaa   300 gtgatccttc caccttgggt tcctaaagtg ccaggattac aggcgtgagc c accacatct   360 ggcctaattt ttcttttctt ttcttttttt ttttgttaa tgcttcccag g ctgatcttg    420 aactcctgag ctcaagtgat cctcctgcct gggcctccca agtgcggga a ttacaggct    480 tgagcgacca tggccagcca agttgagaat cttggacatt atctccaaag c aatgagaaa   540 ccccgggaga aggggaagca agatggttaa gaagagagag cagttatctg a tttgcattg   600 tttaaaagca aagatctact gagtggattt aaggagatta gtttggaagc t actggcagt   660 ttgaactaga atggtgccaa taagggtagg gaaaaagggc tgatttgaaa t atacttagg   720 aggccagggg cagtggctca cgcctgtaat cccagcactt tgggagggtg a gggggtgg    780 atcacttgag ctcaggagtt tgagaccacc caggcaacat ggtgaaaacc c atctctact   840 aaaaatacaa agaaattaac tgggtgtggt cgtgcacgcc tctactctca g ctacttggg   900 aggctgaggc aggagaattg cttgagcccc agaggtgaag gttgcagcga g ccaagattg   960 caccattgca ctccagcttg ggctacagag tgagactctg tctcaaaaaa a aaaaaaaa   1020 aatatacaca cacacacaca cacacacaca cacacacact t aggagatgg            1080 aatggataag atagagatta gatgtggagg aataagggag aggaatgagc c aggataata  1140 gtattaaata tgtggtagac actatcattt tacatgtatt aaattattta a ttctcagaa  1200 caaccccatg aggtaggtat tgctatcacc attatgtagc tgaggaaaca g acatcccta  1260 attttttttc tttttttga cagggtgt cattctttca ccctggctgg a gtgcagtgg    1320 cacgatcaca gctcactgca gcctctacct ctgggctcag gtgatcactt c tgccttctg  1380 agtagctagg actacaggca tgtgccacca tgcctggcta acttttttt c tgttttttt   1440 ttttttttgt tgttgttgtt gtttgtttgt tttagagacg gtttcaccat g ttgcccagg  1500
```

-continued

```
ctggagctcc ctgatttctg gcttgaggcg ttggatgtgt gatggcatct c ataattaag    1560 atagaaaact gaaggtgggg tggaggctcg taagtttaat tctgaatgta t tgaatatga    1620 ggtgtttgtg aaatgtccaa gttgcaggt taagtagtca tttggatata g ggtttggag     1680 ttcaaagcga gagaatcctg ggttagagat agagatttta gtcttttgaa g atgactaat    1740 tttgaggagt aattattaaa aagggcaaa gggtagagca aggaaagagg g attactata     1800 gagccccaag gcatatgaga tcggatggtt gaaaatggag aagataaata t gaaatggct    1860 tgtgtgctat gtcagatgtt tggactttat tctgaaaaaa tagctttcag t ttaatctgt    1920 gggcttattg agctggaagt gtctgtggga tattcaggga cagaaagctg g actgttctt    1980 acatcctttc ctcatatttt tctgctaact ttcctcggtt cttcagaata t actctagct    2040 ttctcatcat cctggttact tttttttttt tttttttcaa ttttagtatt t ttagagaca    2100 gggtctcact acattgccta ggctggtctc gaactcctca gctcaggaga t cttcctgcc    2160 ttggcctccc aaagtgctgg aattaaaggc ttgagccact gtgcctggcc c atactggtt    2220 actttttat cttaaaatgt ggtagacaat tgaatgcatt ttatgtatga c ctgagcaga     2280 gtggataatc ttcactttgt ccagcacgtt ctgtacactg tttctatgaa t ataggtcaa    2340 gattgaatta gttttgaga agaggagaac attattacat catgtttctt t tatcaagta     2400 aaagtgtgtg tgtgtgtttg tgtgttttaa atctaagcct tgtatctttt a tccttgtgg    2460 tctaattctt cctttctctc aatataggta tggcatcaca gctgcaagtg t tttcgcccc    2520 catcagtgtc gtcgagtgcc ttctgcagtg cgaagaaact gaaaatagag c cctctggct    2580 gggatgtttc aggacagagt agcaacgaca aatattatac ccacagcaaa a ccctcccag    2640 ccacacaagg gcaagccaac tcctctcacc aggtagcaaa tttcaacatc c ctgcttacg    2700 accagggcct cctcctccca gctcctgcag tggagcatat tgttgtaaca g ccgctgata    2760 gctcgggcag tgctgctaca tcaaccttcc aaagcagcca gaccctgact c acagaagca    2820 acgtttcttt gcttgagcca tatcaaaaat gtggattgaa acgaaaaagt g aggaagttg    2880 acagcaacgg tagtgtgcag atcatagaag aacatccccc tctcatgctg c aaaacagga    2940 ctgtggtggg tgctgctgcc acaaccacca ctgtgaccac aaagagtagc a gttccagcg    3000 gagaagggga ttaccagctg gtccagcatg agatcctttg ctctatgacc a atagctatg    3060 aagtcttgga gttcctaggc cgggggacat ttggacaggt ggctaagtgc t ggaagagga    3120 gcaccaagga aattgtggct attaaaatct tgaagaacca ccctcctat g ccagacaag     3180 gacagattga agtgagcatc ctttcccgcc taagcagtga aaatgctgat g agtataatt    3240 ttgtccgttc atacgagtgc tttcagcata agaatcacac ctgccttgtt t ttgaaatgt    3300 tggagcagaa cttatatgat tttctaaagc aaaacaaatt tagcccactg c cactcaagt    3360 acatcagacc aatcttgcag caggtggcca cagccttgat gaagctcaag a gtcttggtc    3420 tgatccacgc tgaccttaag cctgaaaaca tcatgctggt tgatccagtt c gccagccct    3480 accgagtgaa ggtcattgac tttggttctg ctagtcacgt ttccaaagct g tgtgctcaa    3540 cctacttaca gtcacgttac tacaggcaag tggcaaatgc tgaaaatcgt a tcttaggct    3600 agagttctgt cctatatttt aacatatacc ccgtaggcta catatagcaa t gaatttgtt    3660 tatagattct gagatagaaa taggatatgt tttagctcat tctatgtgtg t ggcattcct    3720 atatatgaca tttatttctg aaattttatc tagcactgga aaaattaact c agtctgatt    3780 ctgaaagttg ttactagttg aattatacta gcacctggtt ctttagtatt a ttttacctc    3840
```

-continued

```
attttcccat ttatttatt ttatttattt atttatttat ttagagacag a atctcgctc    3900
tgtcgcccag gctggagtgc agtggcgtga tatcagctca ctgcaagccc c acctcctgg   3960
gttcacgcca ttctcctgcc tcagcctcct gagtagctgg gaccacaggc a cccgccatc   4020
acgcccggct aattttttt gtattttag tagagacggg gtttcaccgt g ttagccagg    4080
atggtctcga tatcctgacc tcgtgatcca cccgtctcgg cctcccaaag c gctgggatt   4140
acaggcgtga gccaccgtgc ccagcctatt tatttatttt tttaagatgg a gtttcactt   4200
gccacccagg ctagagtgca gtggtgtgac attgactcac ggcagcctcc a cctcctggg   4260
gtcaagtgat tctcctgca actcctgtcc tgagtagctg ggactacagg c acctgctac   4320
cacgcccggc taatttttt gtttttaata gagatgggggt ttcaccatgt t gaccgggct   4380
ggttttgaac tcctgacctc aggtgatcca cccgcctcag cctcccaaag t gattagagg   4440
cgtgagccac catgcccagc cattttccca ttttgaagag tcttgaaata c acaaagata   4500
tttacttatt tgtaatgaat ctgagcatat gttgctgttt tttcgaacct c ttatcttgg   4560
caggtaaaat aacgtgggaa taactctagg tttaactcta gtaacatttt a ttcttttac   4620
attttcttct gtagtagcat gaattgaatt acatggttgc tacaatctct t cctgtttta   4680
actttctcta aatactttga acttaatggg ttatcctaga atggccttga c ccaagtacc   4740
ttatacttta atgatatata ttctctagatt gatacttta atgtagctac c attttaata  4800
tataataatt attgggacag tatgtaaatg ctgatatata caattttgtc t gtaccataa   4860
ccaaggcttt taaaatgtgc ttttatcag cacccattta cttacttgcc t agttattaa   4920
ttttaaggaa tctaatattt agttttaatg gccatacatt aaatacaaat c atgtaagca   4980
tccaatcaag aagtgaaata ataaaaacat agataaccta taaatatgt t tataaggag    5040
ctatacatgc cagatgcctg taataaaatt tgaggaaata gaaattctga a ttaagaatt   5100
ttatattatg tgtgaaaata atgtgaggat attttaaccc atacaaggac t cagaaaaaa   5160
tgtcatctgc atgttccctt ttttaaaaac attgtggtaa gatgtttata a taggaaatt   5220
tacaatttta accatttgt accactcatt gtgttaagta cattcatagt g ttgtgtaac   5280
catcactgct gtctgttaag tatattcaca atgttgtgta accatcacca c tatttccaa   5340
atgttttcat caccccaaaac agaaattcta accattaagc aataactccc t attctctct   5400
tcttcctacc actggtaatc ttgatttgac tttctgtctc tatgaatttg c ctattctag   5460
atactgcatg taagtggaat catacaatat ttgtcttttt gtgtctagtt t atttcactt   5520
agtgtaatgc ttttgaggct aatccatgct gtaacatgta tcagaacttc a ttccttta   5580
tggctgtata atattccatt gtttgtatat accacatttt gttatgcat t catctgttg    5640
gtagatattt gggttgttgc tacctttagg ctgttgtgaa taatgctgct a tgaacattg   5700
gtgtacaagt atcctagtcc ctattttcag ttactttggg gatatagcta g gagggaatt   5760
gctgggtcac atgataattc tatgtttaac tttttgcaga attaccaaat t attttccac   5820
agaggctgca ctattttaca ttcctaccag cagtggatgt gcattccaaa t ttctccaca   5880
ttttctctaa catttgttat ttttttattt taaaaatatt gtttgtttat t tttacagag   5940
acagggctg cctctattgc tcatgctgga gtacagtggc acgatcatag t tcactgtag    6000
cctccaactc ctgacttga gcagtcctcc cacttcagcc tcccaagtag c taggactgc    6060
agtcacactc caccatacct ggctaattac tattattta ttttttgtgg c gacagtgtt    6120
ttgagggtct cattttgttg cccaatctgg tctcaaacta ctggcctcaa g ccatcctcc    6180
tgcctcagtc tcccaaagtt ctgggattac aggtgtgaac taccactcct g gccttgttt   6240
```

```
tgttttttaa ataatagcca tgggttttt ttttttttt ttttttttt t ttttttttgg    6300 aaagggagtt tcactttgt tgcctaggct ggagggcagg ggggcaatct c ggttaactg    6360 gaacctttgc ctcccaggat tttcctgcct aaacctccca agtagctggg a ttacagggg    6420 cctgccacca cacccagtta attttttgttt ttttaaaaaa aatggggttt t accatgttg    6480 gccagggggg gctccaactc ctgacctcag gggatctgcc caccttggcc t cccaaagtg    6540 ctgggattac aggcatgagc cactatgcct ggccaataat agtttttttt t gttttttttt    6600 ttgtttttttt tttgagatgg agtcttgctc tgttgccagg ctggagtgca g tggcacaat    6660 ctcggttcac tgcaacctcc acctcacagg ttcaagcagt tctcctagct t ggcctcctg    6720 agtagctggg aatacaggtg ccaccatgcc cagctaattt ttgtattttt a gtagagaca    6780 gggtttcacc atgttggccg ggatggtctc gatctcttga cctcgtgatg a agtgctggg    6840 attacaggca tgagccaccg ggcccggtca ataatagcca ttcttatggg t gtgaagtgg    6900 tatctcattg tggttttgat ttgtatttcc ctaatgatta atgatgttga g catttgttt    6960 tattttgttt gtttgagaca gagtcccact tgtcaccca ggctggggtg c agttgtgca    7020 atcatggctt actgcagcca tgacctctca ggctcaagca gtcctcccac c ttagccttt    7080 cgggtacctg agactacggg catgcacccc cacacctgac tagtgttttg t attttttagt    7140 agagacgggg tttcactgtg ttgcccaggc tggtctcaaa ctcataggct c aagtgatat    7200 gcccgcctcg gcaacccaaa gtgctgggat tacagacatg agccaccatg c ccagcctgg    7260 catttttta tgtgcccgac atctgtatat cttctttgga gaaatgtcta t ttaagtcct    7320 ttcctcattt cttgaattgg ctttttgtt gttgagttgt atactctata t acttaattt    7380 tcatctattc cttgggttgc cttttacct gttgatagtg tttgacacag a aaagtttt    7440 aactttggtg aagtgcagtt tgtctacttt ttctttggtt gcttgtgctt t tggtgacat    7500 atccaagaag tcactgttaa gtcgaaatca tacagatttt cccctatgtt t tctgctaag    7560 agttttatag ttttagctct tatattttgg tctttgattc tttgttgatt t ttgtctatg    7620 gtccaaggta caaatccagt gtaattcttt ggcatgtgac tattcagttc t tcaaacacc    7680 atttgctaag aagattgtcc tttctgcatt gggtggttttg ggcaccttg t tggaatcat    7740 ttgaacatat atacaaataa ttcttatctt ctattgcttt cccatttcaa tgttgggct    7800 ctctattcca ttaatctata tatgtcttta tgccagtacc acattgtttt g attattgta    7860 gctttgtagt aagtttgaaa tcaggaagtg tgagacctcc aactttgttc t ttttcaaga    7920 ttgttttggc tatttggggt ctttgagggt ccatataaat tttaggatgg g ttttttctat    7980 tttatacaaa aaccataatt gctttttatt aaggatagcg atgaatctgt a gatgacttt    8040 gggtagtatt gacagcttaa tagtaagtca gtccatcctt atttctttat a tcttttcac    8100 agttttataa aactggtatt ttttacttga ggtaaggtaa ataaactctt a gagcctttg    8160 ttttctggtt ttatgctgcc ctaggcaacc ttggctaact ttaagaatgt c atctccatt    8220 tatttattta tgccttggga gatttaggtt ccaactacat ttgcttttta a tgctctcct    8280 ttgagcagtc tcaccaccag ccacaccaac ataacatata tataacatac t ctacaggtg    8340 cactgaagaa ttcagcgcag catcccattt tgagtcctca ggaggggacta g gcagaccac    8400 agctgaagga agagggctga tcagctcttc cttttctgtct tgactctgtg c ctgcaggtg    8460 ttctttaact atttgtttgc cctgtcaaag acaaagtgca ttctcttgtg a taccagagt    8520 agttttaaa ttgaaaaagg gagagcaata ggagataaaa attatttggc t ttgttataa    8580
```

```
ttgggcatg ttaatacaaa ataaaatgaa ttatttggct gcttagcttt c tgtaatgtg    8640 taattcattt gaataatttt cagtgttagg ttgctgatct ttgtatttttt t atcctttta    8700 atttaagctg tcaattgatt cattttggtt ttgttttta tagaaactaa g ttttcaaa      8760 tcttcaaagt taccttcga caaagctttc tttaaattca ctgcaatata g ttgttgact    8820 ataatttaa gtggagctaa gtttgcctct taaaaacagg agttcattct g tgtattact    8880 gagtaattac tctgtatact gaagttcagt gcccagggct tgacagtgtt t aggatttaa    8940 catgagtgtt ctgttgtgtc acagtaatac ttgataatga gcctaaggca g atggaacag    9000 cagctcaggc attccttctt tatcactagt tttacccgca gtggtcctct t aagcttctt    9060 tgatgttgct ttgttgccat attagagtcc attaagtcct cacccttctg t ctttcaaaa    9120 aacctctgtg aaatctgttt ggctggtgaa gcattttgac tccaaagcta g tccttctct    9180 tacccacctt tttagtttac cttgctttgt ctttctgata atatgccagt a ttatcagct    9240 cacataaatt tgccaccttg ctgtgtccat tggccctggg catggctaaa t gattcaggc    9300 agtggaaata atatacttta ctctctggct cactgtaaat gtgcacagac t ccaagcaaa    9360 gctcctgtct ttcgggcttg agttttagag acaaaggttt gccatgctta c aggctgaat    9420 gttttttccct actgaacaaa ctagccagcc tttatttcaa gctgaatcac t ttgttactt    9480 acggaaggaa aaggtctaga aaggaaaac gtatcttcca tttatcctag a caaacaaat    9540 aatctaattt cctctggcag tcaaaatata gtttcaccta agccactgat g caggaagtt    9600 aggttttatg taacctctct aattggtaag taagtaggtt tgatgtctct g agataggaa    9660 gaaagaaacg aaaatgttca tgaaataat cagagtgatt tgtgttaagt g atcctaacc    9720 ttagcttgct ctgggtgcca gtgaaattaa cctcaacaat gttggttgga a gaattttc     9780 aacttaaaga agttgaagt tggggaatca aaaggcaggg attgttgttt c tatcactta    9840 gctgtaataa ccagagcctg tttagtattt gttttttaag gatgggatgt g tcttcaaag    9900 aggagacttg ccatgttcaa agcacaatta atgccatttt cctactgaag t gaacactgc    9960 cagttttaa cagtttcttt cactttcctg tgcttctgta gataaccttt t ttactgccc  10020 agttgttgga atgttacagc tggaaggga cctagaagag taattatcta a ctctgtttc  10080 cttattacac aaatgaggta gaaccagagt tttacgtgtc tatagagtnn n nnnnnnnn  10140 nnnnnnnnnn nnnnnnnnnn nnnnnnnnnn nnnnnnnca gtggcgcaat c atggctcac  10200 tgcagccttg acctcctggg ctcaagtgat ccttccacct cagcttcctg a gtagctaga  10260 actgcaggca tgcaccacca tacctggcta attttttaaa tttttttggt a gagattggg  10320 tcttgctgtg ttgccaggc tggtctcaaa ctcctgctca agtgatcctc c tgccttggc  10380 ttcccaaagt gctgggatta taggtgtgaa ccgccgtttc tggccgtatt t tttttttt  10440 ttaaactgct ttccttttttt tgtttttcct tttgctattt gccttttat a aggtagata  10500 cggtagagtt gctgttttga ctgagctttt gctggaagtc cttagctgct t ttgtcactc  10560 caaaagcagg gtgagaccaa atgaaaaaac tttcagctaa tcttcagttt t ttttttaa  10620 ttaaatggga cttggggggct gtggaagtga tattttcctt aattccccag a aaactttaa  10680 gctcgagaca gttatcatat attattgcta cctttttat tttttctga g acggagttt  10740 cgctcttacg cccagtctgg agtgaattga cgtaatcttg gctcactgca a cctctgccc  10800 cccgggttca agcgattctc ctgcctcagc ctctggagta gttgggatta c aggcgcctg  10860 ccaccatgcc cagctaattt ttgtatttttt agtagagact gggtttcatc a tgttggcca  10920 ggctggactt gaactcctga cctcaggcca tccacgtgcc ttggccaccc a cagtgctag  10980
```

-continued

```
gattataggc gtgagccacc gcgcctggcc tgttatcgct acctttaaa g aagaaagtt    11040 atagagtggc ctggccattc tctgtgacct acctttggga ctttaaaatg t ctttctagt   11100 atggtaggaa tagcaaaatc aatatgctgc cctccaattg atgctttgga a tgttctaaa   11160 cccagttttt attttggctc attgccagtt gtgctccccc tgccagctat t tttggcatt   11220 gtcatgaact tggaaattaa tgattctgct cactaggagt agaaaatttt g ttccttttc   11280 aattttagaa aagctttat gttgtttctg ggtagtctta ctagcttatt a atgcgcctg    11340 tcaaacttgt gcagtgttga aaacatgcca ttatggttga gatttcactg a actctgaaa   11400 ttccatcagt aatatgtgcc tctagccacc tgcaacagga atatcacttt t gagggttac   11460 ttcttttctt ttcttttttt ttttttttttg agacagagtc ttactctgtc a cccaggctg   11520 gagtgcagtg gcactgtgtc agctcactgc aacctccgtc tcctgggttc a agcaattct   11580 cctgcctcag cctcctgagt agctgggatt acaggtgccc gccaccacac c tggctgatt   11640 ttttatattt ttagtagaga tggggtttca ccatgttggc caggctggtc t caaactcct   11700 gacttcaggt gatccagcct cctcggcctc ccaaagtgct tgtattacag g catgagcca   11760 ccgcacccgg ccagttattt ctttggtaaa caaaaccaca gttcaaatta a atactacaa   11820 aaactgatga tattggtggt tccacccata gctgttaaaa agtgtaagcc c gaagaggcc   11880 tgggtcgact gctatttgta tttaaggatc agaaaagctt tcaggccctg t ggagtcccc   11940 agatttactg ttttctaagg gccactattt atgtataaat actaggggag g attttttttt  12000 ttcttctatg cctagtttgc ttagatgggg agggatattc ttatttaggg a aattatatt   12060 ctccttgctt aatccttgcc ttccctcaac ccctgcaca tatacacaaa a caacaataa    12120 gcacatatca cttgaaagta gtttgagaaa cctgggtatt ctgtgaggag a cacggccag   12180 ttagatggtt cttcacggaa agatctgttt tccatttaac tcctgtaaca t gaggaatct   12240 gaatctggat ctggatctgg atctggagtg tccttataga ttataattcc a tgacttgta   12300 agaaagaaag gaaattattt ggagaagatg atccagtgcc taagagctga a atcttggat   12360 ccaaatagct tgggtaccat cctttttctt ttgttgagat ggagtctcgc t ctgtcgccc   12420 aggctggagt gcagtggcag atctcaactc attgcaactt atgcctccca a gttaagta    12480 attctcttgc ctcagcctct gagtagttgg gattacagct gcccgccacc a tgcccagct   12540 aattttgta ttttagtag agatggagtt tcaccgtgtt gaccaggctg t tctcgaact    12600 cgtgacctca agcaatccac tcaccttggc ttcccaaagt gctgggatta c aggtgtgag   12660 ccactgcgct ggccaagggc accatctttt agtagttatg tagccttggg c aagttactt   12720 taacctctta gtgccagttt cttcatctgt aaaatggagg taatactttt a ttgcataga   12780 atctaacatg ccattgatta taagatacat tatttttgta ccacttaaaa a aggaaaagc   12840 gctgccatta aactaaaata taccatcatt tgtaagaatc ttcttaattt c agaggtgct   12900 aacatgtaaa aagatgtgta tcttagaatt gatgacatca taataatact t tgataggat   12960 tgttgtaagg attaagtgac tcaacattta taaagaactt agaacagtgc a tggcacata   13020 gtaggcaata tttatgtgtc atttattatt attgctatta gtgttaccta t tattttctt   13080 tttgaaccca cttattgcct aattagtcat agtttgacaa ttgcccttgt a ttccaccat   13140 gtcaaatata aatttacata gatgagtatg tactttact tattgagaaa c agtgtaata    13200 tataatatac tcaattctgg agccagattg cagggattca aatcctagct c tgccactta   13260 tttgactgtg actctaggcc aataacttaa tctttctttt tctcagtttc t tcttctgta   13320
```

```
atgggataa taattctatt ttagatgtgt tcgtatatat aaacgtctga g ttatggatt      13380 accttagtca tctctttaaa gttccctagc attttatttc tcacttggac t gttaatgaa      13440 tatttctaaa aagcacacta agagttcaaa gttttaaaat aatggtaaca t aatactgtt      13500 attatatcta acacctacta gtatttacca tgtgccatgc actggtctaa a agctttcat      13560 atatttattt aagcttcaca acaactctat gtggtgggaa ctcttactgt c tccatttta      13620 tagatgagga acctgaggca cagagagatc aagtaatata cctgcagcta t taaatgatg      13680 gaactaggat tcagaccctg acaggctggc tctagagagt gtgctgtcaa c accatgtct      13740 cttcagaagg catttctttt tctttttttt ttttccagaa ggcatttctg t catgaaggg      13800 gttatttatt gaccagggct tttttttttt tttttggact gtcttgggtc t cctaggctg      13860 gagtgtagtg gtgtgatctt ggcttactgc aacctctacc tcctgggttc a agcgattct      13920 tttgtctcaa cctcctgagt agctgggatt acaggcgccc accaccacac c tgactcatt      13980 tttgtatttt tagtagattt ggggtttcac catattggcc aagctggtct t gaacttctg      14040 acctcaggtg atccacccgc ttcggcttcc caaagtgctg ggattacagg c atgagccac      14100 tgtgcccagt tgaccaggcc ttttaattga ttttttttttt ttatgattga a atggtgcta      14160 ggaataataa taaaaaaaat ctattatccc ttatctgtga ttgcaaaatt c agaaagctc      14220 tcataaatga aaatttttct ttaagttggg tataaattca tttaattggc a agacctgac      14280 ttgaaccatt gttaagctat ttgaagtctt tatttagcca acttagtatg a ctgttccca      14340 tgttttgttg cagaaatatt aatgtgtttg attatagtgc actgccctga a ctccactgg      14400 gattattata taatgtgtac tttgtgttct gcattacctt tctgaaattc a aaatattct      14460 gaattccaaa acacatctgg ccctgagctt cagatgatgg attgtatacc a aagatttt      14520 tttccatttc attgaataaa tgttccttta gctaatacta aaacaggact t agtcatgta      14580 gttaattttc ccaaataatg ttttttttttt tttaatctga tattttttgt t tttgctaga      14640 gctcctgaaa ttattcttgg gttaccattt tgtgaagcta ttgatatgtg g tcactgggc      14700 tgtgtgatag ctgagctgtt cctgggatgg cctctttatc ctggtgcttc a gaatatgat      14760 caggtaaaag tgtttatttg aatggaaata gaatgcaaat agttacttgt g aattagatt      14820 ctggagaaag agaagtacta agtactactg aagtatttag ataataggga a agagtagtc      14880 caattgctac taaagaactt tttaaagaat agtataattt tctcttcctg c ttcttaggc      14940 taaagtatgt ttgcaattct ataataaaaa aaagaatttt attttatatt a aggttgata      15000 ctttgctaga tctgtaatga tttattagag acttaacttt cattaactta t gtgctttgt      15060 gagttaggaa agtagagtaa agatgaggaa ctggaatttt aaaagagaac t tctacttac      15120 tcggagctat tataatttac ttttacgcat gacacactga agtactttct t cagactgaa      15180 acacttcagg tcccagaagc tgtgacatac tgggtcgcta agataggatt t agaaaggaa      15240 atcatcctga gttgtagtaa tatatgatct gtatctaaaa atagacaaac t taggagata      15300 tggtataatt tcctaaggaa ttggtccgtt aagggaaaat gttttactat g gaagtaaat      15360 tgtgaattct catttcttgt tatttttttct ttttcttttt tatttgtttg a gatggagtc      15420 ttgctctgtc acccaggctg gagtgcagtg gcgcgatctc ggctcactgc a acctctgcc      15480 tccctggttc aagcgattct cctgcctcag cctcctgagt agctgggatt a caggtgcct      15540 gccaccatga ccaactaatt tttgtatttt ttagtagaga cggggtttca c catgttggc      15600 caggctggtt tcgaactcct gacttcaggt gatccacctg cctcagcctc c caaagtgtt      15660 gggattacag gtgtgagtca ccgtgcctgg ccttcttctt attttttaaa a atgttcctg      15720
```

-continued

```
cccttatga tgtaagctcc ttgagggtag agattgtttc acatcaccag t gtatcctca   15780 gctcctaaca ctgtgtctgg tacacagtaa gtacaccagt ttttttgttg t ggttttaa    15840 gtttttattt ttttagagac agagtcttgc tcagtcaccc aggctggcat g taggcctgt   15900 cacagcttac tgtaacctct agctcctggg cttaagtgat cctcccacct c agcctccca   15960 ggtagatggg actataggtg catgccacct tgcctagcta attcttttat t ttttgtaga   16020 gtcgggatc ttgctatatc agcctagggt ggtctcaaac tcccaggctc a agctatcct    16080 cctaccttgg cctcccaaag tactgggatt acaggtgtga gccaccatgc c tggcctata   16140 ttgtcaaata tctttacttg tccgtaaata cacttctacc ttgtcattta c aatgtctgc   16200 atggtatttt ggtttccagc tacaggattt agaaaggaag ttatctgagt t gtagtagat   16260 tccacagatt tgaagtatta gaagtcaaca ggaaaagcaa aaagattat a gccaaaatt    16320 ttcaaaactg gatttccttg taaataatag atacagtagc tgtggatgga t tagtatata   16380 taggtattta cagataaatt tcagttgtat tgattaaaga tttgatttct t cctttgcct   16440 aaagttaatg atgttttagt gtaaaagcct ttaataattt cccttttcac t ccaaatagt   16500 tgtttgatgg ttttgatgtt tcagattcgt tatatttcac aaacacaagg c ttgccagct   16560 gaatatctta tcagtgccgg aacaaaaaca accaggtttt tcaacagaga t cctaatttg   16620 gggtacccac tgtggaggct taaggtctgt cttccctact atgcttccga c tcctgtact   16680 ccacccctca ctccccaatt ttgaattcaa agtttagtta ttaaattctt c aggtagaga   16740 agggaaagga gaggggggaag cattttgaaa aattatttct ttgtacctgt t tggccttat   16800 cctcagttga aaaacaaaac attaattgct agttcagttg gctgaggtta t tttgtatat   16860 gttcaatcca cagctgatag aaagtttgga gggtagtgct caccattaag c gatagaact   16920 agagacatat agtaatgact gatttttaga gaattctcaa tgaacatgat a aaatcacaa   16980 attttctaac tgcccacatt caggacttct atattttttc ttgaaacaaa t acctgcttt   17040 ttacttctga gcctactctg tcaggttcag aaatatctga gtaatttgac t aaccctgtg   17100 actgtgtgtc tgagtctgtt gaacagttag catttgagat atcgatttat t tgaaagtag   17160 ctttaagaga acaatggtag tgtccccttt tacctgacat tctttaggaa c tgtgctgta   17220 tcattacttg catgtttatc actgttgaaa gggtagctag atatcaaggt c acatctctc   17280 cactggaaga ttttctggtt gtgaattact ttcatgtttg ccatctatgg t tggcaaggt   17340 gaccacactt gtctcttgta ttctggcttt ggttttgaat aaaatgtgaa a ataacatac   17400 agatggaatt taaggaggaa aatctttatt ttatagacac ctgaagaaca t gaactggag   17460 actgaataa aatcaaaaga agctcggaag tacattttta attgcttaga t gacatggct   17520 caggtgagta cggaaagttt cagaaagtca gacatttatt tttaatcaga g acacttctg   17580 ttgattatac taaagacaaa tttaatgtta tctttctagt atttgttttc a gttttata    17640 aaaaatgcat taatattcca ccatgtagta aaggaacatt taaatcctaa c caagtatat   17700 ttttagaatt acatatttct ctcttgcttt acttgtcttg ttacatagca g tgttttaaa   17760 atattactta tgaaagtttc ttgtcccatt ttctctatta aatacttaag a attatattt   17820 attgagcgcc tattatgtta cgaactctga acacttcaca cttatgtcat t taattttt    17880 caacagtaga agcttttata tttaggtagt aacaatcact attgcttagc t acttgttcc   17940 attttttttt tttttttttt tttttttgag acagagtctc actctattgc c caggctgga   18000 gtgcagtggc gtaatctcag ctcactgcaa cctctgcctc ccgggttcaa g cgattctcc   18060
```

```
tgcctcagcc tcccaagtag ctgggattac aggcacgtgc caccatgccc g gctaatttt    18120 tgtattttt ttagtagaga cggggttttg ccatgttggc caggctgggt c tcaaactcc    18180 tgacctcagg tgatccacct gccttggctt cccaaaatgc tgggattaca g gcatgagcc   18240 accgcgccca gccccaaat ttttaatgac aagaaattgt ttagctttct t ctaccactc    18300 aatttagatg aagatttta ttaaacagca taaaagagc ttcctcctct g aaaatgatt   18360 agattttcat aaaagaatt tccccaggtt tctcttttga ttacatatat a cacacacac    18420 atagttgga gggaaagcag ctatgtagtg tcagtgccaa aggttaagtg a agaagtata   18480 attctgaatt ttctttggaa ggtgaatatg tctacagacc tggagggaac a gacatgttg    18540 gcagagaagg cagaccgaag agaatacatt gatctgttaa agaaaatgct c acaattgat  18600 gcagataaga gaattacccc tctaaaaact cttaaccatc agtttgtgac a atgactcac  18660 ctttggatt ttccacatag caatcagtga gtatggaata ttctgggct t tgccatgt    18720 ggttctttgt tgagttaccg ccttatcaat ggcactatca aatgagcccg c cactttggt  18780 gcttataaat ctggctcagc agtgcttttc tttctcattg aaacatcata a gataaaaat   18840 tagatgtgta ttttcttcc ctatgattat acaaattctt gatttatttt a tctgaaagt   18900 gattgggaaa aaaagctttg atccatgttc atcttgagtt atttgctgtc t gtttaaatc   18960 tcagcattca tttaatgaat ctttaatctc cttttcagtg ttaagtcttg t tttcagaac  19020 atggagatct gcaagcggag ggttcacatg tatgatacag tgagtcagat c aagagtccc  19080 ttcactacac atgttgcccc aaatacaagc acaaatctaa ccatgagctt c agcaatcag  19140 ctcaatacag tgcacaatca ggtattcaat aaataatttt ggaaactcaa g cttaagtgg  19200 gatagaaact agtaagaata cagggcaagg taaagaacca attttttgttt t ggtggtctt   19260 gttgcttctt agaaattctc cacttgacaa agttgatgg aaaacagggt a gactgataa    19320 tacttaccag gcacaggcta actaaagtta aatataaagg cctaatccat g ccctcatat  19380 gttcagcatc gtcaaataaa tggggtctga ctattatgct acttactgct g ttagttta   19440 ctgacttag ccaaatgact ttctccctgt taggagaagg attttatatc t cttgttact   19500 gtattgaaag gtttccagtc attaacttta agggtggttt tgcatttgtt t gctagccag   19560 tgatatttgc atttaggttt atttctgaag atgtaagctt cccagtttct t ggctgggtc  19620 tactttttta atggaagagc ctatgagatt tggtgggatc ttccatccag t aattttttg  19680 tgcagaagta gttggggttt tgtagccac agccaacata ggaccattcg t ttttttttt   19740 tttatttgct tatttgacca tataatatgc cttcaattta gggactaggg a agtttctta   19800 agcagagagt tatttcagag gcagttaaca ttacattta aaacattatt c tacgtttt    19860 ctggataaat tctgtatata taaaattatt gtgtgtctct acttaataca a gtgtacaaa    19920 tataatcctt tgtttttag gccagtgttc tagcttccag ttctactgca g cagctgcta   19980 ctcttttctct ggctaattca gatgtctcac tactaaacta ccagtcagct t tgtacccat  20040 catctgctgc accagttcct ggagttgccc agcagggtgt ttccttgcag c ctggaacca   20100 cccagatttg cactcagaca gatccattcc aacagacatt tatagtatgt c cacctgcgt   20160 ttcaaagtaa gtggggaaac tcctgtatca tatggtattg tatcagacct a cctgcttta   20220 ggcagctcta gttgtttagt tctgatcttt acaagtttaa actctgtctc t gatgaagaa   20280 ggtaactaaa attgggtaat atcgcaaaat ggattttctc ttttttacata g gctatttat   20340 ctaattatga tgctatctga tgcattgtaa gagctcactt tatgttcct t aattgaatt    20400 gcctgatacc agttttcttg cccattgagt ccttgtgtca atgtcgtacg t cttgtataa   20460
```

```
gcatgtatct gtcaatatgc aaaatctata caacttgaaa aaatttgttg t aagcagaat    20520 tgctaaatan nnnnnnnnnn nnnnnnnnnn nnnnnnnnnn nnnnnnnnnn n nnnnnnnnn    20580 nnnnnnnnnn nnnnnnnnnn nnnnnnnnnn nnnnnnnnnn nnnnnnnnnn n nnnnnnnnn    20640 nnnnnnnnnn nnnnnnnnnn nnnnnnnnnn nnnnnnnnnn nnnnnnnnnn n nnnnnnnnn    20700 nnnnnnnnnn nnnnnnnnnn nnnnnnnnnn nnnnnnnnnn nnnnnnnnnn n nnnnnnnnn    20760 nnnnnnnnnn nnnnnnnnnn nnnnnnnnnn nnnnnnnnnn nnnnnnnnnn n nnnnnnnnn    20820 nnnnnnnnnn nnnnnnnnnn nnnnnnnnnn nnnnnnnnnn nnnnnnnnnn n nnnnnnnnn    20880 nnnnnnnnnn nnnnnnnnnn nnnnnnnnnn nnnnnnnnnn nnnnnnnnnn n nnnnnnnnn    20940 nnnnnnnnnn nnnnnnnnnn nnnnnnnnnn nnnnnnnnnn nnnnnnnnnn n nnnnnnnnn    21000 nnnnnnnnnn nnnnnnnnnn nnnnnnnnnn nnnnnnnnnn nnnnnnnnnn n nnnnnnnnn    21060 nnnnnnnnnn nnnnnnnnnn nnnnnnnnnn nnnnnnnnnn nnnnnnnnnn n nnnnnnnnn    21120 nnnnnnnnnn nnnnnnnnnn nnnnnnnnnn nnnnnnnnnn nnnnnnnnnn n nnnnnnnnn    21180 nnnnnnnnnn nnnnnnnnnn nnnnnnnnnn nnnnnnnnnn nnnnnnnnnn n nnnnnnnnn    21240 nnnnnnnnnn nnnnnnnnnn nnnnnnnnnn nnnnnnnnnn nnnnnnnnnn n nnnnnnnnn    21300 nnnnnnnnnn nnnnnnnnnn nnnnnnnnnn nnnnnnnnnn nnnnnnnnnn n nnnnnnnnn    21360 nnnnnnnnnn nnnnnnnnnn nnnnnnnnnn nnnnnnnnnn nnnnnnnnnn n nnnnnnnnn    21420 nnnnnnnnnn nnnnnnnnnn nnnnnnnnnn nnnnnnnnnn nnnnnnnnnn n nnnnnnnnn    21480 nnnnnnnnnn nnnnnnnnnn nnnnnnnnnn nnnnnnnnnn nnnnnnnnnn n nnnnnnnnn    21540 nnnnnnnnnn nnnnnnnnnn nnnnnnnnnn nnnnnnnnnn nnnnnnnnnn n nnnnnnnnn    21600 nnnnnnnnnn nnnnnnnnnn nnnnnnnnnn nnnnnnnnnn nnnnnnnnnn n nnnnnnnnn    21660 nnnnnnnnnn nnnnnnnnnn nnnnnnnnnn nnnnnnnnnn nnnnnnnnnn n nnnnnnnnn    21720 nnnnnnnnnn nnnnnnnnnn nnnnnnnnnn nnnnnnnnnn nnnnnnnnnn n nnnnnnnnn    21780 nnnnnnnnnn nnnnnnnnnn nnnnnnnnnn nnnnnnnnnn nnnnnnnnnn n nnnnnnnnn    21840 nnnnnnnnnn nnnnnnnnnn nnnnnnnnnn nnnnnnnnnn nnnnnnnnnn n nnnnnnnnn    21900 nnnnnnnnnn nnnnnnnnnn nnnnnnnnnn nnnnnnnnnn nnnnnnnnnn n nnnnnnnnn    21960 nnnnnnnnnn nnnnnnnnnn nnnnnnnnnn nnnnnnnnnn nnnnnnnnnn n nnnnnnnnn    22020 nnnnnnnnnn nnnnnnnnnn nnnnnnnnnn nnnnnnnnnn nnnnnnnnnn n nnnnnnnnn    22080 nnnnnnnnnn nnnnnnnnnn nnnnnnnnnn nnnnnnnnnn nnnnnnnnnn n nnnnnnnnn    22140 nnnnnnnnnn nnnnnnnnnn nnnnnnnnnn nnnnnnnnnn nnnnnnnnnn n nnnnnnnnn    22200 nnnnnnnnnn nnnnnnnnnn nnnnnnnnnn nnnnnnnnnn nnnnnnnnnn n nnnnnnnnn    22260 nnnnnnnnnn nnnnnnnnnn nnnnnnnnnn nnnnnnnnnn nnnnnnnnnn n nnnnnnnnn    22320 nnnnnnnnnn nnnnnnnnnn nnnnnnnnnn nnnnnnnnnn nnnnnnnnnn n nnnnnnnnn    22380 nnnnnnnnnn nnnnnnnnnn nnnnnnnnnn nnnnnnnnnn nnnnnnnnnn n nnnnnnnnn    22440 nnnnnnnnnn nnnnnnnnnn nnnnnnnnnn nnnnnnnnnn nnnnnnnnnn n nnnnnnnnn    22500 nnnnnnnnnn nnnnnnnnnn nnnnnnnnnn nnnnnnnnnn nnnnnnnnnn n nnnnnnnnn    22560 nnnnnnnnnn nnnnnnnnnn nnnnnnnnnn nnnnnnnnnn nnnnnnnnnn n nnnnnnnnn    22620 nnnnnnnnnn nnnnnnnnnn nnnnnnnnnn nnnnnnnnnn nnnnnnnnnn n nnnnnnnnn    22680 nnnnnnnnnn nnnnnnnnnn nnnnnnnnnn nnnnnnnnnn nnnnnnnnnn n nnnnnnnnn    22740 nnnnnnnnnn nnnnnnnnnn nnnnnnnnnn nnnnnnnnnn nnnnnnnnnn n nnnnnnnnn    22800
```

-continued

```
nnnnnnnnnn nnnnnnnnn nnnnnnnnnn nnnnnnnnnn nnnnnnnnnn n nnnnnnnnn    22860
nnnnnnnnnn nnnnnnnnnn nnnnnnnnnn nnnnnnnnnn nnnnnnnnnn n nnnnnnnnn    22920
nnnnnnnnnn nnnnnnnnnn nnnnnnnnnn nnnnnnnnnn nnnnnnnnnn n nnnnnnnnn    22980
nnnnnnnnnn nnnnnnnnnn nnnnnnnnnn nnnnnnnnnn nnnnnnnnnn n nnnnnnnnn    23040
nnnnnnnnnn nnnnnnnnnn nnnnnnnnnn nnnnnnnnnn nnnnnnnnnn n nnnnnnnnn    23100
nnnnnnnnnn nnnnnnnnnn nnnnnnnnnn nnnnnnnnnn nnnnnnnnnn n nnnnnnnnn    23160
nnnnnnnnnn nnnnnnnnnn nnnnnnnnnn nnnnnnnnnn nnnnnnnnnn n nnnnnnnnn    23220
nnnnnnnnnn nnggattaaa nnntgaataa ngctgggcac nnnggctcac n nnntgtaatc    23280
nnnnnnnnnn nnnnnnnnnn nnnnnnnnnn nnnnnnnnnn nnnnnnnnnn n nnnnnnnnn    23340
nnnnnnnngg nnnnnnccg nctctactga nnnnnnnnnn nnnnnnnggg n nnnnnnnnn    23400
nnnnnnnnnn nnnnnnnnnn nnnnnnnnnn nnnnnnnnnn nnnnnnnnnn n nnnnnnnnn    23460
nnnnnnnnnn nnnnnnnngc nnnnnnnnca nnnnnnnnnn nnnnnnncca nnnnnnnnnn n nnnnnnnnn    23520
nnnnnnnnnn nnnnnnnnnn nnnnnnnnnn nnnnnnnnnn nnnnnnnnnn n nnnnnnnnn    23580
nnnnnnnnnn nnnnnnnnnn nnnnnnnnnn nnnnnnnnnn nnnnnnnnnn n nnnnnnnnn    23640
nnnnnnnnnn nnnnnnnnnn nnnnnnnnnn nnnnnnnnnn nnnnnnnnnn n nnnnnnnnn    23700
nnnnnnnnnn nnnnnnnnnn nnnnnnnnnn nnnnnnnnnn nnnnnnnnnn n nnnnnnnnn    23760
nnnnnnnnnn nnnnnnnnnn nnnnnnnnnn nnnnnnnnnn nnnnnnnnnn n nnnnnnnnn    23820
nnnnnnnnnn nnnnnnnnnn nnnnnnnnnn nnnnnnnnnn nnnnnnnnnn n nnnnnnnnn    23880
nnnnnnnnnn nnnnnnnnnn nnnnnnnnnn nnnnnnnnnn nnnnnnnnnn n nnnnnnnnn    23940
nnnnnnnnnn nnnnnnnnnn nnnnnnnnnn nnnnnnnnnn nnnnnnnnnn n nnnnnnnnn    24000
nnnnnnnnnn nnnnnnnnnn nnnnnnnnnn nnnnnnnnnn nnnnnnnnnn n nnnnnnnnn    24060
nnnnnnnnnn nnnnnnnnnn nnnnnnnnnn nnnnnnnnnn nnnnnnnnnn n nnnnnnnnn    24120
nnnnnnnnnn nnnnnnnnnn nnnnnnnnnn nnnnnnnnnn nnnnnnnnnn n nnnnnnnnn    24180
nnnnnnnnnn nnnnnnnnnn nnnnnnnnnn nnnnnnnnnn nnnnnnnnnn n nnnnnnnnn    24240
nnnnnnnnnn nnnnnnnnnn nnnnnnnnnn nnnnnnnnnn nnnnnnnnnn n nnnnnnnnn    24300
nnnnnnnnnn nnnnnnnnnn nnnnnnnnnn nnnnnnnnnn nnnnnnnnnn n nnnnnnnnn    24360
nnnnnnnnnn nnnnnnnnnn nnnnnnnnnn nnnnnnnnnn nnnnnnnnnn n nnnnnnnnn    24420
nnnnnnnnnn nnnnnnnnnn nnnnnnnnnn nnnnnnnnnn nnnnnnnnnn n nnnnnnnnn    24480
nnnnnnnnnn nnnnnnnnnn nnnnnnnnnn nnnnnnnnnn nnnnnnnnnn n nnnnnnnnn    24540
nnnnnnnnnn nnnnnnnnnn nnnnnnnnnn nnnnnnnnnn nnnnnnnnnn n nnnnnnnnn    24600
nnnnnnnnnn nnnnnnnnnn nnnnnnnnnn nnnnnnnnnn nnnnnnnnnn n nnnnnnnnn    24660
nnnnnnnnnn nnnnnnnnnn nnnnnnnnnn nnnnnnnnnn nnnnnnnnnn n nnnnnnnnn    24720
nnnnnnnnnn nnnnnnnnnn nnnnnnnnnn nnnnnnnnnn nnnnnnnnnn n nnnnnnnnn    24780
nnnnnnnnnn nnnnnnnnnn nnnnnnnnnn nnnnnnnnnn nnnnnnnnnn n caagttttt    24840
tttccaccta gtggattaaa aagtgaataa tgctgggcac agtggctcac a cctgtaatc    24900
ccggcacttt gggaggccaa gatgggcaga tcatgaggtc aggagttcga g accagcctg    24960
gccaacatgg tgaaaccccg tctctactga aaatataaaa attagacggg c gtggtggcg    25020
cactcctgta gtcgcagcta cttgggaggc tgtggcagaa gaatcgcttg a acttgggag    25080
cagagtttgc agtgagccca gatagcatca ctgcactcca gcctgggtga c agagcgaga    25140
ctccatctca naaaaaaaaa aaaaaaaaaa aaaaaaaatg aaagtgaatt t aatttacta    25200
```

```
agtgaagatt tttttgtttt tgcctgtact cttaatggag atgggatgaa t attgtgttt   25260 taaattttgt agcataaaaa aaatttagaa ttcttttaaa ccatccctca c tatatcaaa   25320 catctttcca ttaacctaac ctgaggggaa gtctcccttt tcttaacttc c aagacttct   25380 atgaatgaaa cttctttgtc ttaagtgtct aggattaaaa cctgaacagt g gattatttg   25440 aacagagaag ctgaaaacaa aataatctta aaacagtact cccagacctt g caaaactat   25500 ttaactgtga tgctgttttc aatagctgga ctacaagcaa caacaaagca t tctggattc   25560 cctgtgagga tggataatgc tgtaccgatt gtaccgcagg caccagctgc t cagccacta   25620 cagattcagt caggagttct cacgcaggta aaagctagag caatgtggat a ctcagtatt   25680 gctaaacact attgagattc agatattttg tcctagaaaa tggtatttcc t ttgactata   25740 agatctttct tggtcatgat tcagtggact aaaatgaaa catctctatg g aacaatata    25800 ctaattccta acactattgc aactctgcca ttgtcttcct tagacttgca g ggaaaaaat   25860 atccagacat tcttgagaaa tggtcttctg agtaagttta ctctaatttt g cggggtgaa   25920 gcgttttttt ttgttgttgt ttgttttttta aatgttggag ctcatataaa g ataagtata   25980 tatgtagcat tttgattcta aaatataagc ttccacttt gcacccttg t gtcccttt   26040 gctcactctt ttagaattc atcacagttg agaggctgga tcacatcagg a tgcctcttc   26100 acatattaca ttccttcatt ccgtgtgttt aaccatattg tagaaagctt t aaaacttta   26160 tacttgctat ggaacattcg actaagatga tagagaaaat tgtaaagtat t taaatagca   26220 acaaacagta tattttatat tttatatata aatgtttgtg gcctatgaca c ataggaaat   26280 tctcaaatcc aaaaactcta ttttgtgaac aggaggaaga attcttaata a atgtctctg   26340 tttcatagaa ctgatcccct gaatctagcc caaggaggat tcctatactt c tttgtttta   26400 ggccattggc atttgacttt gtgggccaat gccatacaaa gttgaagggg g aaagttgtg   26460 tttggtatat gcattttaga tgctatcaaa ttactgttca ttgtcagtaa t aacttgggg   26520 ggaatgagaa ccctctgaa tccagatatc ctgcctccgt gtttgtttca c tcacctgcc   26580 taatctacgt ttcagggaag ctgtacacca ctaatggtag caactctcca c cctcaagta   26640 gccaccatca caccgcagta tgcggtgccc tttactctga gctgcgcagc c ggccggccg   26700 gcgctggttg aacagactgc cgctgtactg gtaattcccc tcacttgatt g tgttactaa   26760 cggagtttct ttggtttctt tcttttttgt ttttcctgt ttgtttttgt t ctgttttt    26820 tctggtttat ttttcaaaaa aattttttag cttagtcttt gcagagggca t ggaagcatg   26880 tgccatcttg tggctgtgtt cttgctacat cttttaatgt ctcattgttt t cctcccca   26940 acatttgctg tagcactgtc tgactgatgg ttatgtggc ctgtaaggag c cagatccct   27000 tgattcttct tgccagcct agtgtgataa aagctctcga tgtagcctca g aagagcttc   27060 aacactgtta cttgtttttct gccttttacc ctctgatcct tgagaatgaa g gaaatggcc   27120 tttaatttgg ctcagctaca ggtacccgga tggccaaaat tgagctcgtt g gcaagatag   27180 ctttctcctt tttttgctgt tttaaggttc taaaactttt ctgcatgtgg a aatgcttaa   27240 gatgctctta atttattgct ttctcagttg atactaacca tccttctatg g acacatgaa   27300 gatagctctt tttgccactc atgatcagtg gcagcttata tcttacattt a aagatattc   27360 cctttagaat gtagatcata ttgtaggtca tattgttggt tgaaattaaa a gtggacaca   27420 ttttttaggag ttttgggagg aattaattat tttacaaata ggtctttata c aaaggttga   27480 aagtatggcc aacaaactat gcaaatacaa tatctttgtt attaaaagtc a tggggaata   27540
```

```
gttacttaat gtagctgcaa ttgtagtact gggcttagag atagaaaaaa c aaccaagac   27600 tttgaggtgt gtttcaggat ttgtaacctt aagagtgatt ttttggatgt g ttttggttt   27660 atatggggag ttagaattgt ttattggata tccagcattt tctcatttga a atttaaaat   27720 taggtaagca tccaaaaacc tgaaaggcac tattgaatcc tgttatttct c tgttttcaa   27780 agttgcttta aatttctttt gttgtttctt aagtattcat gtgagtgaaa a cacttccag   27840 aaacatactt tggttggaat ttggttttca ttttaaaagt ctttgtcact t ccagattaa   27900 ttttcttgta agcagaaaac ctgagtgtga gggagtcaga tatatttcca a cttgattga   27960 tccaagccaa tggttttaac tcactcatct gtagtttcga ggttggaatg t tagttgaca   28020 cttctccttt gctgcttctc ttaagtttgc actagccatt tgctaagctt t gcatatttt   28080 tgttcttcct ctgtcaaaac agttcgtcgc ttggaacgcc agatttctgc c tcacattgg   28140 aatgttattt cttgctttgt attaaactac atgctttgtc ttgtgcaggt g ttggcttat   28200 ggaaagacgc atggtgtgac ttaacatact tctttatttt tttgttttgt t ttattttgt   28260 tttaaattct gcttatggta gcagacgtgt ttgcagtttc tctgctttga a ggcttcttg   28320 tttggaacca gtatttgtaa caagtagatc tgttacttgc agaaatattt t taaaacagt   28380 gtgttgatgg ccttgcaatt tgaaattcaa gaaacagaac catatgtacc c aagcattgt   28440 aggtaattgt actgcagaat tcaagtttaa aaaggaaact tccaaatccg t tcccatttt   28500 ttttttcaaa aaatgccaga atttctgtga ggaagaagta cagaaaacat t tgttgctca   28560 gtttattgca agtgacatgg ctttttttaaa actagaaatc atgtattttc t tgtagtgat   28620 tagtttttat gtggaaatat tcctgcaaat gatacataaa aacatatttt a ggtaactat   28680 tagaaacaaa gtatgatgct ttctgcttct aaaacatctt acttttgcc t tattttgaa   28740 attccattat gtggctataa atgatgaatt agcttttttct tgctggcata a gattttttc   28800 cccaaaagga ttaggccttt ggtcatccac atctggctcc attttccaaa t actacccttt   28860 ttaaaaaagg gaacagttct gccttttgtt ttatgggttg aattgatctg a taccttatc   28920 tgattggcag tcagattaaa aaattttaat ctccagggag tcctcttaac t ctttctagg   28980 gatttatttt agaattgttg caaaaatgaa actccagcat ttaaccagct c ttatctctg   29040 aactctcaga ctcctttttct ctacagtata atagaagctc ttaaccgcag g gatcttctt   29100 ttctttaata cccgggtggt caggttatgg gggtgagcaa gagaaagcag t atgttttct   29160 ttccccattc ataagacttg tagcttgagc ccctctgacc tttctttttt a atctctgca   29220 agttaacaat ctacaagcaa cttcttttaa gatatgaatt tttctttctt t aaaaaaaca   29280 gaagaaaaag ccaagaatga atcaagtctg gatgttttttt atgtgtgttt c cttacagca   29340 ggcgtggcct ggagggactc agcaaattct cctgccttca acttggcaac a gttgcctgg   29400 ggtagctcta cacaactctg tccagcccac agcaatgatt ccagaggcca t ggggagtgg   29460 acagcagcta gctgactgga ggcaagtgtc ctgtgttact ctgggagatt t gtaagggcc   29520 gatcccatag ggtgggagca cttggtaata aggagagaga ctagtaagaa a ataaaggaa   29580 aatttgacac tgttggaatc ctttaagaac ccatatcagg ctaggagatg g tgttataag   29640 aaaactttga atataggaaa gcagtaggtt ctgaaggtca ggaatcattt c ttctagatt   29700 ttttaaagag agtcttaagt gattagaaac catacagtga gatcctaaag c cttgtaatc   29760 taggtccccca actttatctt ttataatgaa aattcttttt ttctaatgtt t aattttgt   29820 gattacatac taggtatata tatttatggg gtacatgaga tgttttgaca c aggcatgta   29880 atgtgaaata agcacatcat ggaaaagggg gtgtccatcc cctcaagcat t tatccttg   29940
```

```
agttacaaat aatccaatta cactctttaa gtcatttaaa aatgtacaat t aagttatta  30000
ctgactataa tcacctattg cgctatcaaa tagtagttct tattcttttt t tttttttt   30060
tgtacccatt aaccatccct acctccccac tagccctcca ctactcttac c agcctctgg  30120
taaccatcct actctctatg tccatgaatt aaattgtttt gattttaga t cccataaat   30180
aagtgagaac atgtggtttg tctttctgtg tctggcttat ttcacttaac a tgatgatct  30240
tgagttccat ccatgttgtt gcaaatgaca acgtgtactt tttgtggctg a gtagtactc  30300
cattgtgtat atgtaccata ttttctttat ccattcatct gttgatggac a cttaggctg  30360
cttccaaatc ttactgtgaa cagtgctgca acataggagt gcaggtatct c tttgatata  30420
ctgatttcct ttcttttggg tatataccca gcagtgggat tgctggatca t atggtagct  30480
caatttttag ttttttacagg aacctccaaa ctgttctcca taatagttgt a ctaacttac  30540
attcctacca acagtgtaca attgttccct tttttccata tccttggcag t gtttattat  30600
tgcttgtctt ttggatataa gccattttaa ctggggtgag ataatatctc a ttgcagttt  30660
tgatctgcat ttctctaatg atcagagatg ttgagcacct tttcatatgc c tgtttgtca  30720
tttgtaagtc atcttttgga aaatgtctat tcaattcttt tgcccatttt t tgatcgtat  30780
tattagattt ttttccatag agttgtttga gctgcttacg tattctggtt a ttaatccct  30840
tatcagatgg taggtgctca actttaaaaa aataaaatgc agctgcattt t ggctaattg  30900
cttttgatgt ctgtttggtc ctgattcttc agtggttttg gaattcactc t tctctttct  30960
ttctgttggt acaggaatgc ccactctcat ggcaaccagt acagcactat c atgcagcag  31020
ccatccttgc tgactaacca tgtgacattg gccactgctc agcctctgaa t gttggtgtt  31080
gcccatgttg tcagacaaca acaatccagt tccctccctt cgaagaagaa t aagcagtca  31140
gctccagtct cttccaagtg agtctgtgtt acagctgata gttaaaactg t gccagtttg  31200
agagatatgt tgccttgcat ttggaatatt gtatagacat ataatataga t atgaagcag  31260
caagtagctg ccaaattgag gaagagcaaa tcatttcatc tgggcatgta c accaggtgt  31320
gtcctggttt tatgatggtc ctttgtctct gctgccactt tgaatctagg g catttatg   31380
atgtttttat tttactttac agagtgaaat ttaatcctgg gataaagggc t tataaaagt  31440
aaaatgtctt ttgtatttg gtgttcttgt ccctggaaac tcttgccagc a tggtgctta  31500
ttttcactgg aacttatata gttaaatgta tttgcttaat gattatgtaa a aaggaatca  31560
atgagtaaat tggaaagcag tctggggaaa agatacacaa tttggaaggc c aaggactga  31620
atcatctttc catgtgaact tttcctacag gtcctctcta gatgttctgc c ttcccaagt  31680
ctattctctg gttgggagca gtcccctccg caccacatct tcttataatt c cttggtccc  31740
tgtccaagat cagcatcagc ccatcatcat tccagatact cccagccctc c tgtgagtgt  31800
catcactatc cgaagtgaca ctgatgagga agaggacaac aaatacaagc c cagtaggta  31860
agataagtga atggttcctg gctctattgg ttttagactg ttggcctcag g caagtgggc  31920
ccagtttggc ctgtgaaaga aaggaccggt ggggcatggt ggctcacgcc t gtaatccca  31980
gcactttggg aggttgaggc cagcagatca cctgaggtga ggagttcaag a ccagcctgg  32040
ccaacatggc acaaccctgt ctctactaaa aatacaaaaa ttagcagggc c gtggtggca  32100
catgtttgta tcccagctac tcgggaggct gaggcaggag aatcacttga a cccaggagg  32160
cggaggttac agtgagctga gatcgtgcca ctgtactcca gcctgagtga c agagcaaga  32220
ctgcatcccc tcccgccccc acccaaaaaa aagggccgaa gaaaaannnn n nnnnnnnn   32280
```

-continued

| | | | | |
|---|---|---|---|---|
| nnnnnnnnnn | nnnnnnnnnn | nnnnnnnnnn | nnnnnncaat | ggtaagaaat a aaggctagg | 32340 |
| aaaaattcaa | atttactgac | gccagaatag | ggtgagttga | gtcaccagtt a ttaacttgc | 32400 |
| aggagtgggg | aaccctatga | tctcttgatt | ctccctcttc | ctgtcatact t acaagcaaa | 32460 |
| atgctgttac | ctgagccaga | ttaggatcta | tcttgctaag | aggcagaagg a ggggtggct | 32520 |
| gatttctgac | agcattcaat | gccagtgtgg | gagattatgt | gctataccca t tcgaaaaca | 32580 |
| gtacaagtca | gaacctgagc | tcttaacttg | gcctttggtg | ccctgagctg g agtgacctc | 32640 |
| aggattcctc | acttcttcct | tctttcttcc | agaaccagca | gtcatcggcg g ctccaacct | 32700 |
| cacaggagag | aagcagcaac | ccagcccccc | gcaggcagca | ggcgtttgtg g cccctctct | 32760 |
| cccaagcccc | ctacaccttc | cagcatggca | gcccgctaca | ctcgacaggg c acccacacc | 32820 |
| ttgccccggc | ccctgctcac | ctgccaagcc | aggctcatct | gtatacgtat g ctgcccga | 32880 |
| cttctgctgc | tgcactgggc | tcaaccagct | ccattgctca | tcttttctcc c cacagggtt | 32940 |
| cctcaaggca | tgctgcagcc | tataccactc | accctagcac | tttggtgcac c aggtccctg | 33000 |
| tcagtgttgg | gccagcctc | ctcacttctg | ccagcgtggc | ccctgctcag t accaacacc | 33060 |
| agtttgccac | ccaatcctac | attgggtctt | cccgaggctc | aacaatttac a ctggatacc | 33120 |
| cgctgagtcc | taccaagatc | agccagtatt | cctacttata | gttggtgagc a tgagggagg | 33180 |
| aggaatcatg | gctaccttct | cctggccctg | cgttcttaat | attgggctat g gagagatcc | 33240 |
| tcctttaccc | tcttgaaatt | tcttagccag | caacttgttc | tgcagggcc c actgaagca | 33300 |
| gaaggttttt | ctctggggga | acctgtctca | gtgttgactg | cattgttgta g tcttcccaa | 33360 |
| agtttgccct | atttttaaat | tcattatttt | tgtgacagta | attttggtac t tggaagagt | 33420 |
| tcagatgccc | atcttctgca | gttaccaagg | aagagagatt | gttctgaagt t accctctga | 33480 |
| aaaatatttt | gtctctctga | cttgatttct | ataaatgctt | ttaaaaacaa g tgaagccccc | 33540 |
| tctttatttc | attttgtgtt | attgtgattg | ctggtcagga | aaaatgctga t agaaggagt | 33600 |
| tgaaatctga | tgacaaaaaa | agaaaaatta | cttttgtttt | gtttataaac t cagacttgc | 33660 |
| ctattttatt | ttaaaagcgg | cttacacaat | ctcccttttg | tttattggac a tttaaactt | 33720 |
| acagagtttc | agtttgtttt | taatgtcata | ttatacttaa | tgggcaattg t tattttgc | 33780 |
| aaaactggtt | acgtattact | ctgtgttact | attggagatt | ctctcaattg c tcctgtgtt | 33840 |
| tgttataaag | tagtgtttaa | aaggcagctc | accatttgct | ggtaacttaa t gtgagagaa | 33900 |
| tccatatctg | cgtgaaaaca | ccaagtattc | tttttaaatg | aagcaccatg a attctttt | 33960 |
| taaattattt | tttaaagtc | tttctctctc | tgattcagct | taaattttt t atcgaaaaa | 34020 |
| gccattaagg | tggttattat | tacatggtgg | tggtggtttt | attatatgca a aatctctgt | 34080 |
| ctattatgag | atactggcat | tgatgagctt | tgcctaaaga | ttagtatgaa t tttcagtaa | 34140 |
| tacacctctg | ttttgctcat | ctctcccttc | tgttttatgt | gatttgtttg g ggagaaagc | 34200 |
| taaaaaaacc | tgaaaccaga | taagaacatt | tcttgtgtat | agcttttata c ttcaaagta | 34260 |
| gcttcctttg | tatgccagca | gcaaattgaa | tgctctctta | ttaagactta t ataataagt | 34320 |
| gcatgtagga | attgcaaaaa | atatttaaa | aatttattac | tgaatttaaa a atattttag | 34380 |
| aagttttgta | atggtggtgt | tttaatattt | tacataatta | aatatgtaca t attgattag | 34440 |
| aaaaatataa | caagcaattt | ttcctgctaa | cccaaaatgt | tatttgtaat c aaatgtgta | 34500 |
| gtgattacac | ttgaattgtg | tacttagtgt | gtatgtgatc | ctccagtgtt a tcccggaga | 34560 |
| tggattgatg | tctccattgt | atttaaacca | aaatgaactg | atacttgttg g aatgtatgt | 34620 |
| gaactaattg | caattatatt | agagcatatt | actgtagtgc | tgaatgagca g gggcattgc | 34680 |

-continued

```
ctgcaaggag aggagaccct tggaattgtt ttgcacaggt gtgtctggtg a ggagttttt   34740 cagtgtgtgt ctcttccttc cctttcttcc tccttccctt attgtagtgc c ttatatgat   34800 aatgtagtgg ttaatagagt ttacagtgag cttgccttag gatggaccag c aagcccccg   34860 tggaccctaa gttgttcacc gggatttatc agaacaggat tagtagctgt a ttgtgtaat   34920 gcattgttct cagtttccct gccaacattg aaaaataaaa acagcagctt t tctccttta   34980 ccaccacctc taccccttc cattttggat tctcggctga gttctcacag a agcattttc    35040 cccatgtggc tctctcactg tgcgttgcta ccttgcttct gtgagaattc a ggaagcagg   35100 tgagaggagt caagccaata ttaaatatgc attctttaa agtatgtgca a tcactttta    35160 gaatgaattt tttttccctt tcccatgtg gcagtccttc ctgcacatag t tgacattcc    35220 tagtaaaata tttgcttgtt gaaaaaaaca tgttaacaga tgtgtttata c caaagagcc   35280 tgttgtattg cttaccatgt ccccatacta tgaggagaag ttttgtggtg c cgctggtga   35340 caaggaactc acagaaaggt ttcttagctg gtgaagaata tagagaagga a ccaaagcct   35400 gttgagtcat tgaggctttt gaggtttctt ttttaacagc ttgtatagtc t tggggccct   35460 tcaagctgtg aaattgtcct tgtactctca gctcctgcat ggatctgggt c aagtagaag   35520 gtactgggga tggggacatt cctgcccata aggatttgg ggaaagaaga t taatcctaa    35580 aatacaggtg tgttccatct gaattgaaaa tgatatattt gagatataat t ttaggactg   35640 gttctgtgta gatagagatg gtgtcaagga ggtgcaggat ggagatggga g atttcatgg   35700 agcctggtca gccagctctg taccaggttg aacaccgagg agctgtcaaa g tatttggag   35760 tttcttcatt gtaaggagta agggcttcca agatggggca ggtagtccgt a cagcctacc   35820 aggaacatgt tgtgttttcn nnnnnnnnnn nnnnnnnnn nnnnnnnnnn n nnnnnnnnn    35880 nnnnnnnnna agatgggagg atagcttgag cccagaggtt gaggtcgcag c gagctgtga   35940 tcactccact gcactccagc ctgggtgaca gaacaagacg ctgtcacaca c acaaaaaag   36000 aacaattcaa ttttcatgta ttttctttt cctcagctct ggactgaagc c aaggtctaa    36060 tgtcatcagt tatgtcactg tcaatgattc tccagactct gactcttctt t gagcagccc   36120 ttattccact gatacctga gtgctctccg aggcaatag                            36159
```

<210> SEQ ID NO 4
<211> LENGTH: 1209
<212> TYPE: PRT
<213> ORGANISM: Mus musculus

<400> SEQUENCE: 4

```
Met Ala Ser Gln Leu Gln Val Phe Ser Pro Pro ro Ser Val Ser Ser
  1               5                  10                  15

Ala Phe Cys Ser Ala Lys Lys Leu Lys Ile G lu Pro Ser Gly Trp Asp
                 20                  25                  30

Val Ser Gly Gln Ser Ser Asn Asp Lys Tyr T yr Thr His Ser Lys Thr
             35                  40                  45

Leu Pro Ala Thr Gln Gly Gln Ala Ser Ser S er His Gln Val Ala Asn
         50                  55                  60

Phe Asn Leu Pro Ala Tyr Asp Gln Gly Leu L eu Leu Pro Ala Pro Ala
 65                  70                  75                  80

Val Glu His Ile Val Val Thr Ala Ala Asp S er Gly Ser Ala Ala
                 85                  90                  95

Thr Ala Thr Phe Gln Ser Ser Gln Thr Leu T hr His Arg Ser Asn Val
                100                 105                 110
```

-continued

```
Ser Leu Leu Glu Pro Tyr Gln Lys Cys Gly L eu Lys Arg Lys Ser Glu
            115                 120                 125
Glu Val Glu Ser Asn Gly Ser Val Gln Ile I le Glu Glu His Pro Pro
130                 135                 140
Leu Met Leu Gln Asn Arg Thr Val Val Gly A la Ala Ala Thr Thr Thr
145                 150                 155                 160
Thr Val Thr Thr Lys Ser Ser Ser Ser G ly Glu Gly Asp Tyr Gln
                165                 170                 175
Leu Val Gln His Glu Ile Leu Cys Ser Met T hr Asn Ser Tyr Glu Val
            180                 185                 190
Leu Glu Phe Leu Gly Arg Gly Thr Phe Gly G ln Val Ala Lys Cys Trp
            195                 200                 205
Lys Arg Ser Thr Lys Glu Ile Val Ala Ile L ys Ile Leu Lys Asn His
            210                 215                 220
Pro Ser Tyr Ala Arg Gln Gly Gln Ile Glu V al Ser Ile Leu Ser Arg
225                 230                 235                 240
Leu Ser Ser Glu Asn Ala Asp Glu Tyr Asn P he Val Arg Ser Tyr Glu
                245                 250                 255
Cys Phe Gln His Lys Asn His Thr Cys Leu V al Phe Glu Met Leu Glu
            260                 265                 270
Gln Asn Leu Tyr Asp Phe Leu Lys Gln Asn L ys Phe Ser Pro Leu Pro
            275                 280                 285
Leu Lys Tyr Ile Arg Pro Ile Leu Gln Gln V al Ala Thr Ala Leu Met
            290                 295                 300
Lys Leu Lys Ser Leu Gly Leu Ile His Ala A sp Leu Lys Pro Glu Asn
305                 310                 315                 320
Ile Met Leu Val Asp Pro Val Arg Gln Pro T yr Arg Val Lys Val Ile
                325                 330                 335
Asp Phe Gly Ser Ala Ser His Val Ser Lys A la Val Cys Ser Thr Tyr
            340                 345                 350
Leu Gln Ser Arg Tyr Tyr Arg Ala Pro Glu I le Ile Leu Gly Leu Pro
            355                 360                 365
Phe Cys Glu Ala Ile Asp Met Trp Ser Leu G ly Cys Val Ile Ala Glu
            370                 375                 380
Leu Phe Leu Gly Trp Pro Leu Tyr Pro Gly A la Ser Glu Tyr Asp Gln
385                 390                 395                 400
Ile Arg Tyr Ile Ser Gln Thr Gln Gly Leu P ro Ala Glu Tyr Leu Leu
                405                 410                 415
Ser Ala Gly Thr Lys Thr Thr Arg Phe Phe A sn Arg Asp Pro Asn Leu
            420                 425                 430
Gly Tyr Pro Leu Trp Arg Leu Lys Thr Pro G lu Glu His Glu Leu Glu
            435                 440                 445
Thr Gly Ile Lys Ser Lys Glu Ala Arg Lys T yr Ile Phe Asn Cys Leu
            450                 455                 460
Asp Asp Met Ala Gln Val Asn Met Ser Thr A sp Leu Glu Gly Thr Asp
465                 470                 475                 480
Met Leu Ala Glu Lys Ala Asp Arg Arg Glu T yr Ile Asp Leu Leu Lys
            485                 490                 495
Lys Met Leu Thr Ile Asp Ala Asp Lys Arg I le Thr Pro Leu Lys Thr
            500                 505                 510
Leu Asn His Gln Phe Val Thr Met Ser His L eu Leu Asp Phe Pro His
            515                 520                 525
```

```
Ser Ser His Val Lys Ser Cys Phe Gln Asn Met Glu Ile Cys Lys Arg
    530                 535                 540
Arg Val His Met Tyr Asp Thr Val Ser Gln Ile Lys Ser Pro Phe Thr
545                 550                 555                 560
Thr His Val Ala Pro Asn Thr Ser Thr Asn Leu Thr Met Ser Phe Ser
                565                 570                 575
Asn Gln Leu Asn Thr Val His Asn Gln Ala Ser Val Leu Ala Ser Ser
            580                 585                 590
Ser Thr Ala Ala Ala Thr Leu Ser Leu Ala Asn Ser Asp Val Ser
        595                 600                 605
Leu Leu Asn Tyr Gln Ser Ala Leu Tyr Pro Ser Ser Ala Ala Pro Val
    610                 615                 620
Pro Gly Val Ala Gln Gln Gly Val Ser Leu Gln Pro Gly Thr Thr Gln
625                 630                 635                 640
Ile Cys Thr Gln Thr Asp Pro Phe Gln Gln Thr Phe Ile Val Cys Pro
                645                 650                 655
Pro Ala Phe Gln Thr Gly Leu Gln Ala Thr Thr Lys His Ser Gly Phe
            660                 665                 670
Pro Val Arg Met Asp Asn Ala Val Pro Ile Val Pro Gln Ala Pro Ala
        675                 680                 685
Ala Gln Pro Leu Gln Ile Gln Ser Gly Val Leu Thr Gln Gly Ser Cys
    690                 695                 700
Thr Pro Leu Met Val Ala Thr Leu His Pro Gln Val Ala Thr Ile Thr
705                 710                 715                 720
Pro Gln Tyr Ala Val Pro Phe Thr Leu Ser Cys Ala Gly Arg Pro Ala
                725                 730                 735
Leu Val Glu Gln Thr Ala Ala Val Leu Gln Ala Trp Pro Gly Gly Thr
            740                 745                 750
Gln Gln Ile Leu Leu Pro Ser Ala Trp Gln Gln Leu Pro Gly Val Ala
        755                 760                 765
Leu His Asn Ser Val Gln Pro Ala Ala Val Ile Pro Glu Ala Met Gly
    770                 775                 780
Ser Ser Gln Gln Leu Ala Asp Trp Arg Asn Ala His Ser His Gly Asn
785                 790                 795                 800
Gln Tyr Ser Thr Ile Met Gln Gln Pro Ser Leu Leu Thr Asn His Val
                805                 810                 815
Thr Leu Ala Thr Ala Gln Pro Leu Asn Val Gly Val Ala His Val Val
            820                 825                 830
Arg Gln Gln Gln Ser Ser Ser Leu Pro Ser Lys Lys Asn Lys Gln Ser
        835                 840                 845
Ala Pro Val Ser Ser Lys Ser Ser Leu Glu Val Leu Pro Ser Gln Val
    850                 855                 860
Tyr Ser Leu Val Gly Ser Ser Pro Leu Arg Thr Thr Ser Ser Tyr Asn
865                 870                 875                 880
Ser Leu Val Pro Val Gln Asp Gln His Gln Pro Ile Ile Ile Pro Asp
                885                 890                 895
Thr Pro Ser Pro Pro Val Ser Val Ile Thr Ile Arg Ser Asp Thr Asp
            900                 905                 910
Glu Glu Glu Asp Asn Lys Tyr Glu Pro Asn Ser Ser Ser Leu Lys Ala
        915                 920                 925
Arg Ser Asn Val Ile Ser Tyr Val Thr Val Asn Asp Ser Pro Asp Ser
    930                 935                 940
Asp Ser Ser Leu Ser Ser Pro His Ser Thr Asp Thr Leu Ser Ala Leu
```

-continued

```
945                 950                 955                 960
Arg Gly Asn Ser Gly Thr Leu Leu Glu Gly P ro Gly Arg Pro Ala Ala
                965                 970                 975
Asp Gly Ile Gly Thr Arg Thr Ile Ile Val P ro Pro Leu Lys Thr Gln
            980                 985                 990
Leu Gly Asp Cys Thr Val Ala Thr Gln Ala S er Gly Leu Leu Ser Ser
        995                 1000                1005
Lys Thr Lys Pro Val Ala Ser Val Ser Gly G ln Ser Ser Gly Cys Cys
    1010                1015                1020
Ile Thr Pro Thr Gly Tyr Arg Ala Gln Arg G ly Gly Ala Ser Ala Val
1025                103 0                1035                1040
Gln Pro Leu Asn Leu Ser Gln Asn Gln Gln S er Ser Ser Ala Ser Thr
                1045                1050                1055
Ser Gln Glu Arg Ser Ser Asn Pro Ala Pro A rg Arg Gln Gln Ala Phe
            1060                1065                1070
Val Ala Pro Leu Ser Gln Ala Pro Tyr Ala P he Gln His Gly Ser Pro
        1075                1080                1085
Leu His Ser Thr Gly His Pro His Leu Ala P ro Ala Pro Ala His Leu
    1090                1095                1100
Pro Ser Gln Pro His Leu Tyr Thr Tyr Ala A la Pro Thr Ser Ala Ala
1105                111 0                1115                1120
Ala Leu Gly Ser Thr Ser Ser Ile Ala His L eu Phe Phe Pro Gln Gly
                1125                1130                1135
Ser Ser Arg His Ala Ala Ala Tyr Thr Thr H is Pro Ser Thr Leu Val
            1140                1145                1150
His Gln Val Pro Val Ser Val Gly Pro Ser L eu Leu Thr Ser Ala Ser
        1155                1160                1165
Val Ala Pro Ala Gln Tyr Gln His Gln Phe A la Thr Gln Ser Tyr Ile
    1170                1175                1180
Gly Ser Ser Arg Gly Ser Thr Ile Tyr Thr G ly Tyr Pro Leu Ser Pro
1185                119 0                1195                1200
Thr Lys Ile Ser Gln Tyr Ser Tyr Leu
                1205
```

US 6,423,521 B1

ISOLATED HUMAN KINASE PROTEINS, NUCLEIC ACID MOLECULES ENCODING HUMAN KINASE PROTEINS, AND USES THEREOF

FIELD OF THE INVENTION

The present invention is in the field of kinase proteins that are related to the homeodomain-interacting protein kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A–XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Iinternal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell. Biol.* 8:463–93). Regulation of PTK activity may therefore be an important strategy in controlling some types of cancer.

Homeodomain-Interacting Protein Kinases

The novel human protein, and encoding gene, provided by the present invention is related to the family of homeodomain-interacting protein kinases (HIPKs). HIPKs are nuclear kinases that act as transcriptional co-repressors for homeodomain transcription factors. HIPKs enhance the repressor functions of NK homeoproteins. The HIPK family comprises at least three previously described members: HIPK1, HIPK2, and HIPK3. HIPKs comprise a conserved protein kinase domain and a separate homeoprotein/homeodomain interaction domain. HIPK2 has been found to significantly increase the DNA binding activity of the NK-3 homeoprotein (Kim et al., *J Biol Chem Oct.* 2, 1998;273 (40):25875–9).

HIPKs show a high degree of similarity to yeast YAK1 proteins, human PKY (protein kinase YAK1 homolog), and Myak (mouse YAK homolog) proteins, which play important roles in cellular regulation and signaling, multidrug resistance, and in restricting cell growth. For a further review of HIPKs, YAK1, and PKY proteins, see Begley et al., *Gene* 200: 35–43, 1997; Nupponen et al., *Cytogenet. Cell Genet.* 87: 102–103, 1999; and Sampson et al., *J. Cell. Biochem.* 52: 384–395, 1993.

Kinase proteins, particularly members of the homeodomain-interacting protein kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the homeodomain-interacting protein kinase subfamily.

SUMMARY OF THE INVENTION

The present invention is based in part on the identification of amino acid sequences of human kinase peptides and proteins that are related to the homeodomain-interacting protein kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in humans in testis, brain medulloblastomas, infant brain, schizophrenic brain, retina, germinal center B cells, colon, and liver.

DESCRIPTION OF THE FIGURE SHEETS

FIG. 1 provides the nucleotide sequence of a cDNA molecule that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in testis, brain medulloblastomas, infant brain, schizophrenic brain, retina, germinal center B cells, colon, and liver.

FIG. 2 provides the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, the following SNPs were identified: T4452A, A5330G, A9256C, A11773G, G12886A, and a T insertion/deletion ("indel") at position 14131.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the homeodomain-interacting protein kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the homeodomain-interacting protein kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the homeodomain-interacting protein kinase subfamily and the expression pattern observed. Experimental data as provided in FIG. 1 indicates expression in humans in testis, brain medulloblastomas, infant brain, schizophrenic brain, retina, germinal center B cells, colon, and liver. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known homeodomain-interacting protein kinase family or subfamily of kinase proteins.

Specific Embodiments
Peptide Molecules

The present invention provides nucleic acid sequences that encode protein molecules that have been identified as being members of the kinase family of proteins and are related to the homeodomain-interacting protein kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in humans in testis, brain medulloblastomas, infant brain, schizophrenic brain, retina, germinal center B cells, colon, and liver. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:1). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In a preferred embodiment, the percent identity between two amino acid sequences is determined using the Needleman and Wunsch (J. Mol. Biol. (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., Nucleic Acids Res. 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. The gene encoding the novel kinase protein of the present invention is located on a genome component that has been mapped to human chromosome 1 (as indicated in FIG. 3), which is supported by multiple lines of evidence, such as STS and BAC map data.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. The gene encoding the novel kinase protein of the present invention is located on a genome component that has been mapped to human chromosome 1 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the kinase protein of the present invention. The following variations were seen: T4452A, A5330G, A9256C, A11773G, G12886A, and a T insertion/deletion ("indel") at position 14131. SNPs in introns, such as these, may affect control/regulatory elements.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol*. 182: 626–646 (1990)) and Rattan et al. (Ann. N.Y. *Acad. Sci*. 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in humans in testis, brain medulloblastomas, infant brain, schizophrenic brain, retina, germinal center B cells, and colon, as indicated by virtual northern blot analysis. In addition, PCR-based tissue screening panels indicate expression in human liver. A large percentage of pharmaceutical agents are being developed that modulate the activity of kinase proteins, particularly members of the homeodomain-interacting protein kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in testis, brain medulloblastomas, infant brain, schizophrenic brain, retina, germinal center B cells, colon, and liver. Such uses can readily be determined using the information provided herein, that which is known in the art, and routine experimentation.

The proteins of the present invention (including variants and fragments that may have been disclosed prior to the present invention) are useful for biological assays related to kinases that are related to members of the homeodomain-interacting protein kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in humans in testis, brain medulloblastomas, infant brain, schizophrenic brain, retina, germinal center B cells, and colon, as indicated by virtual northern blot analysis. In addition, PCR-based tissue screening panels indicate expression in human liver.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in humans in testis, brain medulloblastomas, infant brain, schizophrenic brain, retina, germinal center B cells, colon, and liver. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in humans in testis, brain medulloblastomas, infant brain, schizophrenic brain, retina, germinal center B cells, and colon, as indicated by virtual northern blot analysis. In addition, PCR-based tissue screening panels indicate expression in human liver.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in humans in testis, brain medulloblastomas, infant brain, schizophrenic brain, retina, germinal center B cells, colon, and liver. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent W)94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in testis, brain medulloblastomas, infant brain, schizophrenic brain, retina, germinal center B cells, colon, and liver. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharrmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in testis, brain medulloblastomas, infant brain, schizophrenic brain, retina, germinal center B cells, colon, and liver. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in humans in testis, brain medulloblastomas, infant brain, schizophrenic brain, retina, germinal center B cells, and colon, as indicated by virtual northern blot analysis. In addition, PCR-based tissue screening panels indicate expression in human liver. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in testis, brain medulloblastomas, infant brain, schizophrenic brain, retina, germinal center B cells, colon, and liver. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in testis, brain medulloblastomas, infant brain, schizophrenic brain, retina, germinal center B cells, colon, and liver. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in testis, brain medulloblastomas, infant brain, schizophrenic brain, retina, germinal center B cells, colon, and liver. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel kinase protein of the present invention is located on a genome component that has been mapped to human chromosome 1 (as indicated in FIG. 3), which is supported by multiple lines of evidence, such as STS and BAC map data.

FIG. 3 provides information on SNPs that have been found in the gene encoding the kinase protein of the present invention. The following variations were seen: T4452A, A5330G, A9256C, A11773G, G12886A, and a T insert/deletion ("indel") at position 14131. SNPs in introns, such as these, may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45 C, followed by one or more washes in 0.2×SSC, 0.1% SDS at 50–60 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, the following SPNs were identified: T4452A, A5330G, A9256C, A11773G, G12886A, and T insertion/deletion ("indel") at position 14131.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel kinase protein of the present invention is located on a genome component that has been mapped to human chromosome 1 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in humans in testis, brain medulloblastomas, infant brain, schizophrenic brain, retina, germinal center B cells, and colon, as indicated by virtual northern blot analysis. In addition, PCR-based tissue screening panels indicate expression in human liver. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in humans in testis, brain medulloblastomas, infant brain, schizophrenic brain, retina, germinal center B cells, and colon, as indicated by virtual northern blot analysis. hi addition, PCR-based tissue screening panels indicate expression in human liver.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in humans in testis, brain medulloblastomas, infant brain, schizophrenic brain, retina, germinal center B cells, colon, and liver. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in humans in testis, brain medulloblastomas, infant brain, schizophrenic brain, retina, germinal center B cells, and colon, as indicated by virtual northern blot analysis. In addition, PCR-based tissue screening panels indicate expression in human liver. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in humans in testis, brain medulloblastomas, infant brain, schizophrenic brain, retina, germinal center B cells, colon, and liver.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the kinase protein of the present invention. The following variations were seen: T4452A, A5330G, A9256C, A11773G, G12886A, and a T insertion/deletion ("indel") at position 14131. SNPs in introns, such as these, may affect control/regulatory elements. The gene encoding the novel kinase protein of the present invention is located on a genome component that has been mapped to human chromosome 1 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1 080 (1988); and Nakazawa et al., PNAS 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et a., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the kinase protein of the present invention. The following variations were seen: T4452A, A5330G, A9256C, A11773G, G12886A, and a T insertion/deletion ("indel") at position 14131. SNPs in introns, such as these, may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in humans in testis, brain medulloblastomas, infant brain, schizophrenic brain, retina, germinal center B cells, and colon, as indicated by virtual northern blot analysis. In addition, PCR-based tissue screening panels indicate expression in human liver.

For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.)

which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one z z million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the kinase protein of the present invention. The following variations were seen: T4452A, A5330G, A9256C, A11773G, G12886A, and a T insertion/deletion ("indel") at position 14131. SNPs in introns, such as these, may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats go known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leader et al., U.S. Pat. No. 4,873,191 by Wagner et al., and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes a protein comprising the amino acid sequence of SEQ ID NO:2;
   (b) a nucleotide sequence consisting of SEQ ID NO:1;
   (c) a nucleotide sequence consisting of SEQ ID NO:3; and
   (d) a nucleotide sequence that is completely complementary to a nucleotide sequence of (a)–(c).

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering said polypeptide from the host cell culture.

5. An isolated polynucleotide consisting of a nucleotide sequence set forth in SEQ ID NO:1.

6. An isolated polynucleotide consisting of a nucleotide sequence set forth in SEQ ID NO:3.

7. A vector according to claim 2, wherein said vector is selected from the group consisting of a plasmid, virus, and bacteriophage.

8. A vector according to claim 2, wherein said isolated nucleic acid molecule is inserted into said vector in proper orientation and correct reading frame such that the protein of SEQ ID NO:2 may be expressed by a cell transformed with said vector.

9. A vector according to claim 8, wherein said isolated nucleic acid molecule is operatively linked to a promoter sequence.

* * * * *